United States Patent
Tworowska et al.

(10) Patent No.: US 11,541,133 B2
(45) Date of Patent: Jan. 3, 2023

(54) TREATMENT OF CANCER CELLS OVEREXPRESSING SOMATOSTATIN RECEPTORS USING OCREOTIDE DERIVATIVES CHELATED TO RADIOISOTOPES

(71) Applicants: RADIOMEDIX INC., Houston, TX (US); ORANO MED, Courbevoie (FR)

(72) Inventors: Izabela Tworowska, Houston, TX (US); Nilesh Wagh, Houston, TX (US); Ebrahim S. Delpassand, Houston, TX (US); Federico Rojas-Quijano, Bedford, TX (US); Paul Jurek, Red Oak, TX (US); Garry E. Kiefer, Richardson, TX (US); Tania A. Stallons, Wylie, TX (US); Amal Saidi, Thomon-les-Bains. (FR); Julien Torgue, Gaithersburg, MD (US)

(73) Assignees: RADIOMEDIX INC., Houston, TX (US); ORANO MED, Courbevoie (FR)

(*) Notice: Subject to any disclaimer, the term of this patent is extended or adjusted under 35 U.S.C. 154(b) by 0 days.

(21) Appl. No.: 16/477,623

(22) PCT Filed: Jan. 12, 2018

(86) PCT No.: PCT/US2018/013640
§ 371 (c)(1),
(2) Date: Jul. 12, 2019

(87) PCT Pub. No.: WO2018/132751
PCT Pub. Date: Jul. 19, 2018

(65) Prior Publication Data
US 2019/0336623 A1 Nov. 7, 2019

Related U.S. Application Data

(60) Provisional application No. 62/445,541, filed on Jan. 12, 2017.

(51) Int. Cl.
| | | |
|---|---|---|
| *A61K 51/08* | (2006.01) | |
| *A61P 35/00* | (2006.01) | |
| *A61K 51/04* | (2006.01) | |
| *A61K 47/10* | (2017.01) | |
| *A61K 47/12* | (2006.01) | |
| *A61K 47/18* | (2017.01) | |
| *A61K 47/22* | (2006.01) | |
| *A61K 45/06* | (2006.01) | |

(52) U.S. Cl.
CPC ............ *A61K 51/083* (2013.01); *A61K 47/10* (2013.01); *A61K 47/12* (2013.01); *A61K 47/183* (2013.01); *A61K 47/22* (2013.01); *A61K 51/0482* (2013.01); *A61K 51/088* (2013.01); *A61P 35/00* (2018.01); *A61K 45/06* (2013.01)

(58) Field of Classification Search
CPC ...... A61K 51/00; A61K 51/08; A61K 51/083; A61K 51/088; A61K 51/04; A61K 47/00; A61K 47/10; A61K 47/12; A61K 47/183; A61K 47/22; A61K 45/00; A61K 45/06; A61P 35/00
USPC ........ 424/1.11, 1.65, 1.69, 9.1, 9.2, 9.3, 9.4, 424/9.5; 534/7, 10–16; 514/1, 1.1, 11.1, 514/19.2, 19.3, 19.4, 19.5, 19.6, 21.1, 514/21.8; 530/300, 311, 317, 329
See application file for complete search history.

(56) References Cited

U.S. PATENT DOCUMENTS

| | | |
|---|---|---|
| 5,804,157 A | 9/1998 | Srinivasan et al. |
| 5,830,431 A | 11/1998 | Srinivasan et al. |
| 6,017,512 A * | 1/2000 | Dean ................... A61K 51/088 424/1.11 |
| 6,123,916 A | 9/2000 | Krenning et al. |
| 6,183,721 B1 | 2/2001 | Albert et al. |
| 6,207,805 B1 | 3/2001 | Weiner et al. |
| 6,225,284 B1 | 5/2001 | Albert et al. |
| 6,358,491 B1 | 3/2002 | Lister-James et al. |
| 6,512,096 B2 | 1/2003 | Weiner et al. |
| 6,683,162 B2 | 1/2004 | Scheinberg et al. |
| 6,866,837 B2 | 3/2005 | Reubi et al. |
| 6,926,883 B1 | 8/2005 | Dyszlewski et al. |
| 7,192,570 B2 | 3/2007 | Maecke et al. |
| 7,202,330 B2 | 4/2007 | Dejong et al. |

(Continued)

FOREIGN PATENT DOCUMENTS

| | | |
|---|---|---|
| CN | 106084005 A | 11/2016 |
| WO | 2014/052471 A1 | 4/2014 |
| WO | 2016/046793 A2 | 3/2016 |

OTHER PUBLICATIONS

Li etal, Applied Radiation and Isotopes, May 2017, vol. 127, pp. 52-60. (Year: 2017).*

(Continued)

*Primary Examiner* — D. L. Jones
(74) *Attorney, Agent, or Firm* — ArentFox Schiff LLP

(57) ABSTRACT

A cancer targeting composition, kit, and method for treatment of cancer cells overexpressing somatostatin receptors is disclosed. The composition includes a radioisotope, a chelator, and a targeting moiety. The chelator includes a nitrogen ring structure including a tetraazacyclododecane, a triazacyclononane, and/or a tetraazabicyclo [6.6.2] hexadecane derivative. The targeting moiety includes a somatostatin receptor targeting peptide. The somatostatin receptor targeting peptide includes an octreotide derivative. The targeting moiety is chelated to the radioisotope by the chelator whereby the cancer cells are targeted for elimination.

22 Claims, 32 Drawing Sheets

(56) References Cited

U.S. PATENT DOCUMENTS

| | | |
|---|---|---|
| 7,361,346 B1 | 4/2008 | Madiyalakan et al. |
| 7,541,018 B2 | 6/2009 | Maecke et al. |
| 8,097,237 B2 | 1/2012 | Norenberg et al. |
| 8,119,103 B2 | 2/2012 | Moore |
| 8,193,347 B2 | 6/2012 | Moore |
| 8,435,489 B2 | 5/2013 | Norenberg et al. |
| 8,575,100 B2 | 11/2013 | Wester et al. |
| 8,623,322 B2 | 1/2014 | Norenberg |
| 8,703,937 B2 | 4/2014 | Moore |
| 8,834,838 B2 | 9/2014 | Norenberg |
| 8,858,916 B2 | 10/2014 | Moore |
| 8,986,651 B2 | 3/2015 | Miao et al. |
| 9,035,023 B2 | 5/2015 | Maecke et al. |
| 9,056,138 B2 | 6/2015 | Fan et al. |
| 9,180,214 B1 | 11/2015 | Miao |
| 9,217,009 B2 | 12/2015 | Moore |
| 9,315,474 B2 | 4/2016 | Moore et al. |
| 9,352,059 B2 | 5/2016 | Norenberg |
| 9,408,928 B2 | 8/2016 | Azhdarinia et al. |
| 10,159,759 B2 * | 12/2018 | Kjaer .................. A61K 51/088 |
| 10,383,961 B2 * | 8/2019 | Kjaer .................. A61K 51/083 |
| 2004/0044177 A1 | 3/2004 | Macke et al. |
| 2007/0025910 A1 | 2/2007 | Norenberg |
| 2012/0220754 A1 | 8/2012 | Simon et al. |
| 2014/0147381 A1 | 5/2014 | Espenan |
| 2014/0228551 A1 | 8/2014 | Tworowska et al. |
| 2015/0157742 A1 | 6/2015 | Morgenstern et al. |
| 2015/0196673 A1 | 7/2015 | Norenberg |
| 2016/0143926 A1 | 5/2016 | Delpassand et al. |

OTHER PUBLICATIONS

Oehlke et al., "Influence of Metal Ions on the ""GA-labeling of DOTATATE," Applied Radiation and Isotopes 2013, vol. 32, 232-238.

Sprague et al., "Preparation and Biological Evaluation of Copper-64-Labeled Tyr$^3$-Octreotate Using a Cross-Bridged Macrocyclic Chelator," Clinical Cancer Research 2004, vol. 10, No. 24, 8674-8682.

Dai Zhengxin et al., "$^{69}$Cu-labled Somatostatin Analogues Conjugated with Cross-Bridged Phosphonate-Based Chelators via Strain-Promoted Click Chemistry for PET Imaging: In silico through in Vivo Studies," Journal of Medicinal Chemistry 2014, vol. 57, No. 14, 6019-6029.

* cited by examiner

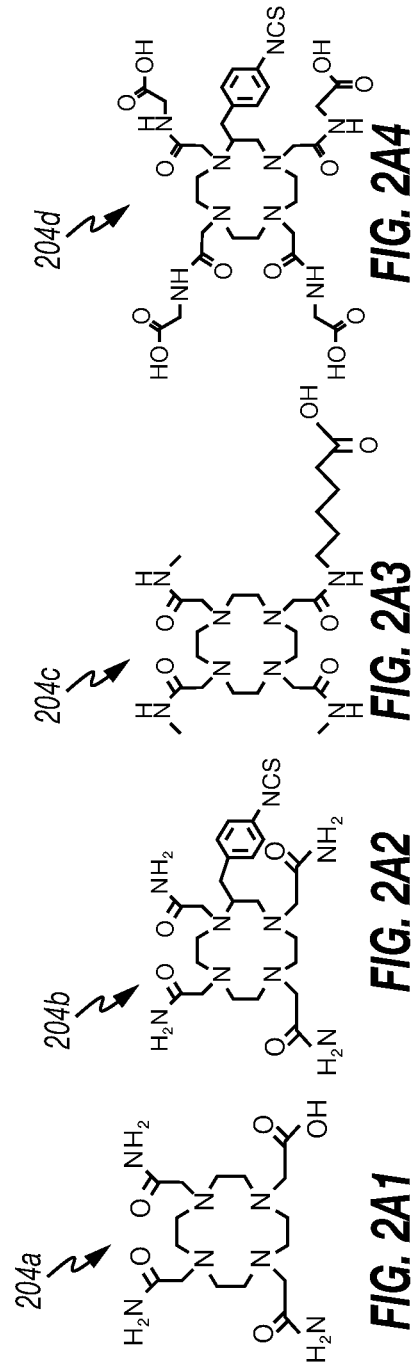
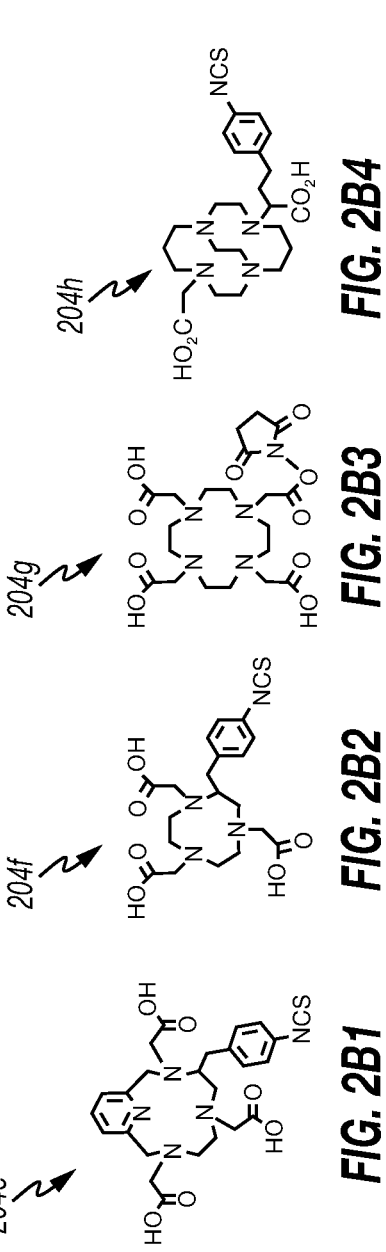
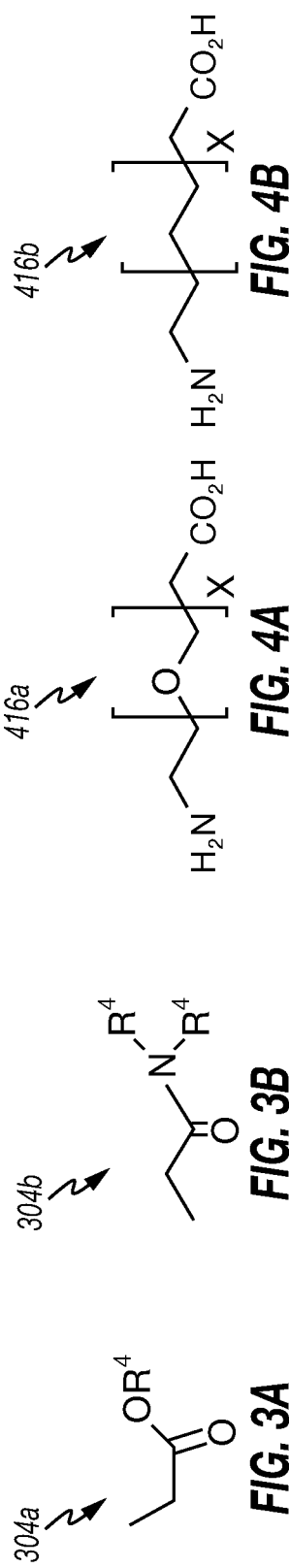

TREATMENT OF CANCER CELLS OVEREXPRESSING SOMATOSTATIN RECEPTORS USING OCREOTIDE DERIVATIVES CHELATED TO RADIOISOTOPES

CROSS-REFERENCE TO RELATED APPLICATIONS

This application claims the benefit of U.S. Provisional Application No. 62/445,541, which was filed on Jan. 12, 2017, and PCT Application No. PCT/US2018/013640, which was filed on Jan. 12, 2018, the entire contents of which being hereby incorporated by reference herein.

BACKGROUND

The present disclosure relates generally to cancer treatment. More particularly, the present disclosure relates to targeted radiotherapy of cancer patients using radiolabeled conjugates.

Various medications have been developed for the treatment of cancer cells. In order to specifically target the cancer cells, targeting compositions have been developed to treat to the cancer cells without affecting healthy cells which may be near the cancer cells. To target the cancer cells, the targeting compositions are provided with chemicals which are designed to bind specifically to portions of the cancer cells. Such compositions may be overexpressed in cancer cells compared to healthy cells. These compositions are also designed to bind to and damage the cancer cells without damaging other cells in the patient.

Examples of conjugates used in cancer treatment are provided in US Patent/Application Nos. 2016/0143926, 2015/0196673, 2014/0228551, 9408928, 9217009, 8858916, 7202330, 6225284, 6683162, 6358491, and WO2014052471, the entire contents of which are hereby incorporated by reference herein. Examples of tumor targeting compositions are provided in US Patent/Application Nos. US2007/0025910, and U.S. Pat. No. 5,804,157, the entire contents of which are hereby incorporated by reference herein.

Additional information concerning cancer treatment is provided in Milenic et al., Bench to Bedside: Stability Studies of GMP Produced Trastuzumab-TCMC in Support of a Clinical Trial, Pharmaceuticals, vol. 8, pp. 435-454 (2015); Tan et al., Biodistribution of $^{212}$Pb Conjugated Trastuzumab in Mice. J Radioanal Nucl. Chem., Journal of Radioanalytical and Nuclear Chemistry, April 2012; Boudousq et al., Comparison between Internalizing Anti-HER2 mAbs and Non-Internalizing Anti-CEA mAbs in Alpha-Radioimmunotherapy of Small Volume Peritoneal Carcinomatosis Using $^{212}$Pb, July 2013; Dr. Fisher, Development and Testing of a $^{212}$Pb/$^{212}$Bi Peptide for Targeting Metastatic Melanoma, U.S. Department of Energy, October 2012; Meredith et al., Dose Escalation and Dosimetry of First in Human Alpha Radioimmunotherapy with $^{212}$Pb-TCMC-trastuzumab, J Nucl Med., 55(10): 1636-1642, October 2014; Elgqvist et al., The Potential and Hurdles of Targeted Alpha Therapy—Clinical Trials and Beyond, Frontiers In Oncology, Jan. 14, 2014; Miao et al., Melanoma Therapy via Peptide-Targeted A-Radiation, Clinical Cancer Research, 11 (15), www.aacrjournals.org, Aug. 1, 2005; Meredith et al., Pharmacokinetics and Imaging of $^{212}$Pb-TCMC-Trastuzumab After Intraperitoneal Administration in Ovarian Cancer Patients, Cancer Biotherapy and Radiopharmaceuticals, Vol. 29, Number 1, (2014); Yong et al., Towards Translation of $^{212}$Pb as a Clinical Therapeutic: Getting The Lead In!, National Institute of Health, Dalton Trans., 40(23), Jun. 21, 2011; Milenic et al., Toxicological Studies of $^{212}$Pb Intravenously or Intraperitoneally Injected into Mice for a Phase 1 Trial, Pharmaceuticals, vol. 8, pp. 416-434 (2015), the entire contents of which are hereby incorporated by reference herein.

Despite advances in the treatment of cancer, there remains a need to provide effective and safely targeted radiotherapy for eliminating the cancer cells without damaging the healthy cells in the cancer patient. The present disclosure is directed at meeting such a need.

SUMMARY

In at least one aspect, the disclosure relates to a cancer targeting composition for treatment of cancer cells overexpressing somatostatin receptors. The composition comprises a radioisotope, a chelator, and a targeting moiety. The chelator comprises a nitrogen ring structure. The nitrogen ring structure comprises a derivative selected from the group consisting of a tetraazacyclododecane derivative, a triazacyclononane derivative, and a tetraazabicyclo [6.6.2] hexadecane derivative. The targeting moiety comprises a somatostatin receptor targeting peptide. The somatostatin receptor targeting peptide comprises an octreotide derivative, and is conjugated to the chelator coordinating the radioisotope whereby the cancer cells are targeted for elimination and treated.

A cancer targeting composition for treatment of cancer cells overexpressing somatostatin receptors is disclosed herein. The cancer targeting composition includes a radioisotope; a chelator comprising a nitrogen ring structure, the nitrogen ring structure comprising a derivative selected from the group consisting of a tetraazacyclododecane derivative, a triazacyclononane derivative, and a tetraazabicyclo[6.6.2] hexadecane derivative; and a targeting moiety comprising a somatostatin receptor targeting peptide, the somatostatin receptor targeting peptide comprising an octreotide derivative, the targeting moiety being conjugated to the chelator coordinating the radioisotope whereby the cancer cells are targeted for elimination and treated; or a product thereof.

The composition has the following chemical structure:

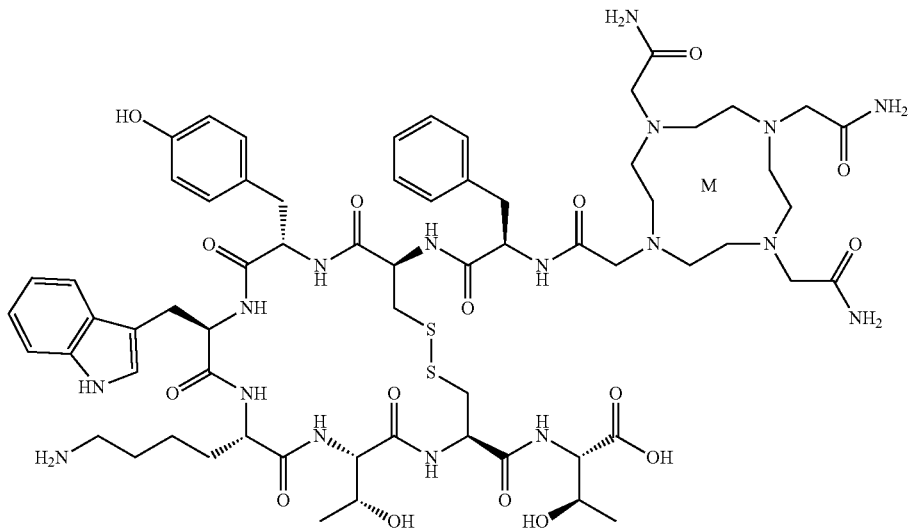

where M is the radioisotope.

The composition has the following chemical structure:

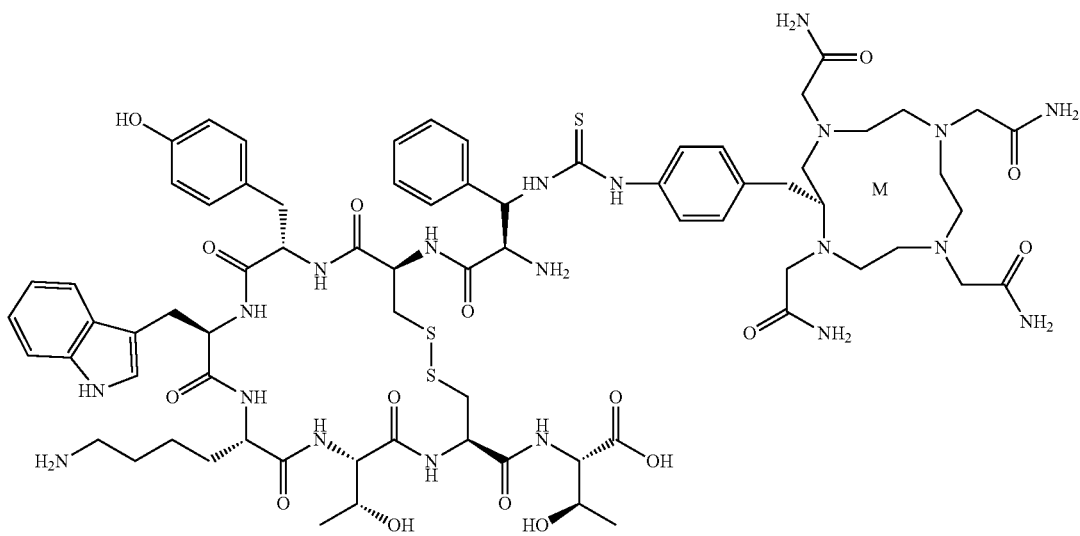

where M is the radioisotope.

The radioisotope comprises at least one of an α-emitter, a β-emitter, a γ-emitter, a positron emitter, and combinations thereof. The radioisotope comprises at least one of: $^{212}$Bi, $^{212}$Pb, $^{203}$Pb, and combinations thereof. The chelator has one of the following general formulas:

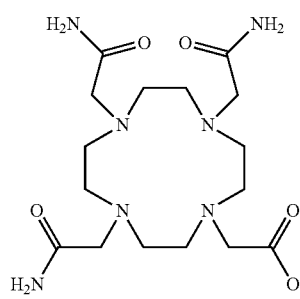
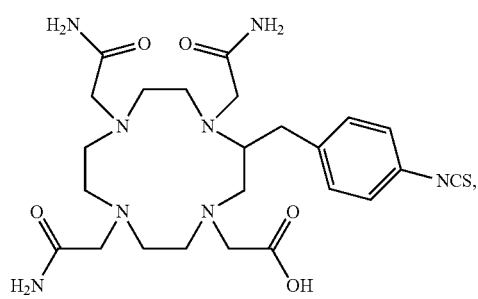
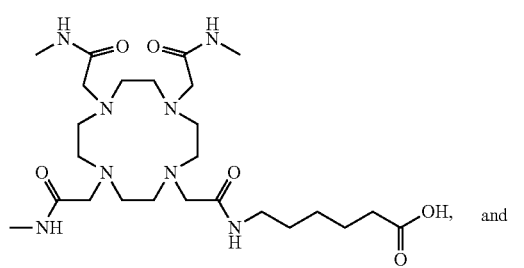
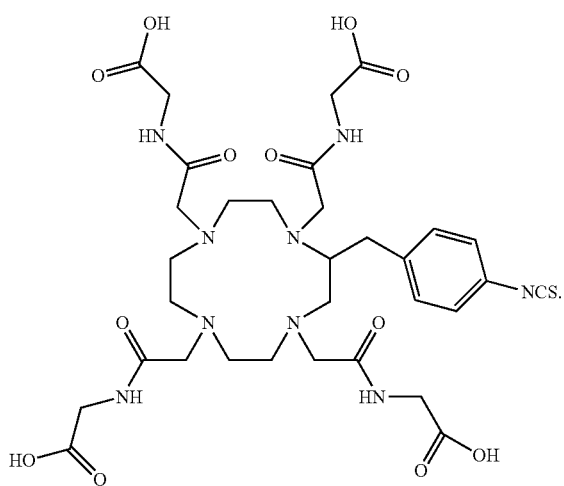
The radioisotope comprises at least one of $^{64}$Cu and $^{67}$Cu. The chelator has one of the following general formulas:
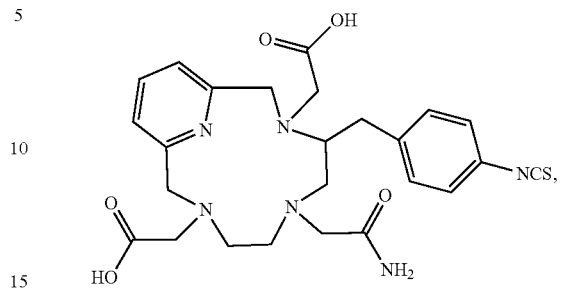
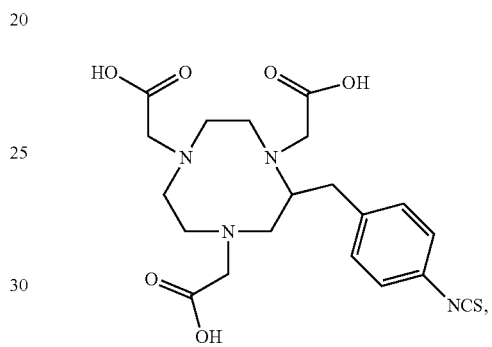
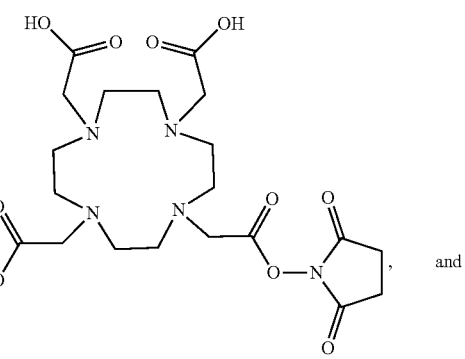
, and
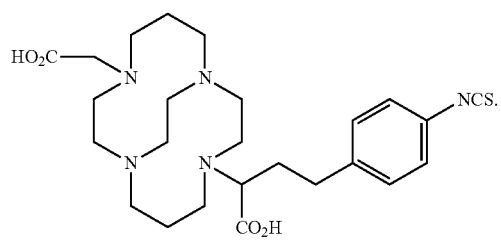

The radioisotope is one selected from the group consisting of: $^{225}$Ac, $^{231}$Am, $^{243}$Am, $^{211}$At, $^{217}$At, $^{247}$Bk, $^{212}$Bi, $^{213}$Bi, $^{248}$Cf, $^{250}$Cf, $^{251}$Cf, $^{240}$Cm, $^{243}$Cm, $^{245}$Cm, $^{154}$Dy, $^{252}$Es, $^{253}$Es, $^{255}$Es, $^{252}$Fm, $^{253}$Fm, $^{221}$Fr, $^{148}$Gd, $^{174}$Hf, $^{258}$Md, $^{144}$Nd, $^{237}$Np, $^{186}$Os, $^{190}$Pt, $^{236}$Pu, $^{238}$Pu, $^{213}$Pa, $^{231}$Pa, $^{223}$Ra, $^{224}$Ra, $^{219}$Rn, $^{146}$Sm, $^{147}$Sm, $^{149}$Tb, $^{227}$Th, $^{229}$Th, $^{230}$U, $^{236}$U and combinations thereof. The chelator comprises 1,4,7,10-tetrakis (carbamoylmethyl)-1,4,7,10-tetraazacyclododecane, or 1,4,7,10-tetraazacyclododecane-1,4,7-tri(carbamoylmethyl)-10-acetic acid. The chelator comprises (2-(4-isothiocyanotobenzyl)-1, 4, 7, 10-tetraaza-1, 4, 7, 10-tetra-(2-carbamonyl methyl)-cyclododecane), S-2-(4-Isothiocyanatobenzyl)-1,4,7,10-tetraaza-1,4,7,10-tetra(2-carbamoylmethyl)cyclododecane, or 2-(4,7,10-tris(2-amino-2-oxoethyl)-3-(4-isothiocyanatobenzyl)-1,4,7,10-tetraazacyclododecan-1-yl)acetic acid. The cancer targeting composition further includes a linker, the targeting moiety chelated to the radioisotope via the linker to the chelator. The linker comprises at least one of a straight chain ($C_1$-$C_6$)alkyl, a branched-chain ($C_1$-$C_6$)alkyl, a polyethylene glycol, and combinations thereof. In an embodiment, the octreotide derivative comprises one of conjugates of octreotate (H-D-Phe-Cys-Phe-D-Trp-Lys-Thr-Cys-Thr-OH, $C_{49}H_{64}N_{10}O_{11}S_2$), conjugates of (Tyr3)-octreotate, octreotide (H$_2$N-D-Phe-Cys-Phe-D-Trp-Lys-Thr-Cys-Thr-ol, $C_{49}H_{66}N_{10}O_{10}S_2$), and combinations thereof. The cancer targeting composition further includes a terminal group selected from the group consisting of: methylcarboxyl, acetamide, alkanes, alkenes, acetic acid, and carboxylamine.

A cancer targeting kit for treatment of cancer cells overexpressing somatostatin receptors is disclosed herein. The cancer targeting kit includes a cancer targeting composition, comprising: a radioisotope; a chelator comprising a nitrogen ring structure, the nitrogen ring structure comprising a derivative selected from the group consisting of a tetraazacyclododecane derivative, a triazacyclononane derivative, and a tetraazabicyclo[6.6.2] hexadecane derivative; and a targeting moiety comprising a somatostatin receptor targeting peptide, the somatostatin receptor targeting peptide comprising an octreotide derivative, the targeting moiety chelated to the radioisotope by the chelator coordinating the radioisotope whereby the cancer cells are targeted for elimination and treated or a product thereof; and a buffer.

The cancer targeting kit includes 25-50 µg of the cancer targeting composition and 0.4M of ammonium acetate. In an embodiment, the buffer comprises an ammonium acetate buffer. The cancer targeting kit further includes an antioxidant is at least one selected from the group consisting of: ascorbic acid, gentisic acid, ethanol, and combinations thereof. The cancer targeting kit further includes a scavenger is one selected from the group consisting of: diethylenetriaminopentaacetic, diethylenetriaminepentaacetic acid, ethylenediaminetetraacetic acid, 1,4,7,10-tetraazacyclododecane-1,4,7,10-tetraacetic acid, and combinations thereof.

A method of targeted treatment of cancer cells overexpressing somatostatin receptors is disclosed herein. The method includes providing a cancer targeting composition which includes or is product of a radioisotope; a chelator comprising a nitrogen ring structure, the nitrogen ring structure comprising a derivative selected from the group consisting of a tetraazacyclododecane derivative, a triazacyclononane derivative, and a tetraazabicyclo[6.6.2] hexadecane derivative; and a targeting moiety comprising a somatostatin receptor targeting peptide, the somatostatin receptor targeting peptide comprising an octreotide derivative, the targeting moiety chelated to the radioisotope by the chelator whereby the cancer cells are be targeted for elimination; and administering the cancer targeting composition to a patient having the cancer cells.

The method further includes binding the targeting moiety to the cancer cells. The method further includes uptake of the cancer targeting composition by the cancer cells. The method further includes decaying the radioisotope by emitting a beta particle. The decaying comprises decaying 212Pb to 212Bi by emitting the beta particle and decaying the 212Bi to 208Ti by emitting an alpha particle. In an embodiment of the method, the decaying occurs within or on a surface of the cancer cells. The method further includes killing the cancer cells with the alpha particle. The method further includes eliminating the cancer targeting composition from the patient.

The composition may have the following chemical structure:

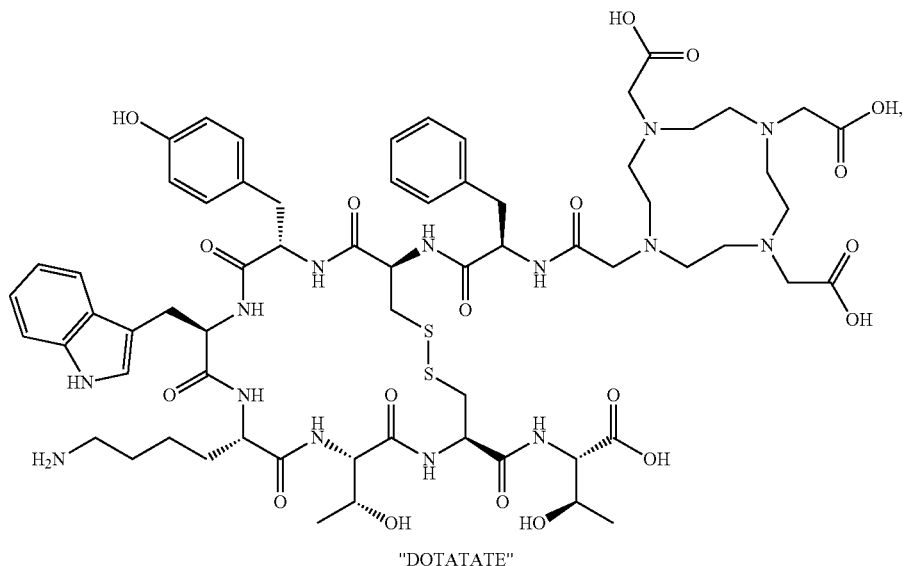

"DOTATATE"

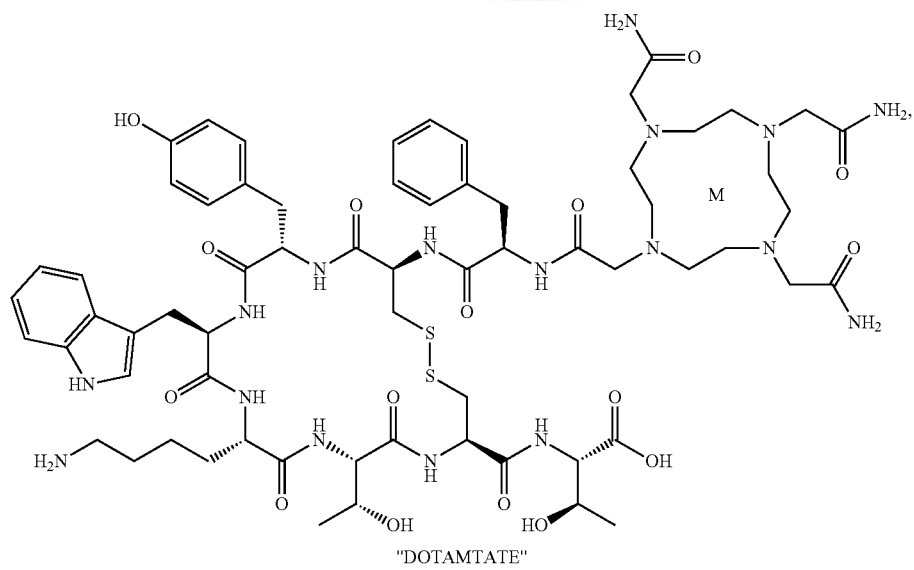
"DOTAMTATE"
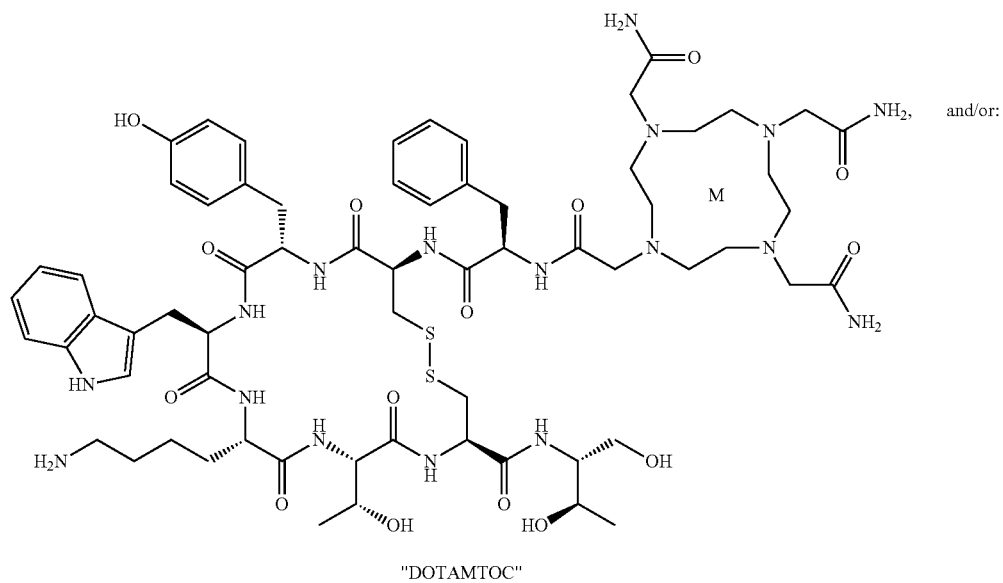
"DOTAMTOC"
and/or:
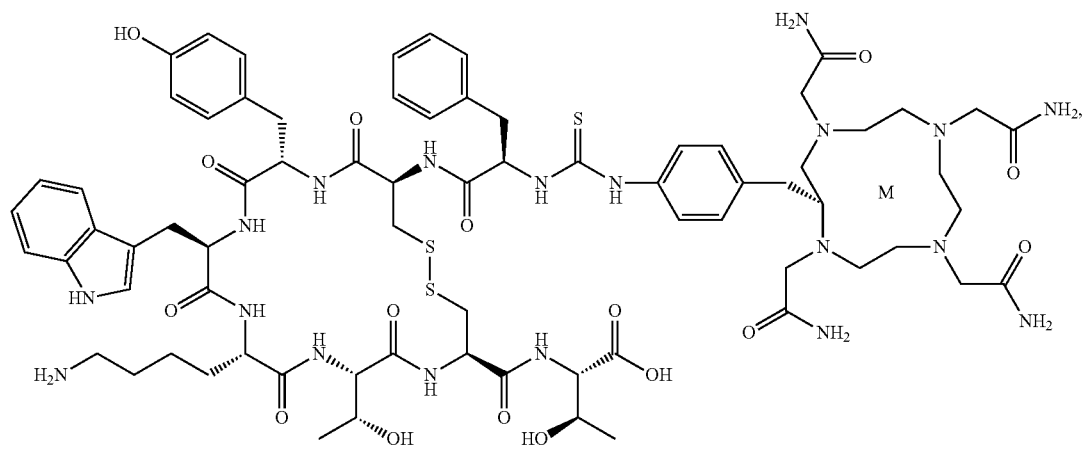
"TCMCTATE"

where M is the radioisotope. The composition may have the following chemical structure ((4R,7S,10S,13R,16S,19R)-13-((1H-indol-3-yl)methyl)-10-(4-aminobutyl)-16-(4-hydroxybenzyl)-7-((R)-1-hydroxyethyl)-6,9,12,15,18-pentaoxo-19-((R)-3-phenyl-2-(2-(4,7,10-tris(2-amino-2-oxoethyl)-1,4,7,10-tetraazacyclododecan-1-yl)acetamido)propanamido)-1,2-dithia-5,8,11,14,17-pentaazacycloicosane-4-carbonyl)-L-threonine chelated to M; 2,2',2''-(10-(2-(((R)-1-(((4R,7S,10S,13R,16S,19R)-13-((1H-indol-3-yl)methyl)-10-(4-aminobutyl)-4-(((2R,3R)-1,3-dihydroxybutan-2-yl)carbamoyl)-16-(4-hydroxybenzyl)-7-((R)-1-hydroxyethyl)-6,9,12,15,18-pentaoxo-1,2-dithia-5,8,11,14,17-pentaazacycloicosan-19-yl)amino)-1-oxo-3-phenylpropan-2-yl)amino)-2-oxoethyl)-1,4,7,10-tetraazacyclododecane-1,4,7-triyl)triacetamide chelated to M; or ((4R,7S,10S,13R,16S,19R)-13-((1H-indol-3-yl)methyl)-10-(4-aminobutyl)-16-(4-hydroxybenzyl)-7-((R)-1-hydroxyethyl)-6,9,12,15,18-pentaoxo-19-((R)-3-phenyl-2-(3-(4-(((S)-1,4,7,10-tetrakis(2-amino-2-oxoethyl)-1,4,7,10-tetraazacyclododecan-2-yl)methyl)phenyl) thioureido)propanamido)-1,2-dithia-5,8,11,14,17-pentaazacycloicosane-4-carbonyl)-L-threonine chelated to M, respectively, where M is the radioisotope.

Within the context of the present invention, the term "radioisotope" as used herein includes ions thereof. Thus, the skilled person in the art understand that, for instance, the terms lead, Pb, $^{212}$Pb or $^{203}$Pb are intended to encompass the ionic form of the radioisotope element.

The radioisotope may comprise an α-emitter, a β-emitter, a γ-emitter, and/or a positron emitter. The radioisotope may comprise $^{212}$Bi, $^{212}$Pb, $^{203}$Pb, $^{64}$Cu, $^{67}$Cu, $^{225}$Ac, $^{231}$Am, $^{243}$Am, $^{211}$At, $^{217}$At, $^{247}$Bk, $^{212}$Bi, $^{213}$Bi, $^{248}$Cf, $^{250}$Cf, $^{251}$Cf, $^{240}$Cm, $^{243}$Cm, $^{245}$Cm, $^{154}$Dy, $^{252}$Es, $^{253}$Es, $^{255}$Es, $^{252}$Fm, $^{253}$Fm, $^{221}$Fr, $^{148}$Gd, $^{174}$Hf, $^{258}$Md, $^{144}$Nd, $^{237}$Np, $^{186}$Os, $^{190}$Pt, $^{236}$Pu, $^{238}$Pu, $^{213}$Pa, $^{231}$Pa, $^{223}$Ra, $^{224}$Ra, $^{219}$Rn, $^{146}$Sm, $^{147}$Sm, $^{149}$Tb, $^{227}$Th, $^{229}$Th, $^{230}$U, and/or $^{236}$U.

The chelator may have one of the following general formulas:

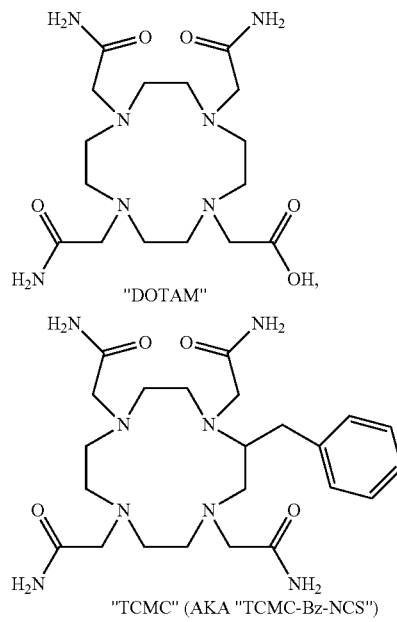

"DOTAM"

"TCMC" (AKA "TCMC-Bz-NCS")

"TCMC-monoacid"

"NOTA"

and/or

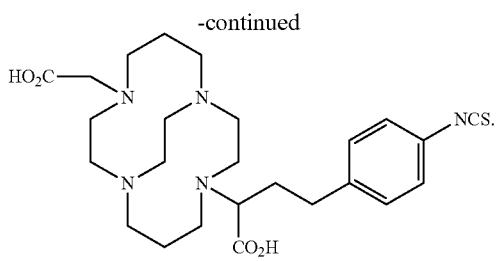

The chelator can comprise 2-(4,7,10-tris(2-amino-2-oxoethyl)-1,4,7,10-tetraazacyclododecan-1-yl)acetic acid; 2,2',2'',2'''-(2-(4-isothiocyanatobenzyl)-1,4,7,10-tetraazacyclododecane-1,4,7,10-tetrayl)tetraacetamide; 2-(4,7,10-tris(2-amino-2-oxoethyl)-3-(4-isothiocyanatobenzyl)-1,4,7,10-tetraazacyclododecan-1-yl)acetic acid; 6-(2-(4,7,10-tris(2-(methylamino)-2-oxoethyl)-1,4,7,10-tetraazacyclododecan-1-yl)acetamido)hexanoic acid; 2,2',2'',2'''-((2,2',2'',2'''-(2-(4-isothiocyanatobenzyl)-1,4,7,10-tetraazacyclododecane-1,4,7,10-tetrayl)tetrakis(acetyl)) tetrakis(azanediyl))tetraacetic acid; 2,2',2''-(4-(4-isothiocyanatobenzyl)-3,6,9-triaza-1(2,6)-pyridinacyclodecaphane-3,6,9-triyl)triacetic acid; 2,2',2''-(2-(4-isothiocyanatobenzyl)-1,4,7-triazonane-1,4,7-triyl) triacetic acid; 2,2',2''-(10-(2-((2,5-dioxopyrrolidin-1-yl)oxy)-2-oxoethyl)-1,4,7,10-tetraazacyclododecane-1,4,7-triyl)triacetic acid; and 2-(11-(carboxymethyl)-1,4,8,11-tetraazabicyclo[6.6.2]hexadecan-4-yl)-4-(4-isothiocyanatophenyl)butanoic acid, respectively. The chelator can comprise DOTAM (1,4,7,10-Tetrakis (carbamoylmethyl)-1,4,7,10-tetraazacyclododecane), and/or TCMC (2-(4-isothiocyanotobenzyl)-1, 4, 7, 10-tetraaza-1, 4, 7, 10-tetra-(2-carbamonyl methyl)-cyclododecane).

The cancer targeting composition may also comprise a linker. The targeting moiety may be chelated to the radioisotope via the linker. The linker may comprise a straight chain C1-C6 alkyl, a branched-chain C1-C6 alkyl, and/or polyethylene glycol.

The octreotide derivative may comprise octreotate (H-D-Phe-Cys-Phe-D-Trp-Lys-Thr-Cys-Thr-OH, $C_{49}H_{64}N_{10}O_{11}S_2$), conjugates of (Tyr3)-octreotate, octreotide (H$_2$N-D-Phe-Cys-Phe-D-Trp-Lys-Thr-Cys-Thr-ol, and/or $C_{49}H_{66}N_{10}O_{10}S_2$). The cancer targeting composition may also comprise terminal groups. The terminal groups may be methylcarboxyl, acetamide, alkanes, alkenes, acetic acid, and/or carboxylamine. Unless otherwise noted, the term "octreotide derivative" refers to an octreotide having one or more terminal groups selected from the group consisting of methylcarboxyl, acetamide, alkanes, alkenes, acetic acid, and/or carboxylamine.

In another aspect, the disclosure relates to a cancer targeting kit for treatment of cancer cells overexpressing somatostatin receptors. The kit comprises a cancer targeting composition for treatment of cancer cells overexpressing somatostatin receptors and a buffer. The composition comprises a radioisotope, a chelator, and a targeting moiety. The chelator comprises a nitrogen ring structure. The nitrogen ring structure comprises a derivative selected from the group consisting of a tetraazacyclododecane derivative, a triazacyclononane derivative, and a tetraazabicyclo[6.6.2] hexadecane derivative, including, but not limited to, 2-(4,7,10-tris(2-amino-2-oxoethyl)-1,4,7,10-tetraazacyclododecan-1-yl)acetic acid; 2,2',2'',2'''-(2-(4-isothiocyanatobenzyl)-1,4,7,10-tetraazacyclododecane-1,4,7,10-tetrayl)tetraacetamide; 2-(4,7,10-tris(2-amino-2-oxoethyl)-3-(4-isothiocyanatobenzyl)-1,4,7,10-tetraazacyclododecan-1-yl)acetic acid; 6-(2-(4,7,10-tris(2-(methylamino)-2-oxoethyl)-1,4,7,10-tetraazacyclododecan-1-yl)acetamido)hexanoic acid; 2,2',2'',2'''-((2,2',2'',2'''-(2-(4-isothiocyanatobenzyl)-1,4,7,10-tetraazacyclododecane-1,4,7,10-tetrayl)tetrakis(acetyl)) tetrakis(azanediyl))tetraacetic acid; 2,2',2''-(4-(4-isothiocyanatobenzyl)-3,6,9-triaza-1(2,6)-pyridinacyclodecaphane-3,6,9-triyl)triacetic acid; 2,2',2''-(2-(4-isothiocyanatobenzyl)-1,4,7-triazonane-1,4,7-triyl)triacetic acid; 2,2',2''-(10-(2-((2,5-dioxopyrrolidin-1-yl)oxy)-2-oxoethyl)-1,4,7,10-tetraazacyclododecane-1,4,7-triyl)triacetic acid; and 2-(11-(carboxymethyl)-1,4,8,11-tetraazabicyclo[6.6.2]hexadecan-4-yl)-4-(4-isothiocyanatophenyl)butanoic acid, DOTAM (1,4,7,10-Tetrakis (carbamoylmethyl)-1,4,7,10-tetraazacyclododecane), and/or TCMC (2-(4-isothiocyanotobenzyl)-1, 4, 7, 10-tetraaza-1, 4, 7, 10-tetra-(2-carbamonyl methyl)-cyclododecane).

The targeting moiety comprises a somatostatin receptor targeting peptide. The somatostatin receptor targeting peptide comprises an octreotide derivative, and is conjugated to the chelator coordinating the radioisotope whereby the cancer cells are targeted for elimination and treated. The kit may also include an antioxidant and/or a scavenger. The cancer targeting composition may comprise from about 25 to about 50 μg of the cancer targeting composition and about 0.4M of ammonium acetate.

In another aspect, the disclosure relates to a method of targeted treatment of cancer cells overexpressing somatostatin receptors. The method involves providing a cancer targeting composition and administering the cancer targeting composition to a patient having the cancer cells. The composition comprises a radioisotope, a chelator, and a targeting moiety. The chelator comprises a nitrogen ring structure. The nitrogen ring structure comprises a derivative selected from the group consisting of a tetraazacyclododecane derivative, a triazacyclononane derivative, and a tetraazabicyclo [6.6.2] hexadecane derivative. Unless otherwise noted, the term "derivative" used in the context of the nitrogen ring refers to a nitrogen ring structure having one or more terminal groups selected from the group consisting of $CH_2C(=O)-OH$ and $CH_2C(=O)-NH_2$. For example, a tetraazacyclododecane derivative, a triazacyclononane derivative, and a tetraazabicyclo[6.6.2] hexadecane derivative, refer to a tetraazacyclododecane, triazacyclononane, and a tetraazabicyclo[6.6.2] hexadecane wherein at least one of the nitrogen has a terminal groups selected from the group consisting of $CH_2C(=O)-OH$ and $CH_2C(=O)-NH_2$ The targeting moiety comprises a somatostatin receptor targeting peptide. The somatostatin receptor targeting peptide comprises an octreotide derivative, and is conjugated to the chelator coordinating the radioisotope whereby the cancer cells are targeted for elimination and treated.

This summary also includes the features as depicted in the drawings.

BRIEF DESCRIPTION OF THE DRAWINGS

A more particular description of the disclosure may be had by reference to embodiments illustrated in the appended drawings. It is to be noted, however, that the appended drawings illustrate examples and are, therefore, not to be considered limiting of its scope. The figures are not necessarily to scale and certain features, and certain views of the figures may be shown exaggerated in scale or in schematic in the interest of clarity and conciseness.

FIGS. 2A1-2A4 and 2B1-2B4 are example chemical structures of chelators of the cancer targeting composition.

FIGS. 3A and 3B are example chemical structures of functional groups of the cancer targeting composition.

FIGS. 4A and 4B are example chemical structures of linkers of the cancer targeting composition.

FIG. 28A: Saline only, FIG. 28B: 3×10 µCi-2w; and FIG. 28C 3×10 µCi-3w.

DETAILED DESCRIPTION

Figure 1A:
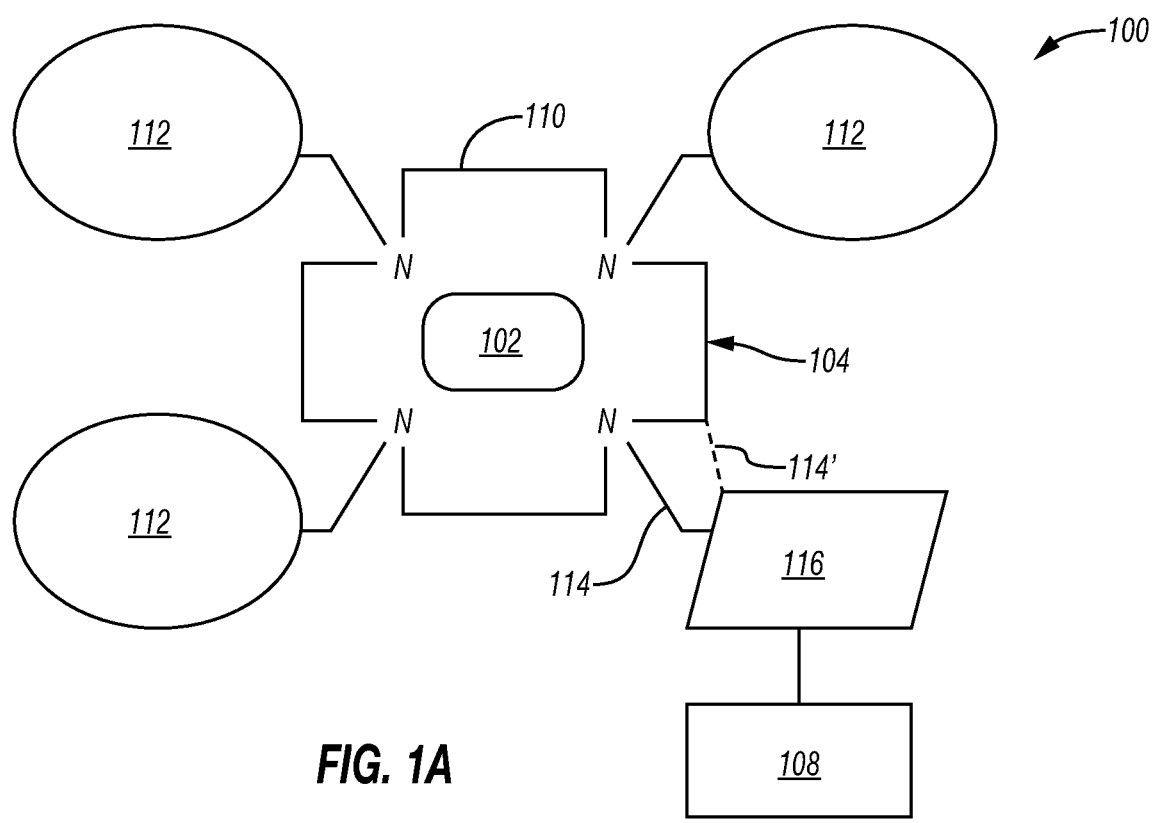
FIGS. 1A and 1B are schematic diagrams depicting various configurations of a cancer targeting composition comprising somatostatin receptor targeting chelator-conjugates.

The description that follows includes exemplary apparatus, methods, techniques, and/or instruction sequences that embody techniques of the present subject matter. However, it is understood that the described embodiments may be practiced without these specific details.

A cancer targeting composition for treating cancer cells overexpressing somatostatin receptors is disclosed herein. The cancer targeting composition includes a molecule of Formula (I) or a pharmaceutically acceptable salt thereof:

$$M\text{-Ch-}L_1\text{-Tm,} \quad \text{Formula (I)}$$

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

Ch is a chelator having a structure selected from the group consisting of:

Formula (II), Formula (III), Formula (IV), and Formula (V), wherein

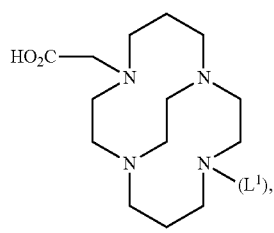

Formula (II)

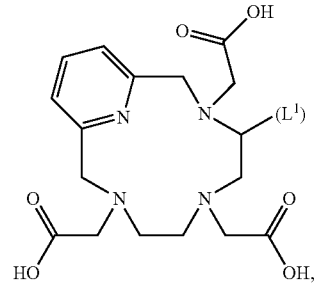

Formula (III)

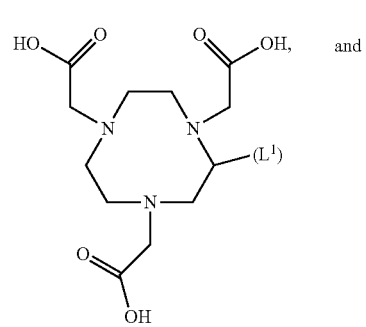

Formula (IV)

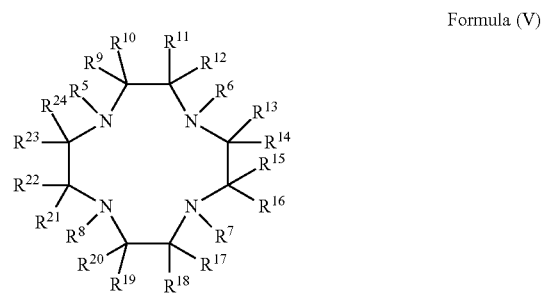

Formula (V)

wherein $R^5$, $R^6$, and $R^8$ are each independently selected from the group consisting of H, D, F, Cl, $(C_1\text{-}C_6)$alkyl, $(C_1\text{-}C_6)$alkyl-$C(=O)$—$OR^{25}$, and $(C_1\text{-}C_6)$alkyl-$C(=O)$—$N(-R^{25})$—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1\text{-}C_6)$alkyl;

$R^7$ is independently selected from the group consisting of H, D, F, Cl, $(C_1\text{-}C_6)$alkyl, $(C_1\text{-}C_6)$alkyl-$C(=O)$—$N(-R^{25})$—$R^{26}$, and Li;

$R^{13}$ and $R^{14}$ are each independently selected from the group consisting of H, D, F, Cl, $(C_1\text{-}C_6)$alkyl, and $L^1$;

$R^{25}$ and $R^{26}$ are each independently selected from the group consisting of H, D, $(C_1\text{-}C_6)$alkyl, and $(C_1\text{-}C_6)$alkyl-$C(=O)$—OH;

$L^1$ is independently selected from a group consisting of, and $(C_1\text{-}C_6)$alkyl-$C(=O)$—NH—$(C_1\text{-}C_6)$alkyl-$C(=O)$—NH, $(C_1\text{-}C_6)$alkyl-$(C_6H_4)$—NH—$C(=S)$—NH, $C(-CO_2H)$—$(C_1\text{-}C_6)$alkyl-$(C_6H_4)$—NH—$C(=S)$—NH, $(C_1\text{-}C_6)$alkyl-$C(=O)$—NH, $(C_1\text{-}C_6)$alkyl-$C(=O)$—$(O$—$CH_2$—$CH_2)_{1-20}$—$C(=O)$—NH; and Tm has a structure of Formula (VI),

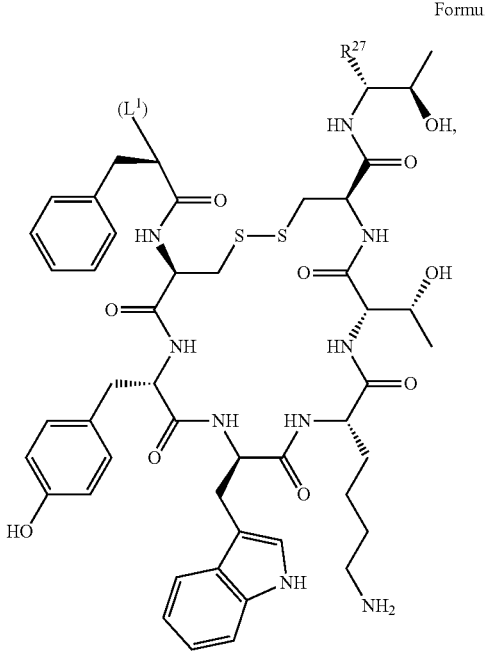

Formula (VI)

wherein $R^{27}$ is independently selected from the group consisting of $CH_2$—OH and C(=O)—OH; and provided that only one of $R^7$, $R^{13}$, or $R^{14}$ is $L^1$. Unless otherwise noted, the use of $L^1$ in parenthesis indicates that that $L^1$ is not formally part of, for example, Tm, but is being shown as part of Tm to indicate the relevant points of attachment.

The cancer targeting composition may have one, two, or three of $R^5$, $R^6$, and $R^8$ is $(C_1-C_6)$alkyl-C(=O)—N(—$R^{25}$)—$R^{26}$. M may be selected from the group consisting of $^{212}$Pb, $^{203}$Pb, $^{64}$Cu, $^{67}$Cu, $^{212}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho. M may be independently selected from the group consisting of $^{212}$Pb, $^{203}$Pb, $^{64}$Cu, and $^{67}$Cu. M may be selected from the group consisting of $^{212}$Pb, $^{203}$Pb, $^{64}$Cu, $^{67}$Cu, and $^{212}$Bi; and Ch may have a structure of Formula (V); and $R^{27}$ is $CH_2$—OH. M may also be selected from the group consisting of $^{212}$Pb, $^{203}$Pb, $^{64}$Cu, $^{67}$Cu, $^{212}$Bi, and $^{213}$Bi; and Ch may have a structure of Formula (V), and $R^{27}$ is C(=O)—OH. The molecule of Formula (I) is produced by reacting at least one compound with a chelator, wherein the chelator is selected from the group consisting of:

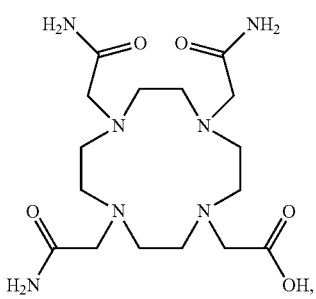

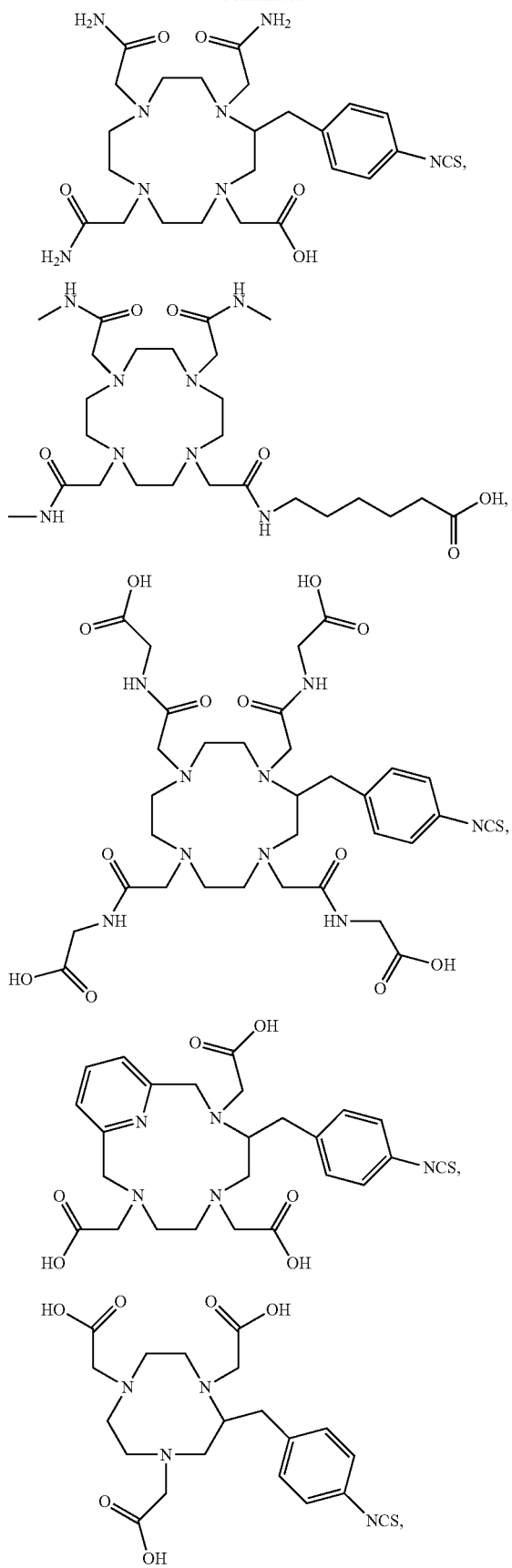

-continued

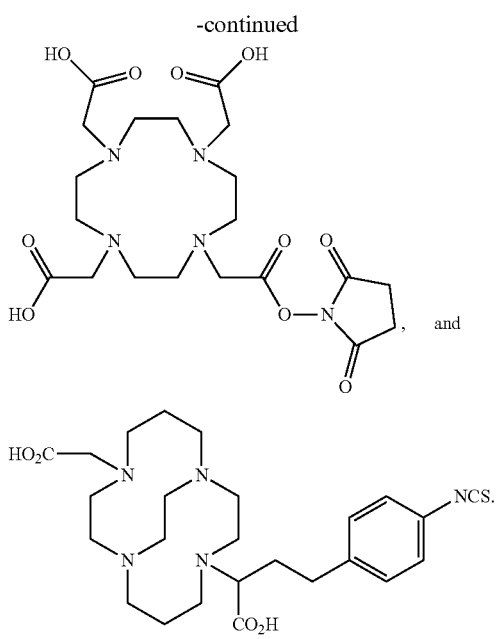

, and

The cancer targeting composition may have a structure represented by Formula (VII) or a pharmaceutically acceptable salt thereof:

Formula (VII)

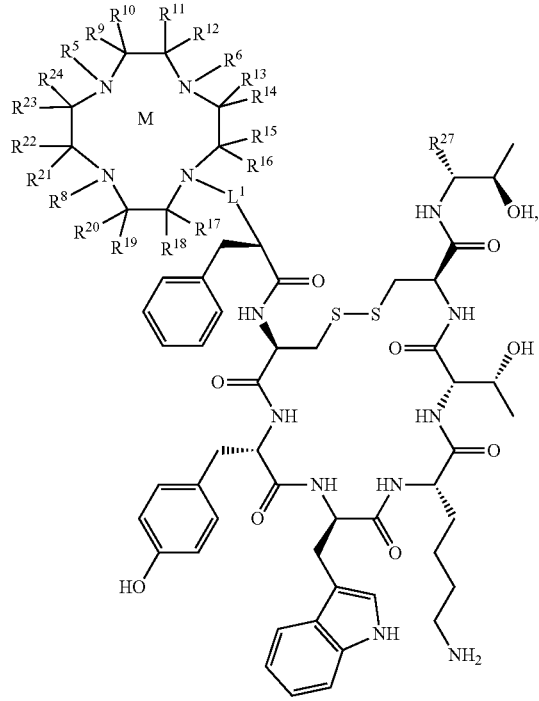

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

$R^5$, $R^6$, and $R^8$ are each independently selected from the group consisting of H, D, F, Cl, $(C_1-C_6)$alkyl, $(C_1-C_6)$alkyl-C(=O)—OR$^{25}$, and $(C_1-C_6)$alkyl-C(=O)—N(—R$^{25}$)—R$^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1-C_6)$alkyl;

$R^{13}$ and $R^{14}$ are each independently selected from the group consisting of H, D, F, Cl, and $(C_1-C_6)$alkyl;

$R^{25}$ and $R^{26}$ are each independently selected from the group consisting of H, D, $(C_1-C_6)$alkyl, and $(C_1-C_6)$alkyl-C(=O)—OH;

$L^1$ is independently selected from a group consisting of, and $(C_1-C_6)$alkyl-C(=O)—NH—$(C_1-C_6)$alkyl-C(=O)—NH, $(C_1-C_6)$alkyl-$(C_6H_4)$—NH—C(=S)—NH, C(—CO$_2$H)—$(C_1-C_6)$alkyl-$(C_6H_4)$—NH—C(=S)—NH, $(C_1-C_6)$alkyl-C(=O)—NH, and $(C_1-C_6)$alkyl-C(=O)—(O—CH$_2$—CH$_2$)$_{1-20}$—C(=O)—NH; and wherein $R^{27}$ is independently selected from the group consisting of CH$_2$—OH and C(=O)—OH.

The cancer targeting composition may have a structure represented by Formula (VIII) or a pharmaceutically acceptable salt thereof:

Formula (VIII)

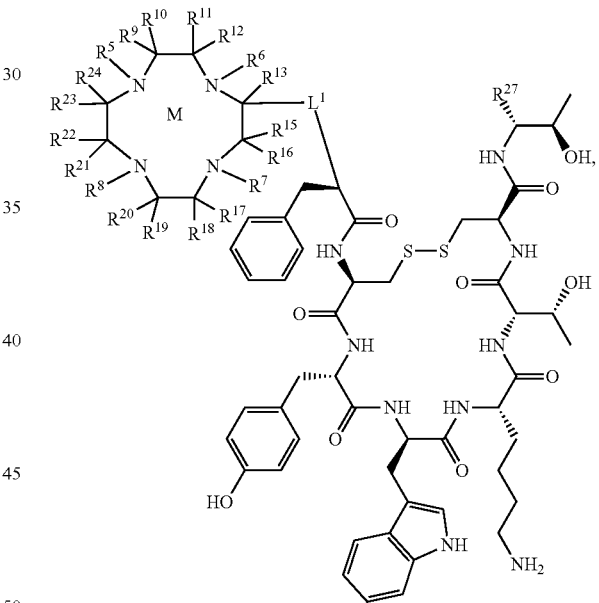

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

$R^5$, $R^6$, and $R^8$ are each independently selected from the group consisting of H, D, F, Cl, $(C_1-C_6)$alkyl, $(C_1-C_6)$alkyl-C(=O)—OR$^{25}$, and $(C_1-C_6)$alkyl-C(=O)—N(—R$^{25}$)—R$^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1-C_6)$alkyl;

$R^7$ is independently selected from the group consisting of H, D, F, Cl, $(C_1-C_6)$alkyl, and $(C_1-C_6)$alkyl-C(=O)—N(—R$^{25}$)—R$^{26}$;

$R^{13}$ is independently selected from the group consisting of H, D, F, Cl, and $(C_1-C_6)$alkyl;

$R^{25}$ and $R^{26}$ are each independently selected from the group consisting of H, D, $(C_1-C_6)$alkyl, and $(C_1-C_6)$alkyl-C(=O)—OH;

$L^1$ is $(C_1-C_6)$alkyl-$(C_6H_4)$—NH—C(=S)—NH; and wherein $R^{27}$ is independently selected from the group consisting of $CH_2$—OH and C(=O)—OH.

The cancer targeting composition may have a structure of Formula (IX) or a pharmaceutically acceptable salt thereof:

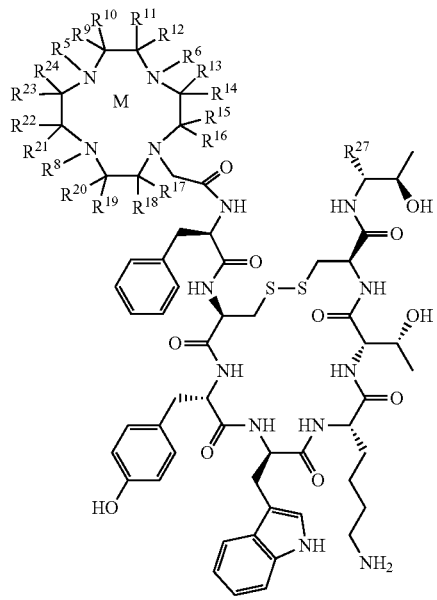

Formula (IX)

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

$R^5$, $R^6$, and $R^8$ are each independently selected from the group consisting of H, D, F, Cl, $(C_1-C_6)$alkyl, $(C_1-C_6)$alkyl-C(=O)—OR$^{25}$, and $(C_1-C_6)$alkyl-C(=O)—N(—R$^{25}$)—R$^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1-C_6)$alkyl;

$R^{13}$ and $R^{14}$ are each independently selected from the group consisting of H, D, F, Cl, and $(C_1-C_6)$alkyl;

$R^{25}$ and $R^{26}$ are each independently selected from the group consisting of H, D, $(C_1-C_6)$alkyl, and $(C_1-C_6)$alkyl-C(=O)—OH; and wherein $R^{27}$ is independently selected from the group consisting of $CH_2$—OH and C(=O)—OH.

The cancer targeting composition may have a structure of Formula (X) or a pharmaceutically acceptable salt thereof:

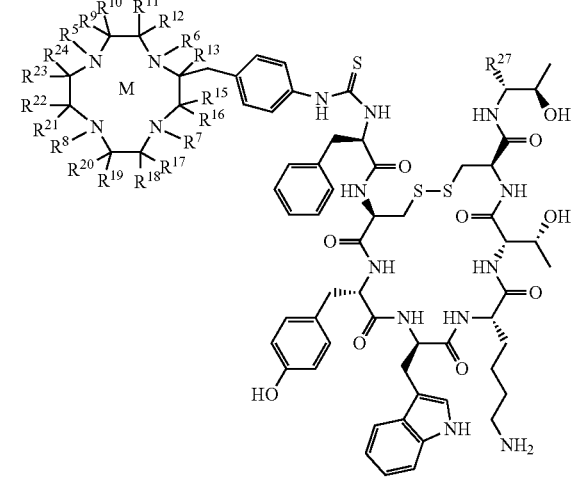

Formula (X)

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy 148Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

$R^5$, $R^6$, and $R^8$ are each independently selected from the group consisting of H, D, F, Cl, $(C_1-C_6)$alkyl, $(C_1-C_6)$alkyl-C(=O)—OR$^{25}$, and $(C_1-C_6)$alkyl-C(=O)—N(—R$^{25}$)—R$^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1-C_6)$alkyl;

$R^7$ is independently selected from the group consisting of H, D, F, Cl, $(C_1-C_6)$alkyl, and $(C_1-C_6)$alkyl-C(=O)—N(—R$^{25}$)—R$^{26}$;

$R^{13}$ is independently selected from the group consisting of H, D, F, Cl, and $(C_1-C_6)$alkyl;

$R^{25}$ and $R^{26}$ are each independently selected from the group consisting of H, D, and $(C_1-C_6)$alkyl, and $(C_1-C_6)$alkyl-C(=O)—OH; and wherein $R^{27}$ is independently selected from the group consisting of $CH_2$—OH and C(=O)—OH.

The composition may include a molecule of Formula (I) or a pharmaceutically acceptable salt thereof:

M-Ch-L$_1$-Tm,      Formula (I)

wherein

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

Ch is a chelator having a structure of Formula (V), wherein

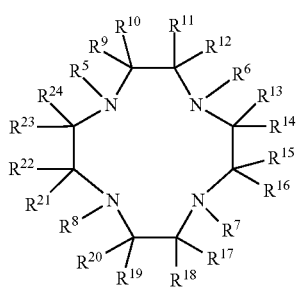

Formula (V)

wherein $R^5$, $R^6$, and $R^8$ are each independently selected from the group consisting of H, D, F, Cl, $(C_1\text{-}C_6)$alkyl, $(C_1\text{-}C_6)$alkyl-C(=O)—$OR^{25}$, and $(C_1\text{-}C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1\text{-}C_6)$alkyl;

$R^7$ is independently selected from the group consisting of H, D, F, Cl, $(C_1\text{-}C_6)$alkyl, $(C_1\text{-}C_6)$alkyl-C(=O)—N(—$R^{25}$)—$R^{26}$, and $L_1$;

$R^{13}$ and $R^{14}$ are each independently selected from the group consisting of H, D, F, Cl, $(C_1\text{-}C_6)$alkyl, and $L^1$;

$R^{25}$ and $R^{26}$ are each independently selected from the group consisting of H, D, $(C_1\text{-}C_6)$alkyl, and $(C_1\text{-}C_6)$alkyl-C(=O)—OH;

$L^1$ is independently selected from a group consisting of $(C_1\text{-}C_6)$alkyl-C(=O)—NH—$(C_1\text{-}C_6)$alkyl-C(=O)—NH, $(C_1\text{-}C_6)$alkyl-$(C_6H_4)$—NH—C(=S)—NH, C(—$CO_2H$)—$(C_1\text{-}C_6)$alkyl-$(C_6H_4)$—NH—C(=S)—NH, $(C_1\text{-}C_6)$alkyl-C(=O)—NH, $(C_1\text{-}C_6)$alkyl-C(=O)—(O—$CH_2$—$CH_2)_{1\text{-}20}$—C(=O)—NH; and Tm has a structure of Formula (VI),

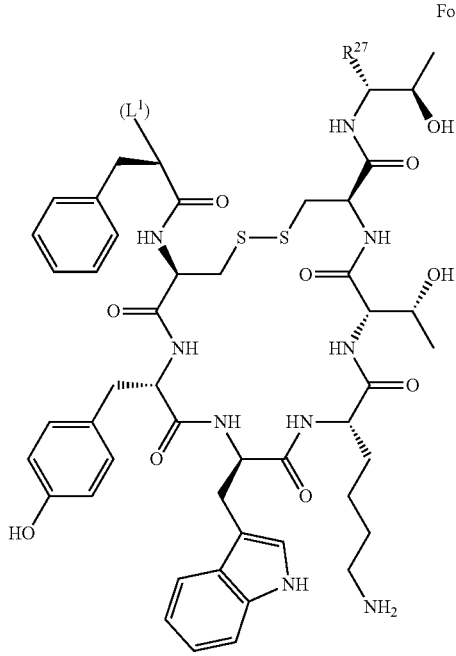

Formula (VI)

wherein $R^{27}$ is $CH_2$—OH; and provided that only one of $R^7$, $R^{13}$, or $R^{14}$ is $L^1$.

A cancer targeting kit for treatment of cancer cells overexpressing somatostatin receptors is disclosed herein. The cancer targeting kit may include the cancer targeting composition of as disclosed herein, and at least one of a pharmaceutically acceptable buffer, an antioxidant, and a scavenger. The cancer targeting kit may include 25-50 µg of the cancer targeting composition and 0.4M ammonium acetate buffer. The cancer targeting kit may include an ammonium acetate buffer. In an embodiment, the buffer comprises an ammonium acetate buffer. The antioxidant may include ascorbic acid, gentisic acid, ethanol, or combinations thereof. The scavenger may be one selected from the group consisting of: diethylenetriaminopentaacetic; ethylene diamine tetraacetic acid; 1,4,7,10-tetraazacyclododecane-1,4,7,10-tetraacetic; and combinations thereof.

A pharmaceutical formulation is disclosed herein. The pharmaceutical formulation may include the cancer targeting composition as disclosed herein and a pharmaceutically acceptable buffer. A cancer targeting composition as disclosed herein for use as a medicine for treating cancerous cells overexpressing somatostatin receptors is disclosed.

A method of administering a cancer targeting composition for treating cancer cells overexpressing somatostatin receptors to a subject in need thereof is disclosed herein. The method may include administering a therapeutically effective dosage of a cancer targeting composition, the cancer targeting composition comprising a molecule of Formula (I) or a pharmaceutically acceptable salt thereof:

wherein M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In, $^{153}$Gd, $^{153}$Sm, and $^{166}$Ho;

Ch is a chelator having a structure selected from the group consisting of:

Formula (II), Formula (III), Formula (IV), and Formula (V), wherein

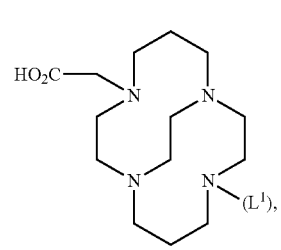

Formula (II)

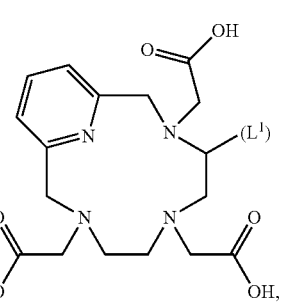

Formula (III)

Formula (IV)

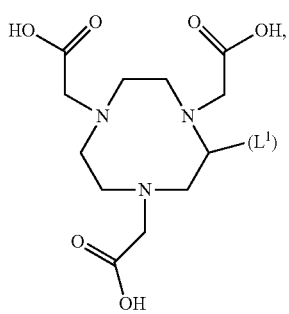

Formula (V)

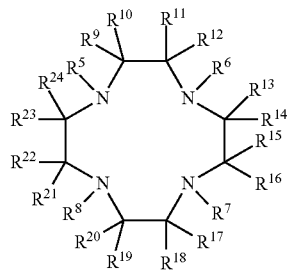

wherein $R^5$, $R^6$, and $R^8$ are each independently selected from the group consisting of H, D, F, Cl, $(C_1\text{-}C_6)$alkyl, $(C_1\text{-}C_6)$alkyl-$C(=O)$—$OR^{25}$, and $(C_1\text{-}C_6)$alkyl-$C(=O)$—$N(-R^{25})$—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and $(C_1\text{-}C_6)$alkyl;

$R^7$ is independently selected from the group consisting of H, D, F, Cl, $(C_1\text{-}C_6)$alkyl, $(C_1\text{-}C_6)$alkyl-$C(=O)$—$N(-R^{25})$—$R^{26}$, and $L_1$;

$R^{13}$ and $R^{14}$ are each independently selected from the group consisting of H, D, F, Cl, $(C_1\text{-}C_6)$alkyl, and $L^1$;

$R^{25}$ and $R^{26}$ are each independently selected from the group consisting of H, D, and $(C_1\text{-}C_6)$alkyl, and $(C_1\text{-}C_6)$alkyl-$C(=O)$—OH;

$L^1$ is independently selected from a group consisting of, and $(C_1\text{-}C_6)$alkyl-$C(=O)$—NH—$(C_1\text{-}C_6)$alkyl-$C(=O)$—NH, $(C_1\text{-}C_6)$alkyl-$(C_6H_4)$—NH—$C(=S)$—NH, $C(-CO_2H)$—$(C_1\text{-}C_6)$alkyl-$(C_6H_4)$—NH—$C(=S)$—NH, $(C_1\text{-}C_6)$alkyl-$C(=O)$—NH, and $(C_1\text{-}C_6)$alkyl-$C(=O)$—$(O-CH_2-CH_2)_{1-20}$—$C(=O)$—NH; and Tm has a structure of Formula (VI), Formula (VI)

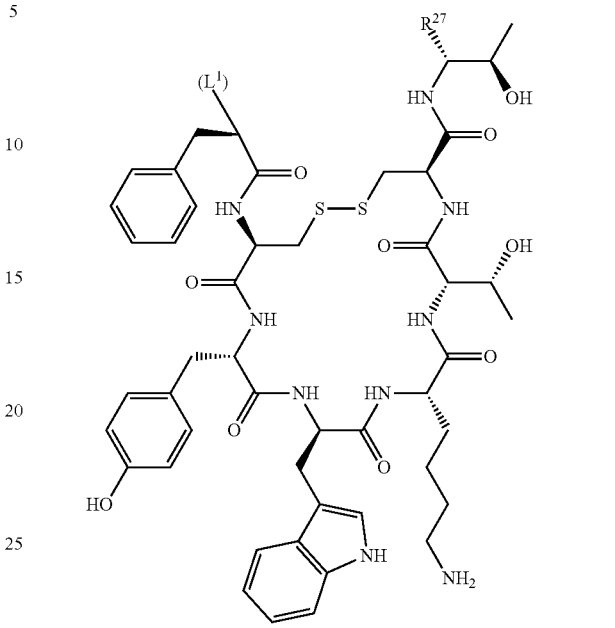

wherein $R^{27}$ is independently selected from the group consisting of $CH_2$—OH and $C(=O)$—OH; and provided that only one of $R^7$, $R^{13}$, or $R^{14}$ is $L^1$.

The cancer may comprise cells overexpressing somatostatin receptors. The cancer may include a cardiac cancer, a lung cancer, a gastrointestinal cancer, genitourinary tract cancer, a liver cancer, a bone cancer, a nervous system cancer, gynecological cancer, a hematologic cancer, or a combination thereof. The subject may be a human, dog, cat, horse, or other mammal. The cancer targeting composition may be administered in combination with at least one anti-cancer compound, wherein the at least one anti-cancer compounds includes Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin, actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim;

pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; or a mixture thereof. The anti-cancer compound may be administered in a therapeutically effective dosage.

A method of administering a cancer targeting composition for treating cancer cells overexpressing somatostatin receptors to a subject in need thereof is disclosed. The method may include administering a therapeutically effective dosage of a molecule of Formula (I), or a pharmaceutically acceptable salt thereof; and at least one anti-cancer compound in a pharmaceutically acceptable carrier, the molecule of Formula (I), wherein M-Ch-L$_1$-Tm,  Formula (I)

M is a radioisotope selected from the group consisting of $^{212}$Pb, $^{203}$Pb, $^{64}$Cu, $^{67}$Cu, $^{212}$Bi, $^{68}$Ga, $^{213}$Bi, $^{225}$Ac, $^{243}$Am, $^{211}$At, $^{217}$At, $^{154}$Dy, $^{148}$Gd, $^{146}$Sm, $^{147}$Sm, $^{149}$Tb, $^{227}$Th, $^{229}$Th, $^{59}$Fe, $^{60}$Cu, $^{61}$Cu, $^{62}$Cu, $^{67}$Ga, $^{86}$Y, $^{111}$In $^{153}$Gd, $^{153}$Sm, and $^{166}$Ho;

Ch is a chelator having a structure selected from the group consisting of:

Formula (II), Formula (III), Formula (IV), and Formula (V), wherein

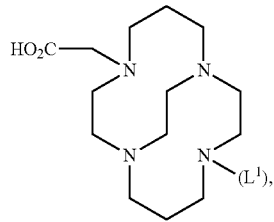

Formula (II)

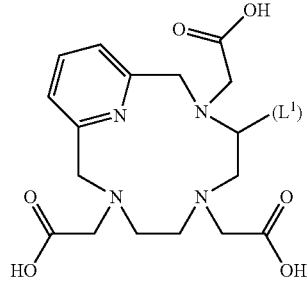

Formula (III)

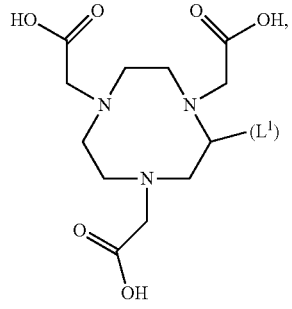

Formula (IV)

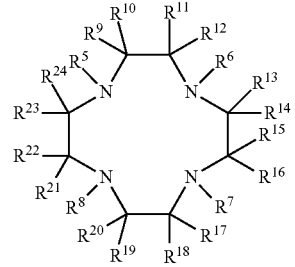

Formula (V)

wherein
$R^5$, $R^6$, and $R^8$ are each independently selected from the group consisting of H, D, F, Cl, (C$_1$-C$_6$)alkyl, (C$_1$-C$_6$)alkyl-C(=O)—OR$^{25}$, and (C$_1$-C$_6$)alkyl-C(=O)—N(—R$^{25}$)—R$^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H, D, F, Cl, and (C$_1$-C$_6$)alkyl;

$R^7$ is independently selected from the group consisting of H, D, F, Cl, (C$_1$-C$_6$)alkyl, (C$_1$-C$_6$)alkyl-C(=O)—N(—R$^{25}$)—R$^{26}$, and L$^1$;

$R^{13}$ and $R^{14}$ are each independently selected from the group consisting of H, D, F, Cl, (C$_1$-C$_6$)alkyl, and L$^1$;

$R^{25}$ and $R^{26}$ are each independently selected from the group consisting of H, D, (C$_1$-C$_6$)alkyl, and (C$_1$-C$_6$)alkyl-C(=O)—OH;

L$^1$ is independently selected from a group consisting of, and (C$_1$-C$_6$)alkyl-C(=O)—NH—(C$_1$-C$_6$)alkyl-C(=O)—NH, (C$_1$-C$_6$)alkyl-(C$_6$H$_4$)—NH—C(=S)—NH, C(—CO$_2$H)—(C$_1$-C$_6$)alkyl-(C$_6$H$_4$)—NH—C(=S)—NH, (C$_1$-C$_6$)alkyl-C(=O)—NH, (C$_1$-C$_6$)alkyl-C(=O)—(O—CH$_2$—CH$_2$)$_{1-20}$—C(=O)—NH; and Tm has a structure of Formula (VI),

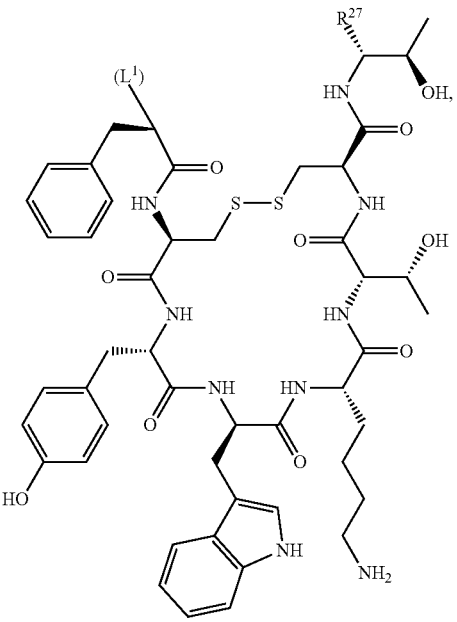

Formula (VI)

wherein $R^{27}$ is independently selected from the group consisting of CH$_2$—OH and C(=O)—OH; and provided that only one of $R^7$, $R^{13}$, or $R^{14}$ is L$^1$.

The at least one anti-cancer compound may include Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin, actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine; gemtuzumab ozogamicin; gleevec (imatinib); goserelin acetate; hydroxyurea; Ibritumomab Tiuxetan; idarubicin; ifosfamide; imatinib mesyflate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; or a combination or a mixture thereof. In an embodiment of the method, the at least one anti-cancer compound is administered in a therapeutically effective dosage.

The Formula (I) or a pharmaceutically acceptable salt thereof may include at least one of $R^5$, $R^6$, and $R^8$ is $(C_1-C_6)$alkyl-C(=O)—O$R^{25}$, wherein $R^{25}$ is H or $(C_1-C_6)$ alkyl.

The Formula (I) or a pharmaceutically acceptable salt thereof may include at least one of $R^5$, $R^6$, and $R^8$ is $(C_1-C_6)$alkyl-C(=O)—N(—$R^{25}$)—$R^{26}$, wherein $R^{25}$ and $R^{26}$ are each independently selected from the group consisting of H and $(C_1-C_6)$alkyl. Preferably, when M is $^{213}$Bi, then $R^5$, $R^6$, and $R^8$ are not $C_1$alkyl-C(=O)—OH. Preferably, when M is $^{213}$Bi, then one, two, or three of $R^5$, $R^6$, and $R^8$ is $CH_2$—C(=O)—$NH_2$.

The Formula (I) or a pharmaceutically acceptable salt thereof may include at least one of $R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H and $(C_1-C_6)$alkyl. The Formula (I) or a pharmaceutically acceptable salt thereof may include at least one of $R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from the group consisting of H and D.

In the Formula (I) or a pharmaceutically acceptable salt thereof, M may be independently selected from the group consisting of $^{212}$Pb, $^{203}$Pb, $^{64}$Cu, and $^{67}$Cu; Ch is Formula (V), wherein $R^5$, $R^6$, and $R^8$ are $(C_1-C_6)$alkyl-C(=O)—N(—$R^{25}$)—$R^{26}$; $R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from H or D; $R^7$ is $L^1$; $L^1$ is $(C_1-C_6)$alkyl-C(=O)—NH; $R^{13}$ and $R^{14}$ are each independently selected from the group consisting of H and D; $R^{25}$ and $R^{26}$ are each independently selected from the group consisting of H and D; Tm has a structure of Formula (VI); and $R^{27}$ is C(=O)—OH.

In the Formula (I) or a pharmaceutically acceptable salt thereof, M may be independently selected from the group consisting of $^{212}$Pb, $^{203}$Pb, $^{64}$Cu, and $^{67}$Cu; Ch is Formula (V), wherein $R^5$, $R^6$, and $R^8$ is $(C_1-C_6)$alkyl-C(=O)—N(—$R^{25}$)—$R^{26}$; $R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently selected from H or D; $R^7$ is $(C_1-C_6)$alkyl-C(=O)—N(—$R^{25}$)—$R^{26}$; $R^{13}$ is independently selected from the group consisting of H and D; $R^{14}$ is $L^1$; $L^1$ is $(C_1-C_6)$alkyl-$(C_6H_4)$—NH—C(=S)—NH; and $R^{27}$ is C(=O)—OH.

The term "alkyl", by itself or as part of another substituent means, unless otherwise stated, a straight, branched (chiral or achiral) or cyclic chain hydrocarbon having the number of carbon atoms designated (e.g. $(C_1-C_6)$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl, including particularly ethyl, methyl and isopropyl. This terms is used in the context of both a substituent and linker group.

Depending on the context, parentheticals used in a formula can convey in a single line information regarding a branch. For example, $(C_1-C_6)$alkyl-C(=O)—OH can also be represented as:

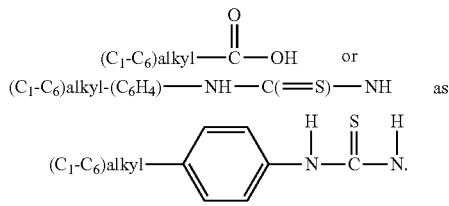

Unless otherwise noted, $(C_6H_4)$ refers to a benzyl group having with 2 substituents, wherein the two substituents can be meta, ortho, or para substituted.

A cancer targeting kit for treatment of cancer cells overexpressing somatostatin receptors is disclosed herein. The cancer targeting kit for treatment of cancer cells overexpressing somatostatin receptors may include: the cancer targeting composition of Formula (I), (VII), (VIII), (IX), and/or (X) or a pharmaceutically acceptable salt thereof, as defined above; and at least one of a pharmaceutically acceptable buffer, an antioxidant, and a scavenger. The cancer targeting kit includes 25-50 μg of the cancer targeting composition and 0.4M ammonium acetate buffer. In the cancer targeting kit, the buffer comprises an ammonium acetate buffer. In the cancer targeting kit, the antioxidant includes ascorbic acid, gentisic acid, ethanol, or combinations thereof. In the cancer targeting kit, the scavenger is selected from the group consisting of: diethylenetriaminopentaacetic; ethylene diamine tetraacetic acid; 1,4,7,10-tetraazacyclododecane-1,4,7,10-tetraacetic; and combinations thereof.

A pharmaceutical formulation is disclosed. The pharmaceutical formulation includes the cancer targeting composition of Formula (I), (VII), (VIII), (IX), and/or (X) or a pharmaceutically acceptable salt thereof, as defined above; and a pharmaceutically acceptable buffer.

A cancer targeting composition for use as a medicine for treating cancerous cells overexpressing somatostatin receptors is disclosed herein. The cancer targeting composition of for use as a medicine for treating cancerous cells overexpressing somatostatin receptors includes a composition having Formula (I), (VII), (VIII), (IX), and/or (X) or a pharmaceutically acceptable salt thereof, as defined above.

A method of a cancer targeting composition for treating cancer cells overexpressing somatostatin receptors to a subject in need thereof is disclosed herein. The method includes administering a dosage of a cancer targeting composition, the cancer targeting composition comprising a molecule of Formula (I), (VII), (VIII), (IX), and/or (X) or a pharmaceutically acceptable salt thereof, as defined above. The cancer may include cells overexpressing somatostatin receptors. The cancer may include a cardiac cancer, a lung cancer, a gastrointestinal cancer, genitourinary tract cancer, a liver cancer, a bone cancer, a nervous system cancer, gynecological cancer, a hematologic cancer, or a combination thereof. The subject may be a human, dog, cat, horse, or other mammal.

The compounds of the present invention may take the form of salts when appropriately substituted with groups or atoms capable of forming salts. Such groups and atoms are well known to those of ordinary skill in the art of organic chemistry. The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

The present disclosure describes compositions, kits and methods of treatment (e.g., imaging, diagnosis, therapy, radiotherapy, etc.) of neuroendocrine tumors (NETs) overexpressing somatostatin receptors (SSTR). This treatment involves the use of a cancer targeting composition comprising a radioisotope (e.g., an α-emitter, a β-emitter, a γ-emitter, a positron emitter, and/or other radioactive emitters), chelated by a chelator [CA] or "Ch" to a targeting moiety comprising a somatostatin receptor targeting peptide (e.g., octreotate, octreotide, and/or other derivatives, including "Tm"). The chelator may have a nitrogen ring structure, such as a tetraazacyclododecane derivative, a triazacyclononane derivative, and/or a tetraazabicyclo [6.6.2] hexadecane derivative (e.g., DOTAM, TCMC, DOTA, etc.). See, Tm of Formula (I).

In particular, DOTAM and TCMC may be used to chelate a radioisotope (e.g., lead (Pb) or copper (Cu)) to a targeting moiety (e.g., octreotate, octreotide derivative) in a manner that provides stable coordination of radioisotope and its products of radioactive decay. Experiments herein indicate that molecules having a target moiety and a chelator (e.g., DOTAM, TCMC) are capable of selectively delivering a radioisotope to cancer cells while limiting cytotoxic effects on healthy tissues.

Radiolabeled conjugates are derivatives of chelator coordinating the radioisotope and cancer specific targeting ligands that recognize receptors or transporters on cancer cells. This approach may be used for selective delivery of the radioisotope to the cancer cells with limited effect on healthy cells and tissues. The compositions herein seek to provide conjugates of the chelator modified with a peptide targeting SSTR in the cancer cells. The compositions may be administered by injection of a solution of a radioactive complex of this composition. The conjugates described herein seek to offer a platform for generating stable complexes with α, β$^+$, β$^-$, and/or γ-emitting radionuclides for cancer treatment. The techniques herein seek to treat a disease state in the patient by administering a pharmaceutically-acceptable injectable solution into the patient.

While the methods and compositions described herein relate to certain cancer treatment, such may also be applicable to cardiovascular disease, infection, diabetes, cancer, and/or other conditions. For cases involving cancer, the cancer may be, for example, a solid tumor derived, for example, either primarily or as a metastatic form, from cancers such as of the liver, prostate, pancreas, head and neck, breast, brain, colon, adenoid, oral, skin, lung, testes, ovaries, cervix, endometrium, bladder, stomach, epithelium, etc.

In another aspect, a method of treating an individual suffering from a cellular proliferative disorder, particularly cancer, is provided, comprising administering to said individual an effective amount of at least one compound according to Formula I, or a pharmaceutically acceptable salt thereof, either alone, or in combination with a pharmaceutically acceptable carrier.

In yet another aspect, a method of inducing apoptosis of cancer cells, such as tumor cells, in an individual afflicted with cancer is provided, comprising administering to said individual an effective amount of at least one compound according to Formula I, or a pharmaceutically acceptable salt thereof, either alone, or in combination with a pharmaceutically acceptable carrier.

The compounds of Formula I may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated within the scope of the invention is the instillation of a drug in the body of the patient in a controlled formulation, with systemic or local release of the drug to occur at a later time. For example, the drug may be localized in a depot for controlled release to the circulation, or for release to a local site of tumor growth.

One or more compounds useful in the practice of the present disclosure may be administered simultaneously, by the same or different routes, or at different times during treatment. The compounds may be administered before, along with, or after other medications, including other antiproliferative compounds.

The treatment may be carried out for as long a period as necessary, either in a single, uninterrupted session, or in discrete sessions. The treating physician will know how to increase, decrease, or interrupt treatment based on patient response. The treatment may be carried out for from about four to about sixteen weeks. The treatment schedule may be repeated as required.

Targeted Cancer Treatment

1. DOTATATE

Cancer treatment may involve the use of compositions that target and trigger cell death (apoptosis) of the cancer cells in the patient. Some forms of targeted treatment of cancer cells may use compositions having molecules which bind to specific antigens of the cancer cells. For example, targeting moieties, such as small molecular weight proteins or monoclonal antibodies, may be used to recognize and bind to the cancer cells using specific cellular antigens which may be located on a surface of the cancer cells. The peptides can be tagged with cytotoxic agents or isotopes/metals to label them and/or to induce the apoptosis. The binding of the peptides may enable specific recognition of cancer antigen-presenting cells which may be used for imaging and/or treatment. For example, targeting agents such as peptides, antibodies and antibody fragments and the like, may be coupled with various cell cytotoxic agents, such as chemotherapeutic agents and/or other promoters of the apoptosis.

Cancer targeting compositions, such as DOTATATE, may be used in treatment of cancer overexpressing specific somatostatin receptors, including neuroendocrine tumors (NETs). DOTATATE as used herein refers to a DOTA chelator conjugated with a targeting moiety, such as octreotate. DOTA as used herein refers to an organic compound having the formula $(CH_2CH_2NCH_2CO_2H)_4$ and is a 1,4,7,10-tetraazacyclododecane-1,4,7,10-tetraacetic acid. DOTA may refer to a tetracarboxylic acid and its various conjugate bases. DOTA includes a tetraaza ring of nitrogen atoms with terminal groups ready for conjugation of ligands. DOTA may be used as a chelator (chelating agent) for bonding metal ions and radioisotopes. Targeting moiety as used herein refers to, for example, a peptide, a protein, an antibody, a nucleoside, a nucleotide, an alcohol, a heterocyclic compound, and/or other ligand that bonds to an antigen on a target cell, such as the cancer cell. The targeting moiety may enter and induce apoptosis of the target cancer cell.

DOTATATE includes a chelator, DOTA, and coordinated metals or radioisotopes. The radioisotope may be coordinated by the cancer targeting composition (e.g., contained, complexed) and may be delivered selectively to the cancer cells. This coordination may be used to minimize side effects of the free radioisotope and/or its radioactive decay products. For example, radiolabeled SSTR-ligands, such as $^{90}$Y-DOTATOC or $^{177}$Lu-DOTATATE, may be used in the treatment of NETs. Due to its potential for enhanced safety, DOTATATE has been used in numerous clinical trials. See, e.g., Bushnell et. al., 90Y-Edotreotide for Metastatic Carcinoid Refractory to Octreotide, J. Clin. Oncol., 28:1652-1659 (2010); and Kwekkeboom D J, Bakker W H, Kam B L, et al., Treatment of Patients With Gastro-Entero-Pancreatic (GEP) Tumours With The Novel Radiolabelled Somatostatin Analogue [$^{177}$Lu-DOTA0,Tyr3] Octreotate, European Journal of Nuclear Medicine and Molecular Imaging, 2003; 30(3):417-422, the entire contents of which are hereby incorporated by reference herein. Experiments indicate positive effects, such as an increased median progression-free survival (mPFS) and increased disease control rates (DCR, proportion of patients with stable disease, partial or complete response).

As described further herein, DOTATATE may chelate both the diagnostic, as well as the precursor radioisotope, and the spent atom after radioactive decay, as well as any atoms in between. For example, DOTATATE may initially chelate the radioisotope, and then retain chelation of the decay product(s) of the radioisotope. This may prevent free (non-chelated) radioisotopes from entering the blood by dissociating from the carrier (DOTATATE). The chelator may also chelate the spent radioisotope after its decay in vivo. This may potentially prevent radioactive and/or toxic free decay atoms from dissociating from the chelator and entering the blood.

2. DOTAMTATE and TCMCTATE

Other chelators may be used for stable coordination of isotopes, such as DOTAM, TCMC-monoacid, and TCMC (defined further herein). Such chelating agents can coordinate both diagnostic and therapeutic radioisotopes and may be used for treatment of cancer cells. The DOTAM and TCMC are similar to DOTA, with different terminal groups which give them increased coordination stability and increased radiochemical stability properties, for example, when used with certain radioisotopes and targeting moieties. The targeted radiotherapy may use chelators, such as DOTAM and TCMC, in combination with compositions, such as octreotate peptide, that are designed to hold (e.g., prevent, slow dissociation, etc.) of the radioisotope. These compositions seek to selectively deliver the radioisotope to target cancer cells and prevent dissociation of the radioisotope from the chelator.

In particular, cancer treating compositions may include the DOTAM, TCMC, and TCMC-monoacid chelators used in combination with radioisotopes and octreotate peptide targeting moieties to further enhance treatment properties. The radioisotopes, such as $^{212}$Pb, $^{203}$Pb, $^{64}$Cu, and/or other radionuclide α-emitters, have high linear energy transfer (LET) emission and short path lengths that irradiates a short distance, such as within about 1-2 cell diameters, and/or that may not require oxygenation or reproduction to irreversibly damage (e.g., kill) a tumor cell.

As shown herein, these components form stable complexes with isotopes that seek to prevent dissociation of the lead radioisotope from the conjugate under mildly acidic conditions, such as in vivo. Examples herein use $^{212}$Pb, $^{203}$Pb, or $^{64}$Cu as the radioisotope bound to the DOTAM, TCMC, and TCMC-monoacid for the targeted imaging and therapy of cancer. Other radioisotopes may include, for example, iron, cobalt, zinc, and other metals with a density of over about 3.5 $g/cm^3$.

The DOTAM, TCMC, and TCMC-monoacid based cancer treating compositions may also form stable complexes with other radioisotopes, and therefore selectively deliver the radioisotopes to the cancer cells and prevent their dissociation that could induce cytotoxic effect in normal cells. Due to their properties, such compositions may be used for treatment of NET tumors with specific cancer treatment wherein the isotopes are selectively delivered to the SSTR expressing cancer cells by targeting moieties, such as octreotate, octreotide, or other somatostatin analogs. The octreotate based compounds may be used, for example, for diagnosis of patients with SSTR-positive NETs using γ-emitting isotopes, and/or in treatment of NET patients using β-emitting isotopes (e.g., $^{177}$Lu and $^{90}$Y). See, e.g., Kwekkeboom, D. J. et. al., Radiolabeled Somatostatin analogue 177Lu-DOTA-tyr3 Octreotate in Patients with Endocrine Gastoentoeropancreatic Tumors, J Clin Oncol 23:2754-2762, (2005); van Essen, M. Krenning E P, et. al, Peptide Receptor Radionuclide Therapy With $^{177}$Lu-Octreotate in Patients With Foregut Carcinoid Tumors of Bronchial, Gastric and Thymic Origin, European Jnl. of Nuclear Medicine and Molecular Imaging (2007), the entire contents of which are hereby incorporated by reference herein. In the composition comprising a molecule of Formula (I) or a pharmaceutically acceptable salt thereof, at least one of $R^5$, $R^6$, and $R^8$ is $(C_1-C_6)$alkyl-C(=O)—N(—$R^{25}$)—$R^{26}$, which can provide increased coordination stability and increased radiochemical stability properties, for example, when used with certain radioisotopes and targeting moieties.

The radioisotopes may be used, for example, to provide a source of alpha irradiation via indirect emission. The radioisotopes (e.g., $^{212}$Pb, $^{203}$Pb, $^{64}$Cu, etc.) may be combined with chelators (e.g. DOTAM, TCMC, etc.) and targeting moieties (e.g., octreotate), into a cancer targeting composition for rapid uptake of the composition into the cancer cells. The DOTAM and TCMC chelators may be used to avoid dissociation of the radioisotope from the conjugate under mildly acidic conditions, such as within the patient's body.

The targeted cancer treatment may involve the use of radioisotopes bound to the chelators which are bound to the targeting moiety which recognizes and binds to cell surface receptors expressed on (or which are up-regulated on) specific cancer cells. This may cause binding of the radioisotope-chelators to the specific cancer cells, and thus targeted radiation of the specific cancer cell when the radioisotope undergoes radioactive decay.

Treatment (e.g., imaging and/or apoptosis) of cancer cells may involve use of emitters (such as e.g., α (alpha), β (beta), γ (gamma), and/or positron emitting radioisotopes) as the radioisotope(s). The α-emitting radioisotopes may be delivered to targeted cancer cells, e.g., NET via SSTR targeting moieties, such as octreotate or other octreotide derivatives. These α-emitting radioisotopes may be of particular interest because they have a high LET compared to other radioisotopes such as $^{177}$Lu, $^{90}$Y, and/or other β-emitters, and may deposit their high energy within about a 70 to about a 100 μm long pathway tracking within about 1 to about 2 cancer cell clusters. This high LET radiation may not depend on active cell proliferation or oxygenation, and/or the resulting Deoxyribonucleic acid (DNA) damage caused by α-particles may be more difficult to repair than that caused by β-emitting radioisotopes, due to α-emitting radioisotopes higher LET.

The α-emitting radioisotopes may have an LET that is powerful, and is also generally limited to within the internal region of the cancer cell. The emissions from the α-emitting radioisotopes may also have the ability to cause irreversible damage, such as oxygenation or reproduction, to the cancer cell that does not require waiting for the life cycle of the cancer cell. Further still, α-emitting radioisotopes can cause death and apoptosis of the cancer cells that developed resistance to β-emitter therapy.

The α-emitting radioisotopes may be, for example, produced during decay of lead based radioisotopes, such as $^{212}$Pb radioisotopes. The $^{212}$Pb is a β-emitting radioisotope with a half-life of about 10.6 hours with a radioactive emission profile having decay products which are α-emitters having the properties of α-emitting radioisotopes. Since $^{212}$Pb decays to $^{212}$Bi (which is an α-emitting radioisotope having a half-life of about 60 minutes), which decays whether by α-emission to $^{208}$Tl (with a half-life of about 3 min), which decays by β-emission to $^{208}$Pb (which is stable), or by β-emission to $^{212}$Po (with a half-life of about 0.3 μs), which decays by α-emission to 208Pb.

The use of a radioisotope with a relatively long half-life, such as $^{212}$Pb having a half-life of about 10.6 hours, may allow for centralized production of radiolabeled compositions at the radiopharmacy and shipment to the clinic where it is administered to the patient. The α-emitter decay of $^{212}$Bi may be maximized to occur within the cancer cells, thereby providing maximum alpha radiation damage once inside the cancer cells and their apoptosis and killing of the cancer cell. After α-emission by the $^{212}$Bi, the ultimate result is the stable $^{208}$Pb.

As indicated by the experimental data provided herein, a combination of certain radioisotopes chelated using DOTAM or TCMC conjugated to octreotide derivative somatostatin receptor targeting moieties provides treatment properties, such as increased radiochemical stability, enhanced binding and increased uptake by cancer cells, and/or high LET emission within cancer cells that results in their apoptosis and/or targeted biodistribution. For example, radiolabeled-octreotate, octreotide conjugates may consist of a SSTR-targeting peptide modified with the chelator (e.g., TCMC, DOTAM) radiolabeled with the β-emitting or α-emitting radioisotope.

Composition

Figure 1B:
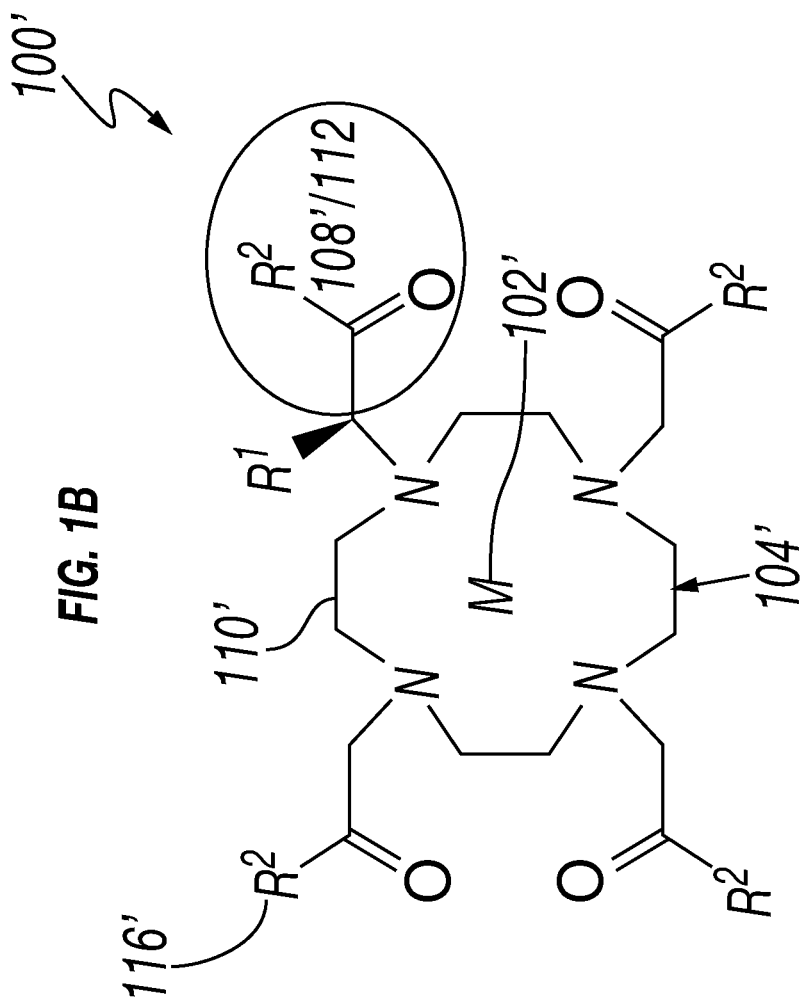

FIGS. 1A and 1B schematically depict example cancer targeting compositions 100, 100' for treating cancer cells in a cancer patient. As shown in the example of FIG. 1A, the composition 100 comprises a radioisotope 102, a chelator 104, and a targeting moiety 108.

The radioisotope (or radioactive atom or ion) 102 may be an atom or an ion, such as an α-emitter, a β-emitter, a γ-emitter, a positron emitter, and/or other radioactive emitter, capable of undergoing radioactive decay within the patient. The radioisotope 102 may be, for example, a radioactive emitter, such as $^{212}$Pb, $^{203}$Pb, $^{64}$Cu, $^{67}$Cu, $^{212}$Bi, and/or other radioactive emitter. Examples of non-limiting radioactive emitters that may be used as the radioisotope include $^{68}$Ga, $^{177}$Lu, $^{213}$Bi, and $^{90}$Y. Other example radioisotopes that may be used may include $^{225}$Ac, $^{231}$Am, $^{243}$Am, $^{211}$At, $^{217}$At, $^{247}$Bk, $^{248}$Cf, $^{250}$Cf, $^{251}$Cf, 240Cm, $^{243}$Cm, $^{245}$Cm, $^{154}$Dy, $^{252}$Es, $^{253}$Es, $^{255}$Es, $^{252}$Fm, $^{253}$Fm, $^{221}$Fr, $^{148}$Gd, $^{174}$Hf, $^{258}$Md, $^{144}$Nd, $^{237}$Np, $^{186}$Os, $^{190}$Pt, $^{236}$Pu, $^{238}$Pu, $^{213}$Pa, $^{231}$Pa, $^{223}$Ra, $^{224}$Ra, $^{219}$Rn, $^{146}$Sm, $^{147}$Sm, $^{149}$Tb, $^{227}$Th, $^{229}$Th, $^{230}$U and/or $^{236}$U. Other possible radionuclides may include $^{45}$Ti, $^{59}$Fe, $^{60}$Cu, $^{61}$Cu, $^{62}$Cu, $^{67}$Ga, $^{89}$Sr, $^{86}$Y, $^{94}$mTc, $^{99}$mTc, $^{111}$In, $^{149}$Pm, $^{153}$Gd, $^{153}$Sm, $^{166}$Ho, $^{186}$Re, $^{188}$Re, or $^{211}$At.

The chelator [CA] 104 is a chemical (e.g., organic chemical) capable of binding to the radioisotope 102 and to the targeting moiety 108. The chelator 104 includes a ring structure 110 and multiple terminal groups 112. The chelator 104 may include, for example, a tetraaza ring 110, such as DOTA (1,4,7,10-tetraazacyclododecane-1,4,7,10-tetraacetic acid), DOTAM (1,4,7,10-Tetrakis(carbamoylmethyl)-1,4,7, 10-tetraazacyclododecane), TCMC (2-(4-isothiocyanotobenzyl)-1, 4, 7, 10-tetraaza-1, 4, 7, 10-tetra-(2-carbamonyl methyl)-cyclododecane), and/or other chelating agents. When bound with the targeting moiety 108, the chelator 104 may form a compound, such as DOTAMTATE, DOTATATE, TCMCTATE, and/or other chelating compound.

Example chemical structures of chelators 204a-h usable as the chelator 104 are provided in FIGS. 2A1-2B4. FIGS. 2A1-2A4 show example chelators usable with $^{212}$Pb, $^{203}$Pb, and $^{212}$Bi. FIGS. 2B1-2B4 show example chelators usable with $^{64}$Cu and $^{67}$Cu.

Referring back to FIG. 1A, the ring structure 110 includes multiple nitrogen atoms (N) bonded together by carbon atoms (e.g., alkanes, alkenes, etc., shown by vertices connected by straight lines in the FIG. 1A). The ring structure 110 may be, for example, a tetraaza ring comprising four nitrogen atoms. As shown by the example of FIG. 1A, one of the terminal groups 112 may be coupled to each of the nitrogen atoms in the ring structure 110. As shown in FIG. 1A, at least one of the terminal groups 112 may be replaced by the targeting moiety 108. Each of the terminal groups 112 may include one or more chemicals used for chelating. For example, the terminal groups 112 may include alkanes, alkenes, acetic acid, carboxylamine, and/or other chemicals that provide binding capabilities for the cancer targeting composition 100.

The targeting moiety 108 is a chemical which binds to the cancer cells, such as a somatostatin receptor (SSTR) targeting peptide (somatostatin analog), in the patient. The targeting moiety 108 may be, for example, a peptide, such as octreotate (H-D-Phe-Cys-Phe-D-Trp-Lys-Thr-Cys-Thr-OH, $C_{49}H_{64}N_{10}O_{11}S_2$), octreotide ($H_2N$-D-Phe-Cys-Phe-D-Trp-Lys-Thr-Cys-Thr-ol, $C_{49}H_{66}N_{10}O_{10}S_2$), other octreotate/octreotide derivatives, and/or other cancer targeting chemicals.

The targeting moiety 108 may be linked to the chelating agent 104 by a covalent bond 114. The covalent bond may be coupled to an amide group as schematically shown by the solid bond 114, or to another portion of the tetraaza ring structure 110, such as a Carbon, as schematically shown by the dashed bond 114'.

A linker [L]x 116 may also optionally be provided to bind the chelator 104 to the targeting moiety 108. The linker 116 may be, for example, an organic compound, such as an amino acid, alkane, alkyne, etc. Linkers may be selected from the group of amino acids, peptides, amino alcohols, polyethylene glycols, alkanes, alkenes, alkynes, azide aromatic compounds, carbohydrates, carboxylic acids, esters, phospho-organic compounds, and sulfonates. The linker 116 may be defined to provide a spacer between the chelator 104 and targeting moiety 108, for example, to avoid ionic interactions.

FIG. 1B shows another example structure of the cancer targeting composition 100'. The cancer targeting composition 100' may be similar to the composition 100 of FIG. 1A, except with various terminal groups further defined. The radioisotope 102' (denoted generally as M) may be an α, β+, β−, γ-emitting, and/or other radioisotope similar to radioisotope 102 of FIG. 1A. The chelator 104' may be a ring structure 110' with multiple nitrogen atoms bonded together, similar to the chelator 104 of FIG. 1A.

In this version, the terminal groups 112' and the targeting moiety 108 are both depicted as being an oxygen atom and an $R^2$ bonded to each nitrogen atom of the ring structure 110'. As indicated in the Legend of FIG. 1B, $R^2$ may have multiple possible definitions, such as OH, NH, N—$C_1$-$C_6$ alkyl (straight or branched chain), N in combination with polyethylene glycol, $L_1$, or N in combination with the functional groups 304a, b of FIGS. 3A and 3B.

The functional group 304a of FIG. 3A is further defined to include O in combination with $R^4$. $R^4$ may be H, a straight-chain C1-C6 alkyl, or a branched-chain C1-C6 alkyl. The functional group 304b of FIG. 3B is further defined to include O double bonded to C with $R^4$ single bonded to N.

Referring back to FIG. 1B, the targeting moiety 108' is depicted as being linked to the ring structure 110' by a linker 116'. As indicated by the Legend, the linker 116' is depicted as $R^2$ including a linker bonded to a chelator ([L]x-[CA]). The chelator [CA] may be similar to the chelators 104, 204a-h of FIGS. 1A, 2A1-2B4 (or other chelator as described herein). The linker 116' may be similar to the linker 116 of FIG. 1A (or other linker as described herein).

As shown in FIG. 4A, the linker 116' may be a linker [L]x 416a, such as an Oxygen (O), coupled between the targeting moiety 116' (shown as $CO_2H$) and the ring structure 110' (shown as $H_2N$). As shown in FIG. 4B, the linker 116' may be a linker 416b, such as a direct bond between the targeting moiety 116' (shown as $CO_2H$) and the ring structure 110' (shown as $H_2N$).

While FIGS. 1A-4B show specific configurations of the cancer targeting composition, the targeting moiety, the chelator, and/or other components, various positions and combinations may be provided. For example, the targeting moiety may be at various positions about the chelator, and one or more various terminal groups may be provided. Other variations may also be provided. See, for example, US Patent/Application Nos. 2016/0143926, 2014/0228551, and 9408928, previously incorporated by reference herein.

Figure 5A:
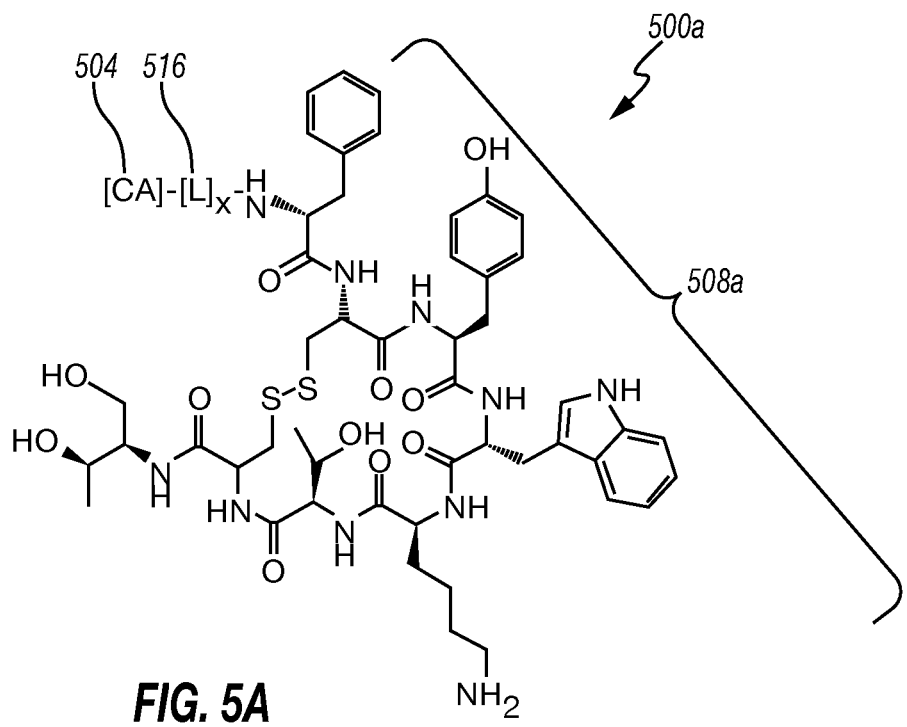
FIGS. 5A-5B are example chemical structures of the cancer targeting composition comprising DOTATOC and DOTATATE, respectively.
Figure 5B:
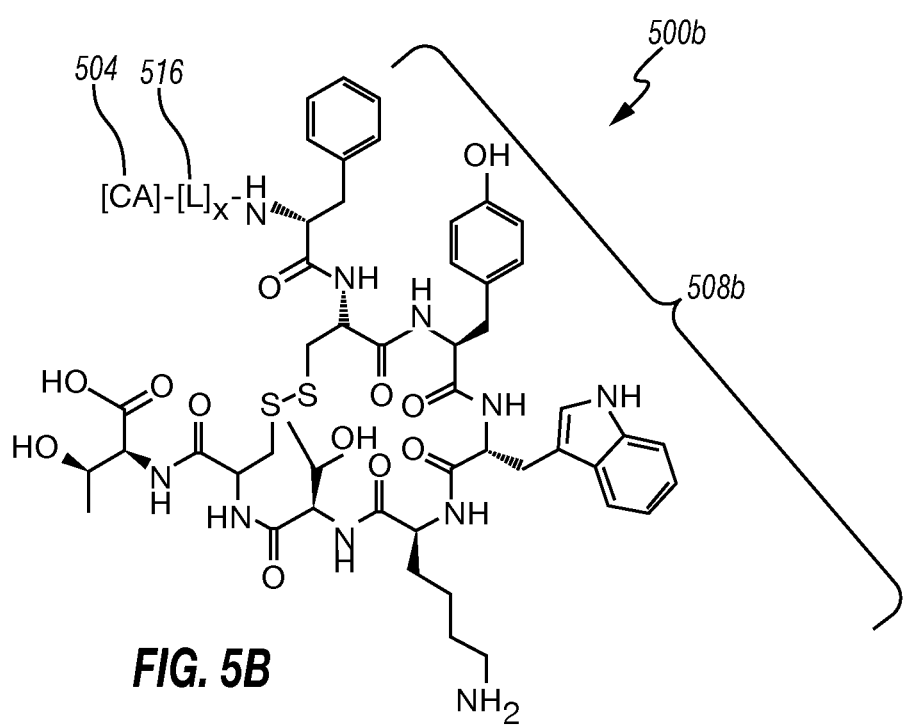

FIGS. 5A and 5B show example chemical structures 500a, 500b for the cancer targeting composition (e.g., 100, 100'). The chemical structures 500a,b each include a chelator [CA] 504 and targeting moiety 508a,b, and a linker a linker ([L]x) 516. The chelator 504 and linker 516 may be similar to the chelator 104, 104' and linkers 116, 116' ([L]x-[CA]) as described with respect to FIGS. 1A and 1B, respectively.

In these versions, the targeting moieties 508a,b comprise TOC and TATE, respectively. DOTATOC (or Edotreotide, SMT487, DOTA0-Phe1-Tyr3 octreotide or DOTA-Tyr3-octreotide) has the chemical formula $C_{65}H_{92}N_{14}O_{18}S_2$. DOTATATE (or DOTA-TATE or DOTA-octreotate or DOTA-(Tyr$^3$)-octreotate) is an amide of the acid DOTA which acts as a chelator, and which has the chemical formula $C_{65}H_{90}N_{14}O_{19}S_2$. TCMCTATE (described further herein) is a chelator having the chemical formula S-2-(4-isothiocyantobenzl)-1, 4, 7, 10-tetraaza-1, 4, 7, 10=tetra (2-carbamoylmethl) cyclododecane.

DOTAMTOC, DOTAMTATE, and TCMCTATE may be synthesized as described further therein.

Figure 6A:
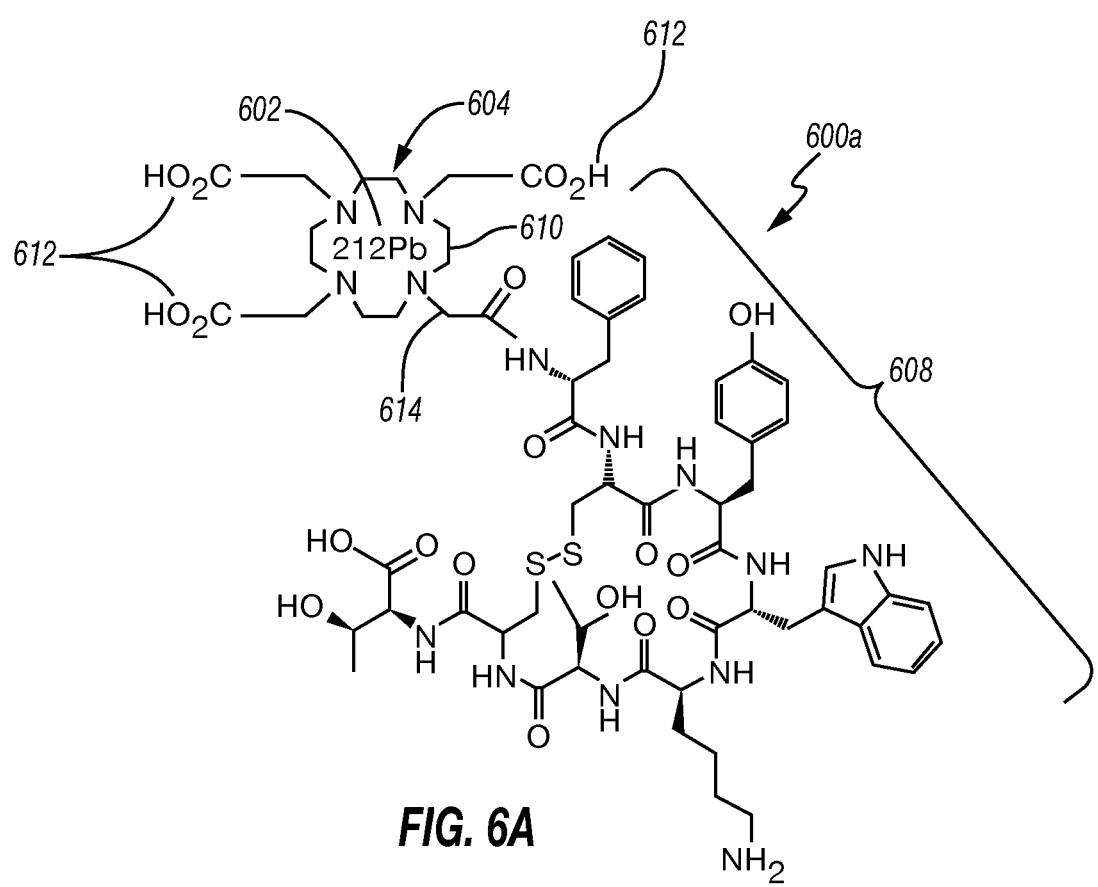
FIGS. 6A-6C are example chemical structures of the cancer targeting composition comprising a methylcarboxyl terminal group ($CH_2$—C(=O)—OH), an acetamide terminal group ($CH_2$—C(=O)—$NH_2$), and an acetamide terminal group with a linker, respectively.
Figure 6B:
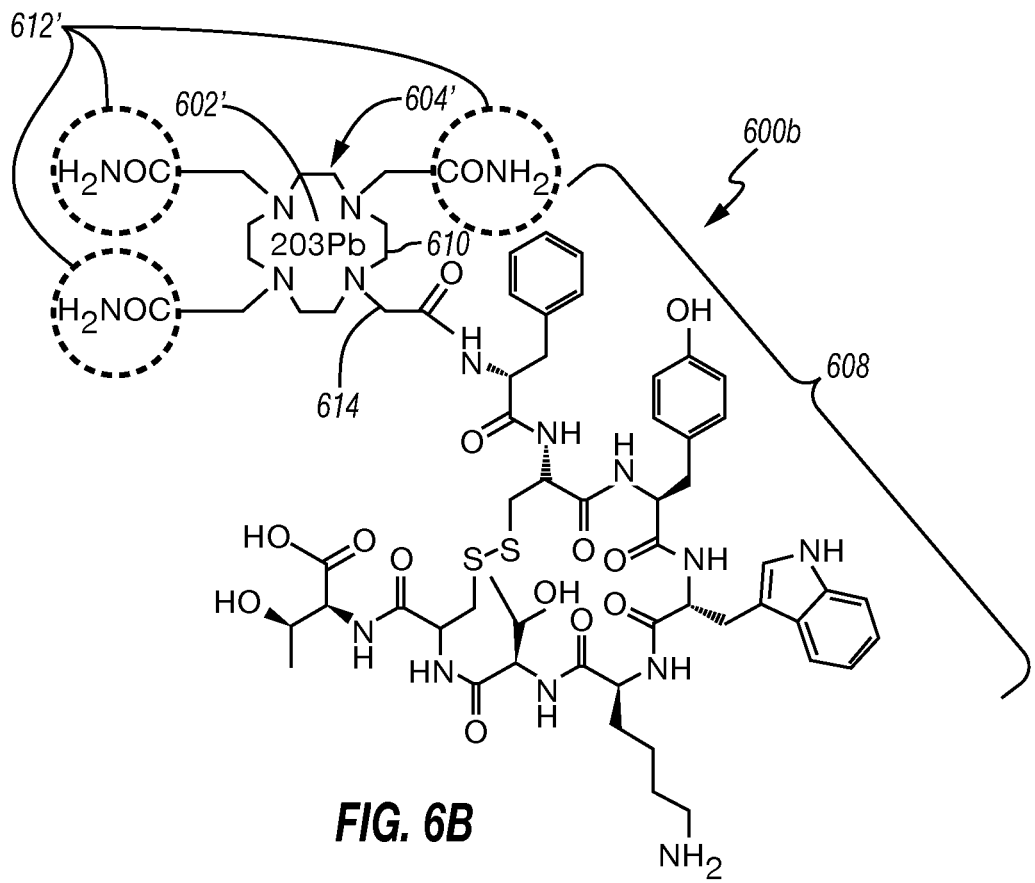
Figure 6C:
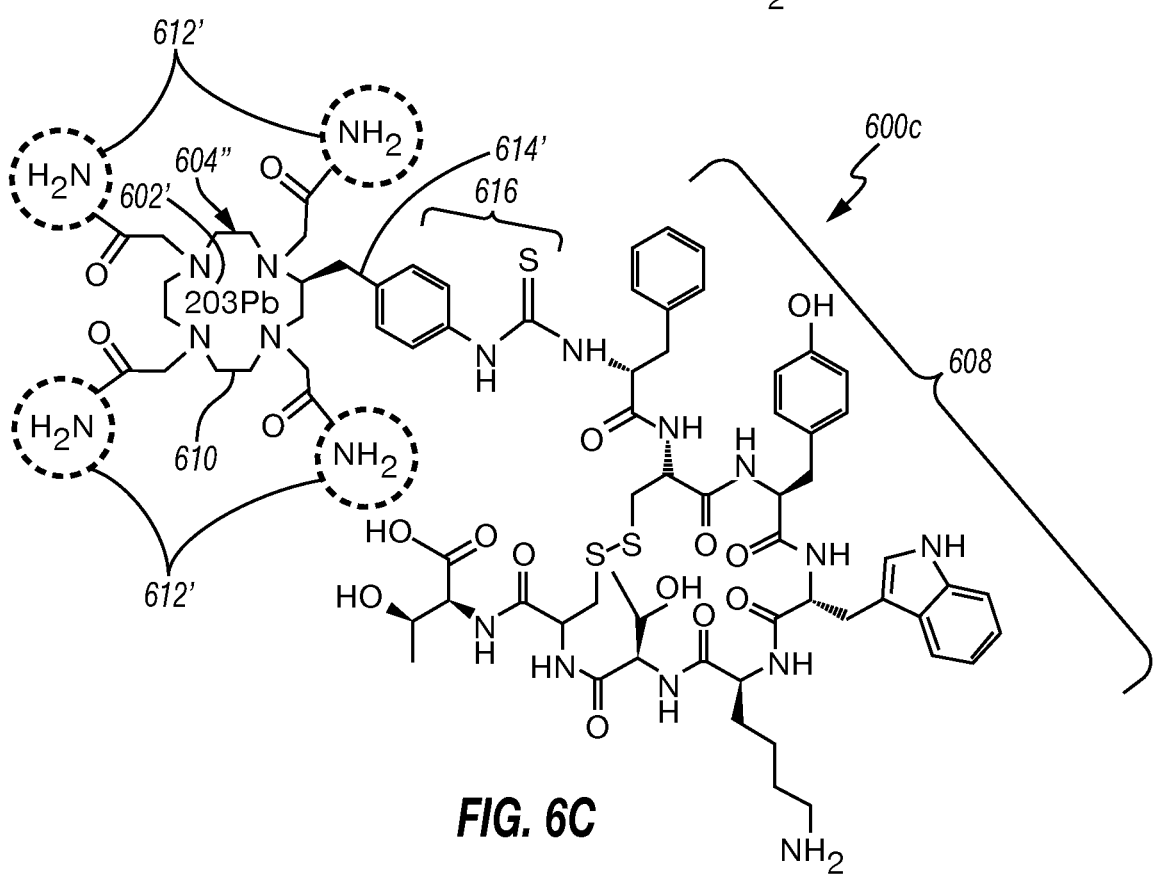

FIGS. 6A-6C show additional chemical structures 600a-c for the cancer targeting composition (e.g., 100, 100'), including DOTATATE, DOTAMTATE, and TCMCTATE, respectively. Each of these cancer targeting compositions 600a-c includes a Pb radioisotope 602, 602', a tetraaza ring 610, chelator 604, 604', 604", terminal groups 612, 612', 612", and the octreotate targeting moiety 608.

In the DOTATATE cancer targeting composition 600a of FIG. 6A, the radioisotope (M) 602, is $^{212}$Pb and the terminal groups 612 are methylenecarboxylic acid. The chelator 604 includes a tetraaza ring 610 with four (4) nitrogen atoms. Each nitrogen atom is coupled to an ethane group to form the tetraaza ring 610. Three terminal groups 612 are coupled to the tetraaza ring 610. Each of the terminal groups 612 includes a methylcarboxyl group, and is attached to one of the nitrogen atoms of tetraaza ring. The remaining nitrogen atom of the tetraaza ring 610 is bound to the octreotate targeting moiety 608 by bond 614.

In the DOTAMTATE version of FIG. 6B, the composition 600b is similar to that of FIG. 6A, except that the chelator 604' is a DOTAM, and the terminal groups 612 have been replaced with terminal groups 612', and the radioisotope (M) 602 has been replaced with radioisotope 602'. The terminal groups 612' include an acetamide group and the radioisotope 602' includes $^{203}$Pb.

In the TCMCTATE version of FIG. 6C, the composition 600c is similar to that of FIG. 6B, except that the targeting moiety 608 has been conjugated to an isothiocyanate group linker 616 and the terminal group 612' has been replaced with terminal group 612". Linker 616 is bonded to the chelator 604' by bond 614'. The terminal group 612" in this case is H$_2$N.

While FIGS. 6A-6C depict specific examples of cancer targeting compositions, it will be appreciated that various radioisotopes, chelators, targeting moieties, linkers, and/or other components may be provided. Examples of components are provided in US Patent Application Nos. US2009/0087377, US2014228551, US20120052008, and US20100316566, the entire contents of which are hereby incorporated by reference herein. The combination of components may be selected to achieve the desired cancer targeting properties as is described further herein. For example, various chelators may be used in combination with lead radioisotopes. The TCMCTATE and DOTAMTATE may have similar molecular weight to DOTATATE, and change the overall charge of the molecules from (−1) charge for $^{203}$Pb-DOTATATE to (+2) for $^{203}$Pb-TCMCTATE and $^{203}$Pb-DOTAMTATE. In another example, while DOTATATE, DOTAMTATE, and TCMCTATE compositions of FIGS. 6A-6C are shown to be conjugated to octreotate, the targeting moiety may be any peptide or other targeting group capable of binding to the cancer cells.

EXAMPLES

Peptide Synthesis:

The examples herein may involve peptide synthesis. Cyclic peptide may be synthesized, for example, via solid-phase peptide synthesis using a fluorenylmethyloxycarbonyl (FMOC) strategy. After cleavage from the solid support, disulfide bond formation can be accomplished with peroxide in tetrahydrofuran (THF) and 5 mM ammonium acetate buffer (NH$_4$OAc). The final product may be purified by a preparative, such as liquid chromatography-mass spectrometry (LC-MS or HPLC-MS). Examples of synthesis that may be used are described in Schottelius et al, H. J. Wester Tetrahedron Letters vol. 44, pp. 2393-2396 (2003), the entire contents of which is hereby incorporated by reference herein.

The 1,4,7,10-tetraazacyclododecane-1,4,7(2-carbamolymethyl)-10(mono-N-hydroxysuccinimide ester [DOTAM-monocarboxylic acid] may be synthesized by the following:

1. 1,4,7,10-Tetraazacyclododecane-1,4,7-tris (t-butoxycarbonyl) is dissolved in acetonitrile. Potassium carbonate is added. Benzyl bromoacetate is added neat. The solution is stirred at room temperature. After four days, the solids are removed by filtration. The solvent is removed by rotary evaporation at 40° C. The residue is dissolved in dichloromethane and washed with water. The organic layer is dried over sodium sulfate. The drying agent is removed by filtration. The solvent is removed from the filtrate by rotary evaporation. The resulting solid is dried under high vacuum to yield the product.

2. The isolated product from step 1 is dissolved in neat trifluoroacetic acid (TFA). The solution is stirred for 1 day. The TFA is removed by rotary evaporation. The resulting oil is dissolved in water and washed with chloroform. The aqueous layer is basified with sodium hydroxide to pH=1. The product is extracted with chloroform. The organic layer is dried with sodium sulfate. The solution is filtered. The solvent is removed by rotary evaporation. The residue is dried under high vacuum to yield the product as an oil.

3. The isolated product from step 2 is dissolved in ethanol and diisopropylethylamine is added. 2-Bromoacetamide in ethanol is then added and the solution is stirred for ≥4 hours. The solvent is removed by rotary evaporation at 35° C. The oil residue is dissolved in chloroform and any solids that form are filtered and discarded. The solvent is removed from the filtrate by rotary evaporation. The residue is dried under high vacuum for ≥2 hours. The residue is taken in acetone. A solid precipitates. The solids are filtered and washed with cold acetone. The solids are dried under high vacuum to yield the product.

4. The isolated product from step 3 is hydrogenated in water in the presence of 10% Pd (palladium) on activated carbon under 30 psi (207 kPa) of hydrogen pressure. The solution is filtered and the solvent is removed by rotary evaporation. The residue is taken in ethanol and stirred vigorously. The product precipitates. It is filtered and dried under high vacuum.

TCMCTATE may be synthesized by the following: TATE is synthesized by solid phase peptide synthesis (SPPS) and cleaved from the resin without removing the protecting groups of its side chains. TATE is then dissolved in acetonitrile along with diisoproplyethylamine (2× molar excess). A solution of TCMC (Macrocyclics product B-1005) is added and the reaction mixture is stirred at room temperature. Reaction progress is monitored by liquid chromatography-mass spectroscopy (LC/MS). Upon completion the solution is concentrated in vacuo. The protecting groups of the side chains are removed with a cocktail of trifluoroacetic acid and radical scavengers, and then the product is precipitated with diethyl ether. The linear peptide is cyclized in solution and the crude is purified by preparative reversed phase liquid chromatography (RP/LC).

DOTAMTATE may be synthesized by the following: TATE is synthesized by SPPS and DOTAM-monocarboxylic acid (Macrocyclics product B-170) is attached to the peptide while it is still in the resin. The peptide conjugate is cleaved from the resin with a cocktail of trifluoroacetic acid (TFA) and radical scavengers, and the product is precipitated with diethyl ether. The linear peptide is cyclized in solution and the crude is purified by preparative reversed phase liquid chromatography (RP/LC).

DOTAMTOC may be synthesized by the following: TOC is synthesized by SPPS and DOTAM-monocarboxylic acid (Macrocyclics product B-170) is attached to the peptide while it is still in the resin. The peptide conjugate is cleaved from the resin with a cocktail of trifluoroacetic acid (TFA) and radical scavengers, and the product is precipitated with diethyl ether. The linear peptide is cyclized in solution and the crude is purified by preparative reversed phase liquid chromatography (RP/LC).

TCMCTOC may be synthesized by the following: TOC is synthesized by solid phase peptide synthesis (SPPS) and cleaved from the resin without removing the protecting groups of its side chains. TOC is then dissolved in acetonitrile along with diisoproplyethylamine (2× molar excess). A solution of TCMC (Macrocyclics product B-1005) is added and the reaction mixture is stirred at room temperature. Reaction progress is monitored by liquid chromatography-mass spectroscopy (LC/MS). Upon completion the solution is concentrated in vacuo. The protecting groups of the side chains are removed with a cocktail of trifluoroacetic acid and radical scavengers, and then the product is precipitated with diethyl ether. The linear peptide is cyclized in solution and the crude is purified by preparative reversed phase liquid chromatography (RP/LC). FIGS. 7A-20E show experimental data generated using various compounds, such as the cancer targeting compositions 600a-c of FIGS. 6A-6C. As indicated by these experiments, the therapeutic efficacy of cancer targeting compositions may be enhanced by the use of the radioisotopes (e.g., lead) chelated by a tetraaza ring conjugated to octreotate targeting moiety. The results of these experiments provided a basis for selection of DOTAMTATE or TCMCTATE octreotate conjugates for targeted cancer therapy using $^{212}$Pb.

Experiment 1—Radioisotope Binding to Chelator

FIGS. 7A-8B demonstrate the stability of $^{203}$Pb radioisotopes for the compositions of FIGS. 6B and 6C. As shown by the graphs of FIGS. 7A-8B, both $^{203}$Pb DOTAMTATE and $^{203}$Pb-TCMCTATE are synthesized with high radiochemical yields. These compositions show high chemical and radiochemical stability during their incubation in PBS buffer at room temperature as tested in multiple time points over time.

Figure 7A:
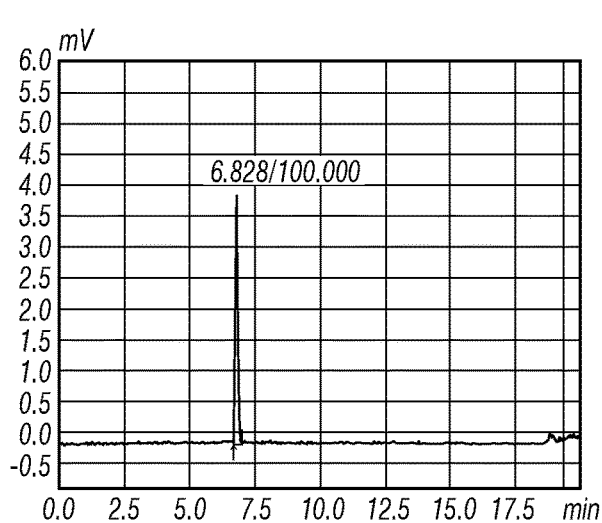
FIGS. 7A-7C are chromatographs depicting radiochemical stability of $^{203}$Pb-DOTAMTATE conjugates.
Figure 7B:
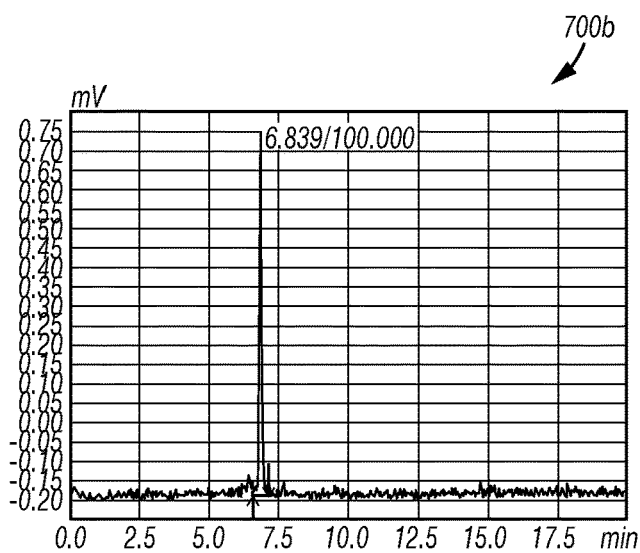
Figure 7C:
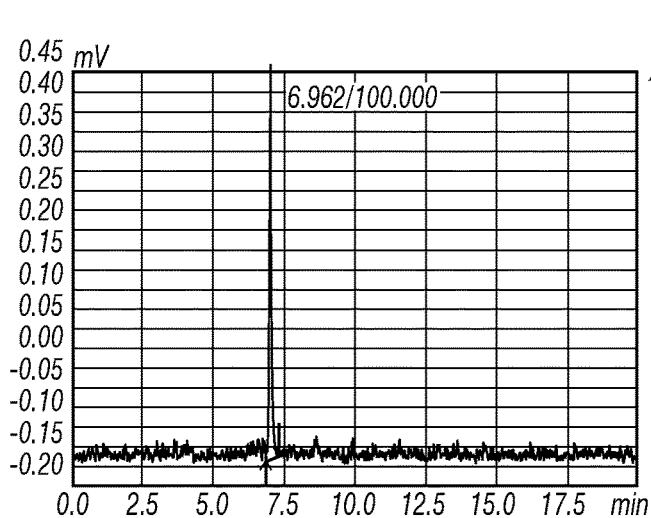

In particular, FIGS. 7A-7C show radio-high performance liquid chromatography (radio-HPLC) chromatograms 700a-c. These graphs 700a-c depict $^{203}$Pb-DOTAMTATE (15 µCi) (555 kBq) acquired at 0 hr, 1 hr, and 24 hrs after labeling of the DOTAMTATE with the $^{203}$Pb, respectively. Each graph 700a-c plots radiation intensity (y-axis, mV measured by a detector) versus runtime (x-axis, minutes) of the radio-HPLC (High-Performance Liquid Chromatography).

These graphs also demonstrate post-labeling to determine the radiochemical yield and radiochemical stability of the agent. The $^{203}$Pb-DOTAMTATE is synthesized with a radiochemical yield greater than or equal to 99.9%. The peak in all three chromatographs 700a-c indicates a high radiochemical stability for $^{203}$Pb-DOTAMTATE. In particular, since there are no secondary peaks indicating free $^{203}$Pb, the chromatographs indicate a radiochemical yield of ≥98% for up to at least 24 h post-labeling. As demonstrated by these graphs, the $^{203}$Pb DOTAMTATE remains radiochemically and chemically stable over time for the duration of the tests.

Figure 8A:
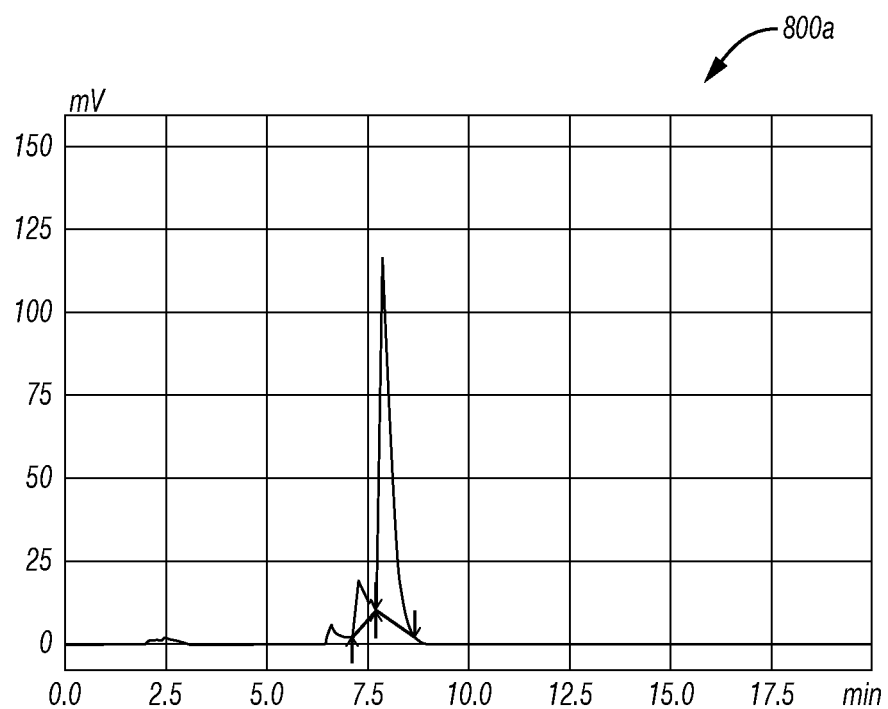
FIGS. 8A-8B are chromatographs depicting radiochemical stability of $^{203}$Pb-TCMCTATE.
Figure 8B:
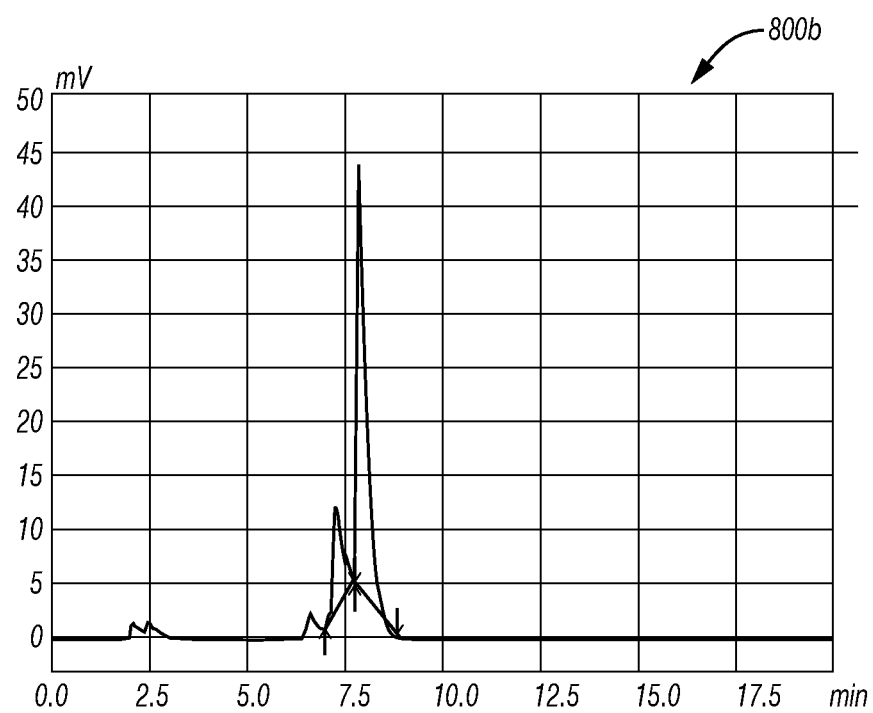

FIGS. 8A and 8B show radio-HPLC chromatograms 800a,b of $^{203}$Pb-TCMCTATE (555 kBq or 15 µCi) acquired at 0 hr and 18 hr after labeling the TCMCTATE with the $^{203}$Pb, respectively. As demonstrated by these graphs, the $^{203}$Pb-TCMCTATE also remains stable over time for the duration of the tests. Post-labeling data is also obtained to determine the radiochemical yield and radiochemical stability of $^{203}$Pb-TCMC-TATE, which is synthesized with a radiochemical yield of ≥99.9%. As shown in FIG. 8B, the $^{203}$Pb-TCMCTATE has high radiochemical stability (e.g., of about ≥96%) up to 18 h post-labeling.

The experiments in FIGS. 7A-8B indicate high binding affinity of DOTAMTATE and TCMCTATE for $^{203}$Pb. These figures also indicate that, once bound, the $^{203}$Pb radioisotopes remain bound for at least several hours.

Experiment 2—Radioisotope Uptake

Figure 9:
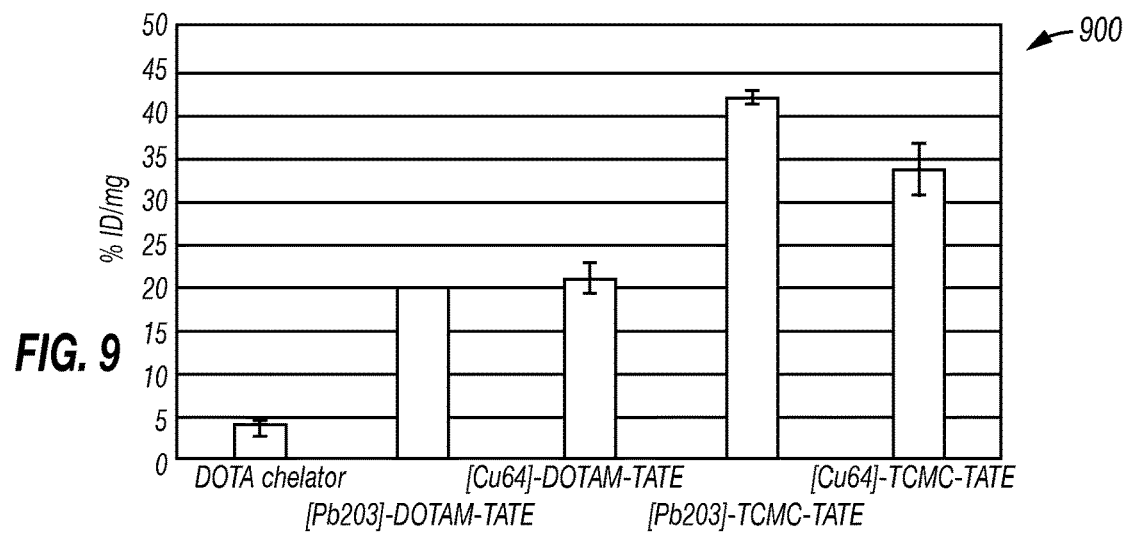
FIG. 9 is a graph depicting the cellular uptake (% ID/g) of $^{203}$Pb-DOTAMTATE and $^{203}$Pb-TCMCTATE in AR42J cancer cell lines.
Figure 10:
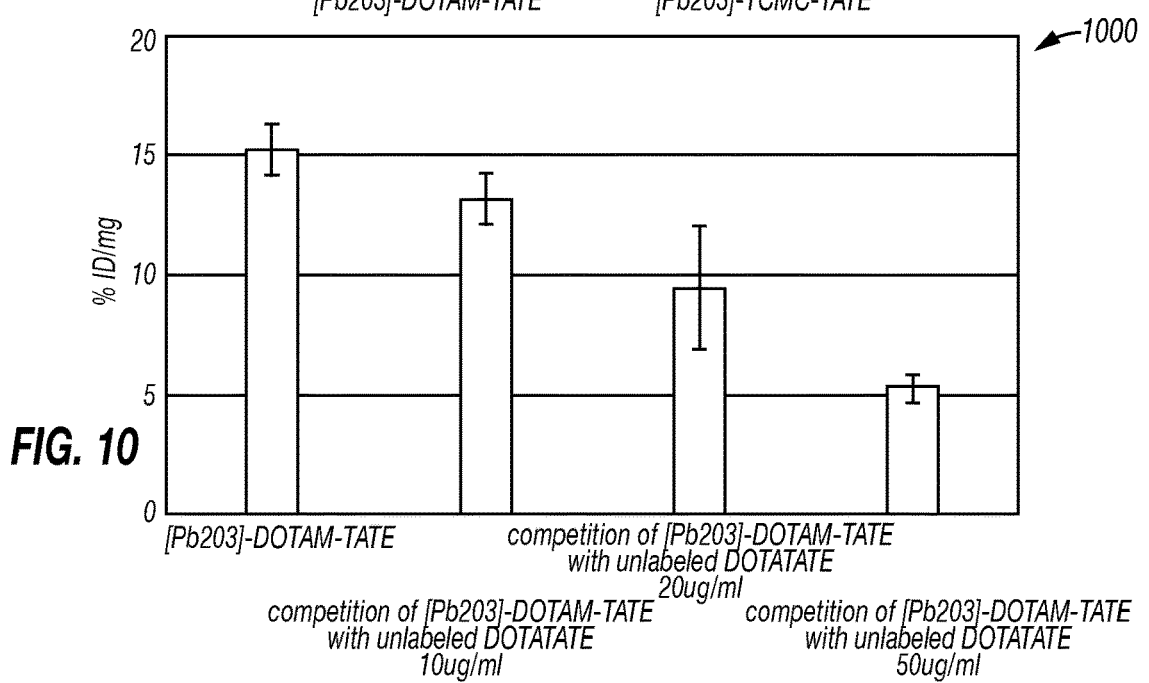
FIG. 10 is a graph depicting in vitro the cellular uptake and results of competition of $^{203}$Pb-DOTAMTATE and $^{203}$Pb-DOTATATE in AR42J cancer cell lines.
Figure 11:
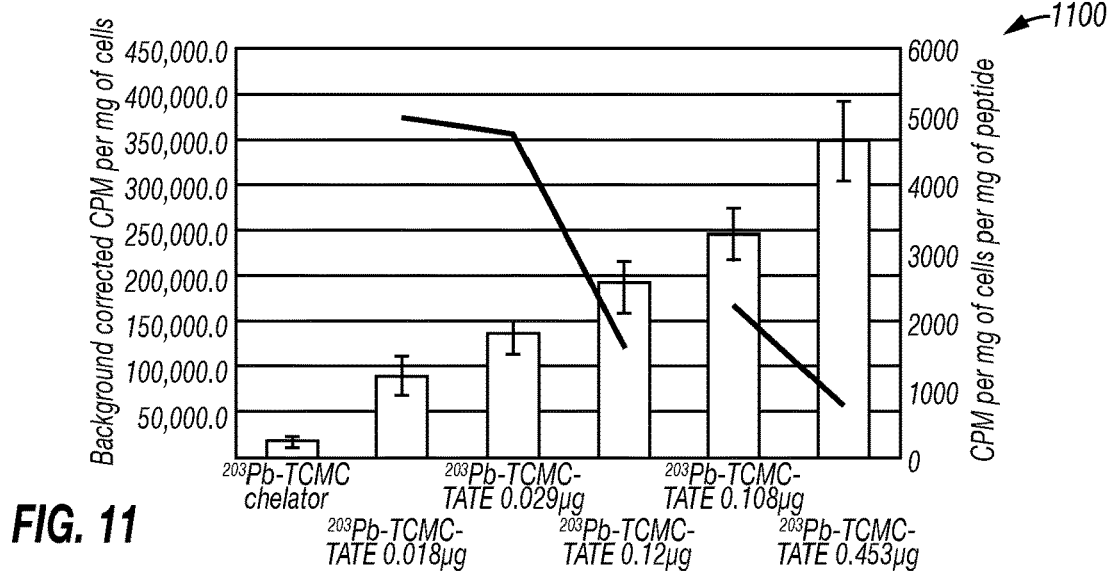
FIG. 11 is a graph depicting a comparison of the cellular uptake of $^{203}$Pb-DOTAMTATE and $^{203}$Pb-TCMCTATE and increasing accumulation of radiolabeled agents tested at various dosages of agents.

FIGS. 9-11 show test results demonstrating the SSTR targeting properties of radioisotope labeled DOTAMTATE and TCMCTATE. FIG. 9 shows an uptake study for $^{203}$Pb DOTAMTATE and TCMCTATE in comparison to $^{64}$Cu DOTAMTATE and TCMCTATE. FIG. 9 is a bar graph 900 depicting the percent initial dose per milligram (% ID/mg) (y-axis) for various chelators (x-axis). In particular, the cellular uptake study includes $^{203}$Pb-labeled and $^{64}$Cu-labeled DOTAMTATE and TCMCTATE (10 µg of agent labeled with 37 MBq (1 mCi) of isotope; 888 kBq (24 µCi)/well) in AR42J cancer cell line (100,000 cell per well) incubated for 1.5 h at 37° C. in ATCC®-formulated F-12K medium containing 20% fetal bovine serum (FBS). The DOTA chelator (e.g., DOTA without a targeting moiety or radioisotope) serves as a negative control in this study.

The TCMCTATE and DOTAMTATE chelators indicate stable chelation of both $^{203}$Pb and $^{64}$Cu isotopes. The graph 900 shows that the SSTR-selectivity of both $^{203}$Pb-labeled and $^{64}$Cu-labeled TCMCTATE and DOTAMTATE conjugates with specificity toward AR42J cancer cell lines (which express the SSTR). The $^{64}$Cu-conjugates show a similar rate of uptake and accumulation in AR42J cell lines as the $^{203}$Pb-conjugates and a similar selectivity toward SSTR in AR42J cell line. The in vitro accumulation of $^{203}$Pb-DOTAMTATE and $^{203}$Pb-TCMCTATE in the AR42J cancer cell line are, respectively, 21.4±2.26% ID/mg and 33.41±0.49% ID/mg. Similar trends in accumulation of both are observed for their $^{64}$Cu-labeled analogs, including the accumulation of $^{64}$Cu-DOTAMTATE is 33.41±0.49% ID/mg, and the accumulation for $^{64}$Cu-TCMCTATE is 41.59±1.79% ID/mg. This indicates that radiolabeled DOTAMTATE and TCMCTATE selectively accumulate in SSTR expressing cancer cells.

FIG. 10 shows a competition study of $^{203}$Pb DOTAMTATE and unlabeled DOTATATE (DOTATATE without a radioisotope). FIG. 10 is a graph 1000 of the cellular uptake (% ID/mg) (y-axis) for various chelators (x-axis). This figure shows in vitro uptake and competition study performed by addition of increasing amounts of unlabeled DOTATATE (5 µg/well) (DOTATATE without a radioisotope) together with $^{203}$Pb-DOTAMTATE. Both compositions show SSTR-specific accumulation in tested cancer cells. The competition studies uses $^{203}$Pb-DOTAMTATE (5 µg of agent labeled with 17 MBq (0.46 mCi) of $^{203}$Pb; 370 kBq (10 µCi)/well) with unlabeled DOTATATE (DOTATATE with no radioisotope) in the AR42J cancer cell line (100,000 cell per well) incubated for 2 h at 37° C. in ATCC-formulated F-12K Medium containing 20% FBS. The competition studies are performed by co-incubation of increasing amounts of unlabeled DOTATATE (10 µg/ml; 20 µg/ml; 50 µg/ml) together with $^{203}$Pb-DOTATATE.

FIG. 10 indicates an inverse relationship between the uptake of $^{203}$Pb-DOTAMTATE in AR42J cancer cells and the amount of its competitor, in this case unlabeled DOTATATE, when the two are co-incubated. The accumulation of $^{203}$Pb-DOTAMTATE is reduced in the presence of increasing amounts of DOTATATE (10 µg/ml, 20 µg/ml, 50 µg/ml) by 14%, 36%, 65% respectively. This indicates that DOTAMTATE is binding to the same SSTR receptors as DOTATATE.

FIG. 11 shows an uptake comparison of $^{203}$Pb-DOTAMTATE and $^{203}$Pb-TCMCTATE with increasing dosages of both compositions. These figures indicate the SSTR-targeting properties of radiolabeled-TCMCTATE and DOTAMTATE in cellular uptake studies performed in SSTR-positive AR42J pancreatic cancer cells (AR42J ATCC® CRL-1492™) and in competition studies done in the presence of unlabeled DOTATATE. FIG. 11 shows a graph 1100 depicting background corrected counts per minute (CPM) per mg of cells (y-axis) for various chelators (x-axis). This figure demonstrates the cellular uptake of $^{203}$Pb-TCMC- TATE and $^{203}$Pb-DOTAMTATE in the AR42J cancer cell line (100,000 cell per well). The AR42J cancer cells incubate for 3 h at 37° C. in ATCC™-formulated F-12K Medium containing 20% FBS.

$^{203}$Pb-TCMCTATE is prepared by labeling of the TCMC-TATE (10 µg) with either 37 MBq (1 mCi), 152 MBq (4.1 mCi) or 233 MBq (6.3 mCi) of the $^{203}$Pb radioisotope. The $^{203}$Pb-DOTAMTATE is prepared by labeling of DOTAMTATE (5 Gg) with either 5.1 MBq (0.14 mCi), 21.4 MBq (0.58 mCi) or 26.6 MBq (0.72 mCi) of the $^{203}$Pb isotope. The $^{203}$Pb-TCMC without a targeting moiety serves as a negative control in these studies.

The increased accumulation of $^{203}$Pb-TCMCTATE and $^{203}$Pb-DOTAMTATE in AR42J cells measured in CPM/mg of cells correlates with increasing amounts of octreotate conjugates added to the tested cells (0.018 µg, 0029 µg and 0.12 µg for TCMCTATE and 0.108 µg and 0.453 µg for DOTAMTATE). The bars represent values of the CPM per mg of cells (background corrected). The lines represent values of the CPM/mg of cells per mg of peptide conjugates used in the studies. As may be seen from the similar slopes of lines, both $^{203}$Pb-DOTAMTATE and $^{203}$Pb-TCMCTATE behave in similar manners with increasing concentration.

FIG. 11 suggests a direct correlation between accumulation of cancer targeting compositions in AR42J cancer cell line and the amount of the cancer targeting compositions used in the uptake studies. The uptake of both $^{203}$Pb-TCMCTATE and $^{203}$Pb-DOTAMTATE is increasing in the AR42J cancer cell line as the amount of $^{203}$Pb-DOTAMTATE and $^{203}$Pb-TCMCTATE added to the cancer cells is increased. These results indicate the SSTR-targeting properties of radioisotope labeled DOTAMTATE and TCMCTATE. Specificity is demonstrated by the saturation of the receptors as seen by the decrease in CPM/mg of cells per mg of peptide as the amount of peptide added increases.

In More Detail

Biodistribution Study in Athymic Mice Bearing AR42J Xenografts

Methods:

Female athymic nude mice (~20 g) are injected subcutaneously with 2×10$^6$ AR42J cells in 50% RPMI media and 50% Matrigel. Tumors are grown until an approximate tumor volume of 300 mm$^3$ is reached. Doses of $^{212}$Pb-DOTAMTATE are prepared (5 µCi) in phosphate buffered saline (PBS) and 200 µl is administered to the mice via intravenous injection. The animals are sacrificed at predetermined timepoints of 1 hour, 4 hours and 24 hours post drug injection. Tissues are collected from each animal and evaluated for amount of radioactive material in each organ by auto gamma counter. Specifically, organs are harvested, weighed and transferred to 12×55 mm polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Results and Conclusions:

Tumor uptake exceeded 20% one hour after drug administration and remained constant through 4 and 24 hours. Other non-target organs showed the highest accumulation of drug at 1-hour post-injection but decreased significantly by 24 hours post administration. The pancreas and kidneys are the two organs with the highest non-target uptake but these organs also showed significantly less accumulation by 24 hours post-injection. This observation is not of concern based on the toxicology and efficacy data we have accumulated thus far. In addition, these organs have also shown high drug uptake in other nonclinical rodent studies involving alpha emitters which have not translated into adverse effects in human studies (Kratochwil et al., 2014; Norenberg et al., 2006).

Experiment 3—Biodistribution

Figure 12:
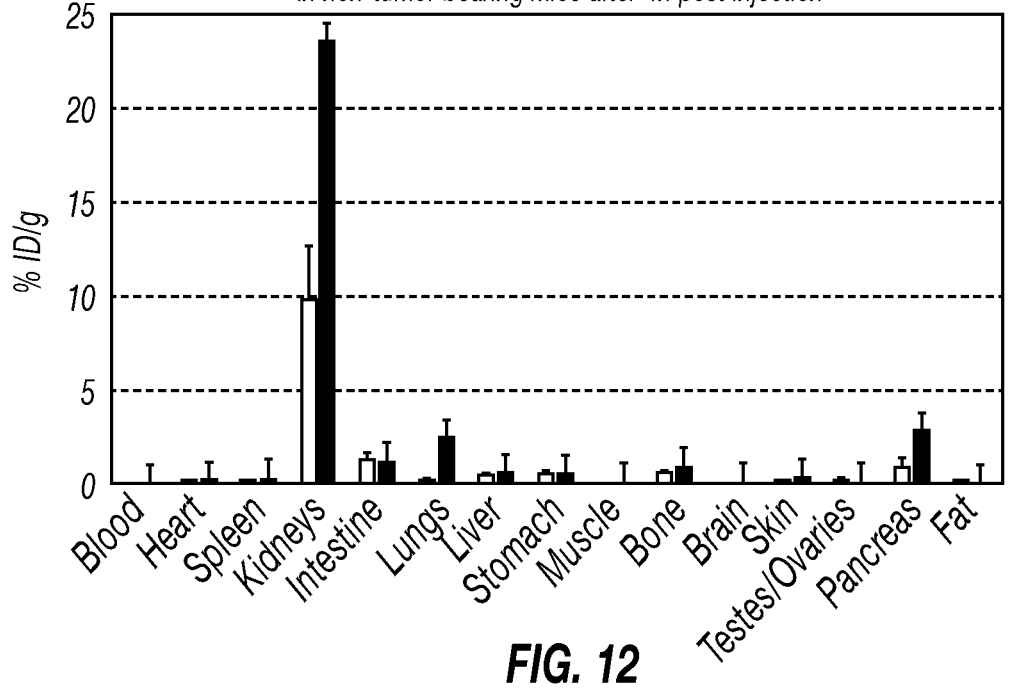
FIG. 12 is a graph depicting results of biodistribution of $^{203}$Pb-DOTAMTATE and $^{203}$Pb-TCMCTATE in non-tumor bearing mice as determined post injection.
Figure 13:
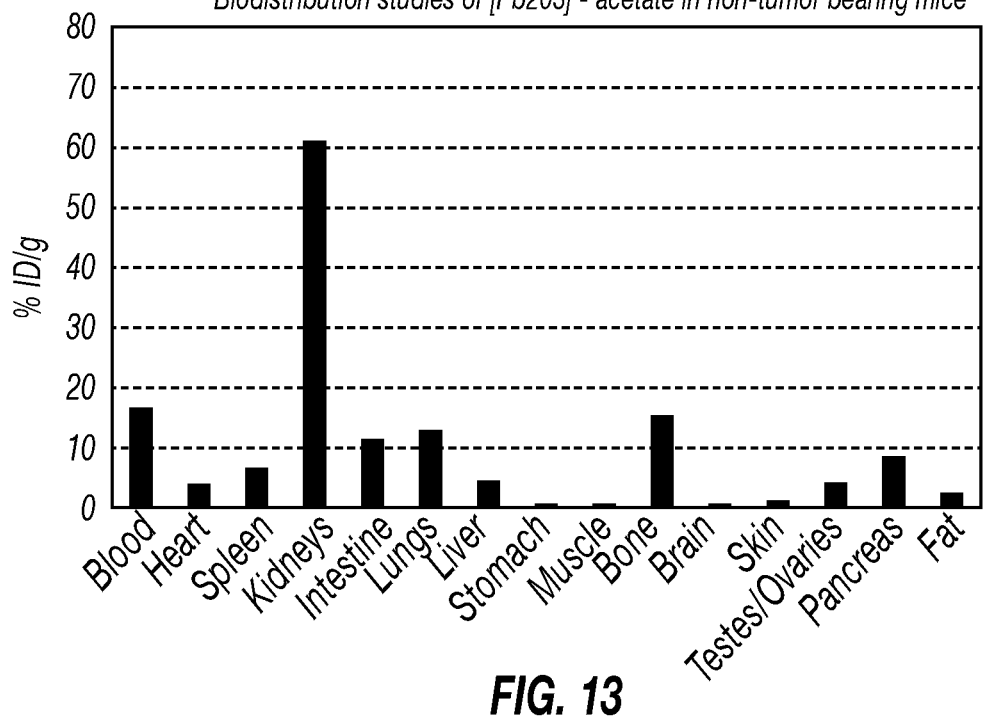
FIG. 13 is a graph depicting results of biodistribution of $^{203}$Pb Acetate in non-tumor bearing mice as determined post injection.

FIGS. 12-13 show biodistribution studies of cancer targeting compositions in the patient. FIG. 12 shows biodistributions for $^{203}$Pb-DOTAMTATE and $^{203}$Pb-TCMCTATE in non-tumor bearing mice. FIG. 13 shows the biodistribution of $^{203}$Pb-acetate, a radioisotope without either a chelator or targeting moiety in non-tumor bearing mice. These figures indicate biodistribution of the chelated radioisotopes is concentrated in the kidneys, thereby suggesting that the radioisotopes may be safer when chelated to DOTAMTATE and TCMCTATE.

FIG. 12 is a bar graph 1200 showing the biodistribution (% ID/g)(y-axis) for various organs (x-axis). The biodistribution of $^{203}$Pb-TCMCTATE and $^{203}$Pb-DOTAMTATE is shown for non-tumor bearing mice done at 4 h post-injection. The biodistribution studies of $^{203}$Pb-TCMCTATE and $^{203}$Pb-DOTAMTATE are completed in non-tumor bearing mice (CD-1 mice, Female, 20 g wt. 4-5 weeks) at 4 h post-injection of the cancer targeting compositions.

Both the $^{203}$Pb-DOTAMTATE and $^{203}$Pb-TCMCTATE show limited or no uptake in bone marrow, liver, or other organs, thereby indicating radiochemical stability of these particular cancer targeting compositions. The kidneys have increased accumulation of agents, while the retention of the cancer targeting compositions in other organs is lower than 2% ID/g (% of initial dose per gram of organ). Both compositions have similar pharmacokinetic properties and high radiochemical stability indicated by limited/no uptake of agents by bone marrow, liver and lung. In particular, the kidneys have higher retention of $^{203}$Pb-labeled TCMCTATE and $^{203}$Pb-DOTAMTATE at 23.53±1.54% ID/g and 9.79±2.9% ID/g, respectively. The high kidney retention of radiolabeled DOTATATE analogs reduces by co-administration of positively charged amino-acids during peptide receptor radionuclide therapy (PRRT). This indicates that the radioisotope remains tightly bound to the chelator-targeting moiety within the body, and that the cancer targeting composition does not bind to non-targeted cells.

In comparison, FIG. 13 is a graph 1300 (similar to the graph of FIG. 12), except that the biodistribution study is of $^{203}$Pb-acetate (a lead radioisotope without a chelator or targeting moiety) in non-tumor bearing mice done at 4 h post-injection. A higher accumulation of isotope is observed in blood, kidney, liver and lung compared to the chelated radioisotopes of FIG. 12. The biodistribution studies of the $^{203}$Pb-acetate indicate retention of the isotope in bone marrow, blood and liver after 4 h post-injection.

As may be seen by comparing FIG. 12 and FIG. 13, the organ distribution of $^{203}$Pb-DOTAMTATE and $^{203}$Pb-TCMCTATE (FIG. 12) is different than those observed for free $^{203}$Pb isotope (FIG. 13), thereby indicating the in vivo stability of lead isotopes chelated to DOTAMTATE and TCMCTATE.

Figure 14:
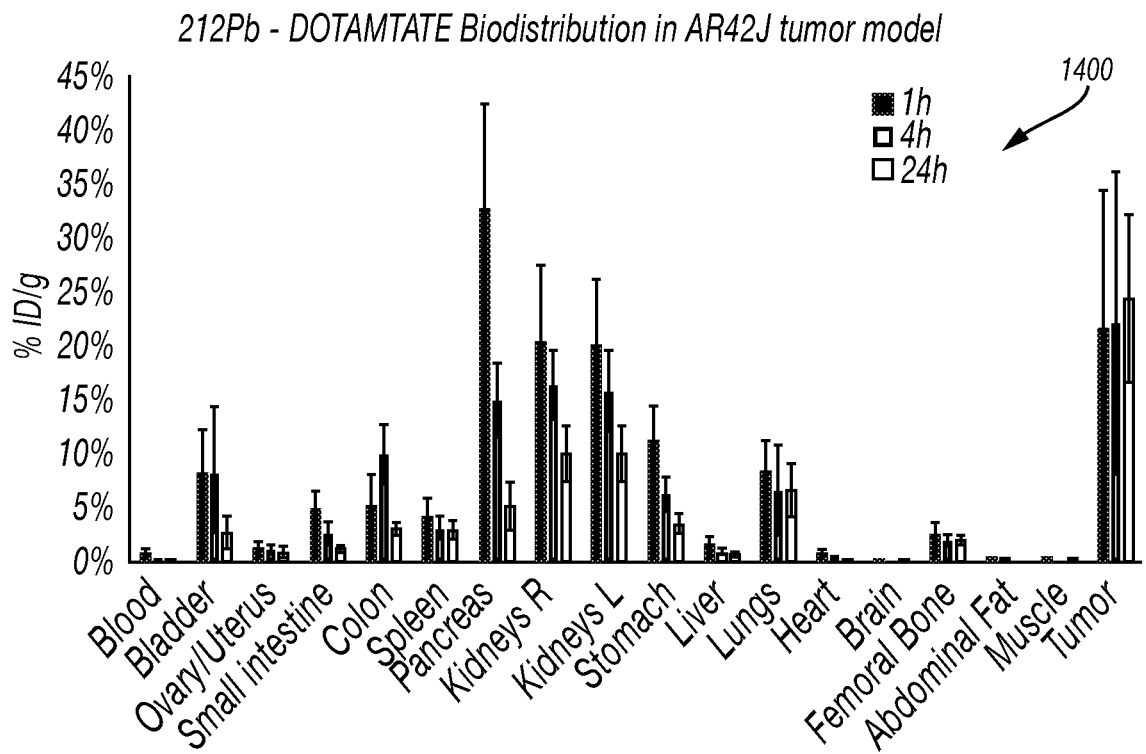
FIG. 14 is a graph depicting results of biodistribution of $^{212}$Pb-DOTAMTATE in AR42J tumor bearing mice over time.
Figure 15:
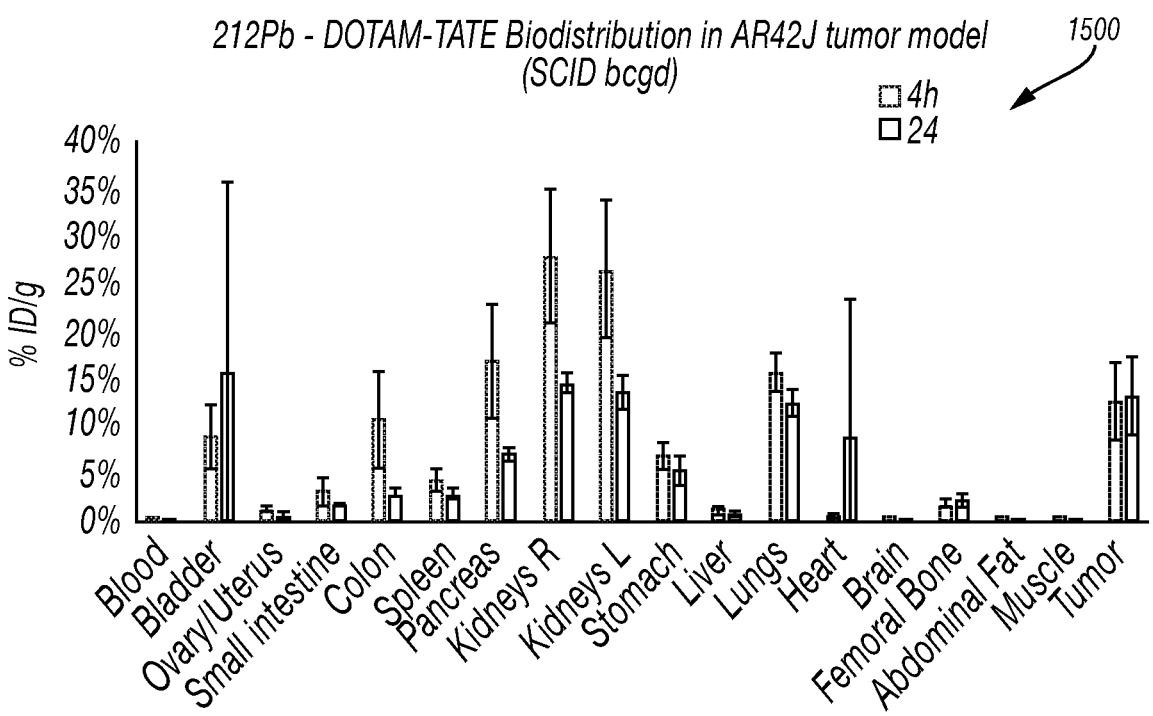
FIG. 15 is a graph depicting a comparison of results of biodistribution of $^{212}$Pb-DOTAMTATE in CB 17-SCID stain of AR42J tumor bearing mice over time.

FIGS. 14 and 15 show the biodistribution of $^{212}$Pb-DOTAMTATE in two different strains of AR42-J tumor bearing mice. These figures indicate some differences in organ distribution of the composition in the different strains of the tested mice.

FIG. 14 is a bar graph 1400 showing the biodistribution results (% ID/g) (y-axis) of the composition in various organs (x-axis) as a function of time. The graph represents the biodistribution results of $^{212}$Pb-DOTAMTATE in tumor bearing mice (AR42J tumor model) acquired at different time points (1 hour, 4 hours, and 24 hours) post injection (bars).

Similarly, FIG. 15 is a bar graph 1500 showing the biodistribution results (% ID/g) (y-axis) of the composition in various organs (x-axis). FIG. 15 shows biodistribution results of $^{212}$Pb-DOTAM-TATE in CB 17-SCID strain of AR42J mice done at 4 hours and 24 hours post injection (bars). This experiment is similar to the experiment of FIG. 14, except that for FIG. 15 the composition is administered to tumor bearing mice which also have severe combined immune deficiency (SCID).

As may be seen from FIGS. 14 and 15, the composition $^{212}$Pb-DOTAM-TATE accumulates in the SSTR-expressing tumor, and also in normal organs with known higher expression of SSTR such as the pancreas. The composition eliminates through bladder and kidneys which contributes to the higher retention of agent in these organs. Although there is variation in biodistribution of the composition between the strains of AR42J mice as shown on FIG. 14 and FIG. 15, in both cases there is accumulation and retention of composition in the tumor over time. This indicates that the composition may localize the SSTR-expressing tumors despite differences in strains of subjects, such as severe combined immunodeficiency (SCID).

Figure 16:
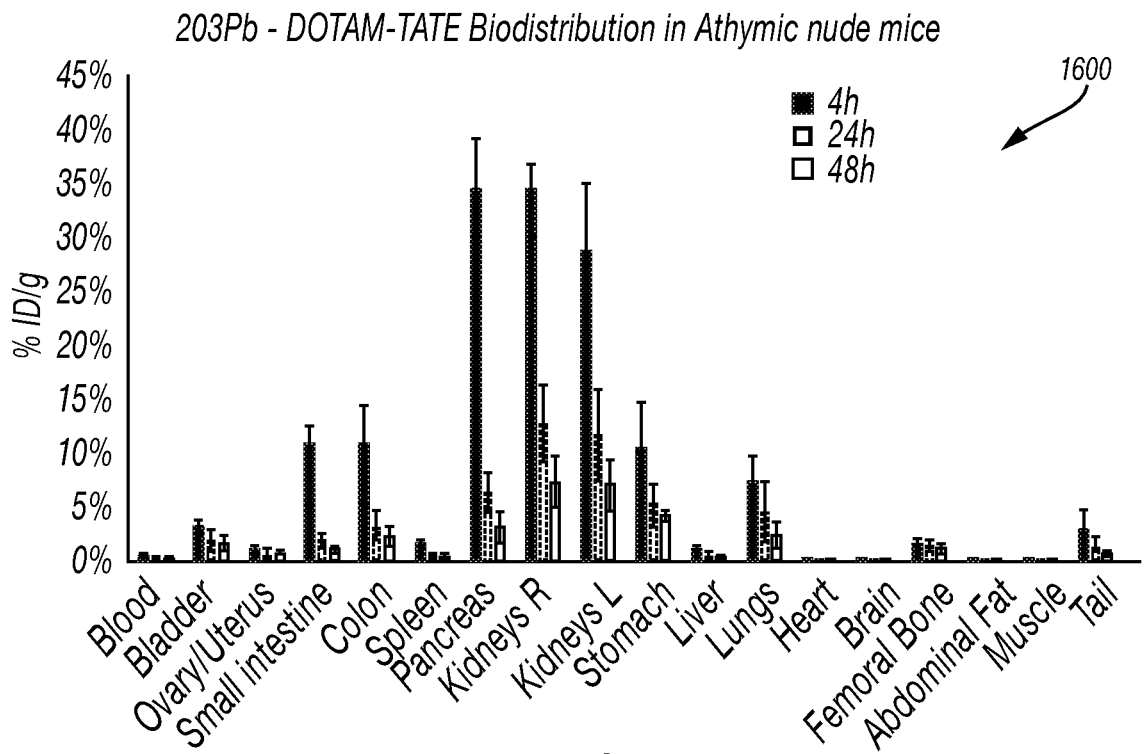
FIG. 16 is a graph depicting results of biodistribution of $^{203}$Pb-DOTAMTATE in athymic nude mice over time.

FIG. 16 shows the results of biodistribution of $^{203}$Pb-DOTAMTATE in non-tumor bearing athymic nude mice over time. FIG. 16 is a bar graph 1600 showing the biodistribution results (% ID/g) of $^{203}$Pb-DOTAMTATE in various organs (y-axis). The biodistribution data are acquired at 4 h, 24 h, and 48 h post-injection. FIG. 16 shows that $^{203}$Pb-DOTAMTATE initially accumulates in the SSTR-expressing organ, such as the pancreas and stomach of non-tumor bearing athymic nude mice. There is also accumulation of the composition observed in kidneys and bladder due elimination of the composition through renal clearance. As may be seen from these figures, the composition is washed out from all measured organs over time in non-tumor bearing mice.

In More Detail $^{203}$Pb-DOTAMTATE Biodistribution in Athymic Nude Mice $^{203}$Pb-DOTAMTATE is examined by our group in both animal and human models and the use of $^{203}$Pb-DOTAMTATE as a surrogate for $^{212}$Pb-DOTAMTATE is the subject of a recent eIND (130,960).

Methods:

Female athymic nude mice (~20 g) are injected with a single dose of $^{203}$Pb-DOTAMTATE. Specifically, 10 µCi of $^{203}$Pb-DOTAMTATE is diluted in PBS and 100 µl is administered to the mice via intravenous injection. The animals are sacrificed at predetermined time points of 4 hr, 24 hours and 48 hours post drug injection. Tissues are collected from each animal and evaluated for amount of radioactive material in each organ by auto gamma counter. Specifically, organs are harvested, weighed and transferred to polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Results and Conclusion:

Referring to FIG. 16, organ uptake in athymic nude mice treated with $^{203}$Pb-DOTAMTATE is similar to what is seen with $^{212}$Pb-DOTAMTATE in this strain of mice: high initial uptake of the drug in the pancreas and kidneys that continues to decrease over time. This indicates that $^{203}$Pb-DOTAMTATE and $^{212}$Pb-DOTAMTATE act similarly in the body as expected given that they are the same peptide and metal.

Figure 17:
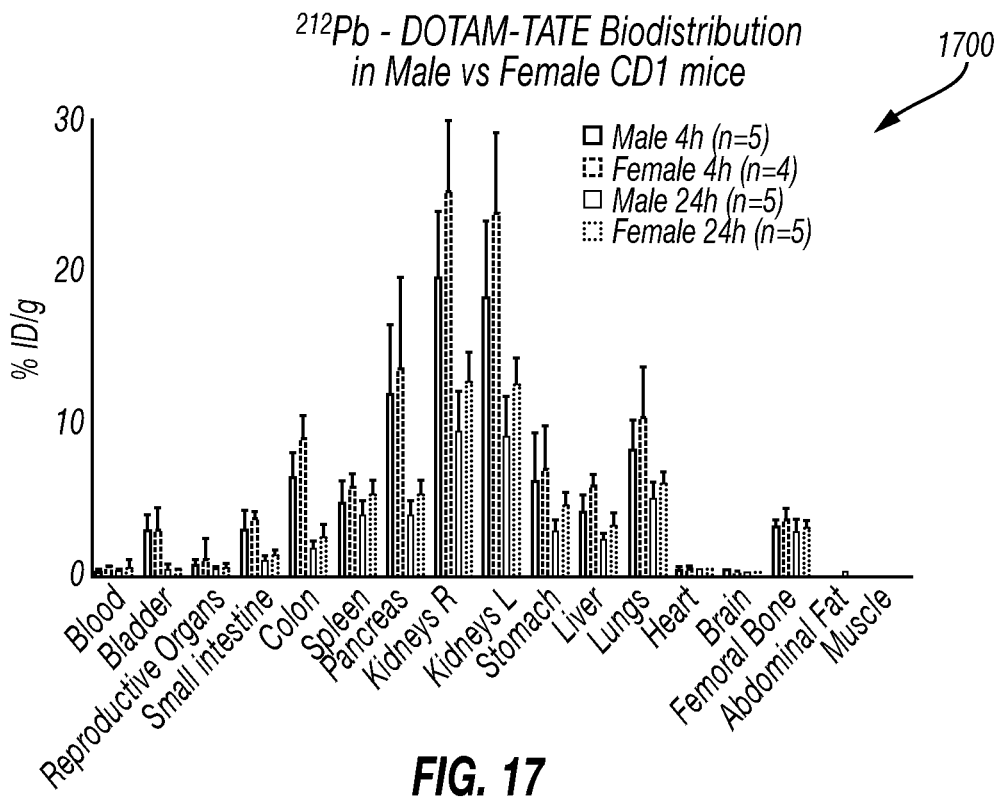
FIG. 17 is a graph depicting results of biodistribution of $^{212}$Pb-DOTAMTATE in female and male AR42J mice at 4 h and 24 h and FIG. 17B comparison of male and female kidney retention of octreotide over time.

FIG. 17 compares the biodistribution of $^{212}$Pb-DOTAMTATE in non-tumor bearing male and female mice. FIG. 17 is a bar graph 1700 showing the results of biodistribution (% ID/g) (y-axis) of the composition in various organs (x-axis). The biodistribution studies of $^{212}$Pb-DOTAM-TATE are done in both male and female in non-tumor bearing CD1 mice at both 4 h and 24 h post-injection. Both the male and female mice have similar pattern of biodistributions, indicating that the distribution of the compound is not strongly influenced by the gender of the subject.

In More Detail

Biodistribution of $^{212}$Pb-DOTAMTATE in Male and Female Non-Tumor Bearing Mice As a basis for selecting female mice for numerous studies and particularly in the GLP toxicity study, an extensive literature search is conducted to support that there is little difference between male and female mice. Furthermore, what little difference is observed shows higher sensitivity in female mice suggesting they would be the worst-case scenario between the two sexes (Lipnick et al., 1995) and as a result are more commonly used in safety evaluation (OECD, 2000).

Several clinical studies of $^{68}$Ga-DOTATATE PET/CT showed no differences in radiotracer distribution and its organ retention between male and female patients. However, the recent retrospective evaluation of data of 161 patients enrolled the clinical studies of $^{68}$Ga-DOTATATE PET/CT showed age and sex-related variations in the radiotracer accumulation in some organs (Watts, Singh, Shukla, Sharma, & Mittal, 2014). Female patients (n=31) demonstrated (p<0.05) higher standardized uptake value (SUV) in pituitary, thyroid, parotids, spleen and kidneys as compared to males (n=34).

The renal radioactivity in female rats injected with 111In-DTPA-octreotide showed a different localization pattern. Female rats showed higher uptake in the outer medulla compared with the cortex (Melis et al., 2007).

The kidney retention of radiotherapeutic agent can result in nephrotoxicity and kidney failure. The selection of female mice for toxicity studies allows a determination of the effect of $^{212}$Pb-DOTAMTATE on the kidney function especially in case of anticipated of higher retention of agent in female.

To better illustrate how this particular radiotherapeutic agent, $^{212}$Pb-DOTAMTATE, is similar between male and female mice, a biodistribution is conducted at two predetermined time points in CD-1 non-tumor bearing mice.

Methods:

Male and female CD-1 mice (~20 g) are injected with a single dose of $^{212}$Pb-DOTAMTATE. Specifically, 5 µCi of $^{212}$Pb-DOTAMTATE is diluted in PBS and 100 µl is administered to the mice via intravenous injection. The animals are sacrificed at predetermined time points of 4 hours and 24 hours post drug injection. Tissues are collected from each animal and evaluated for amount of radioactive material in each organ by auto gamma counter. Specifically, organs are harvested, weighed and transferred to polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Figure 17A:
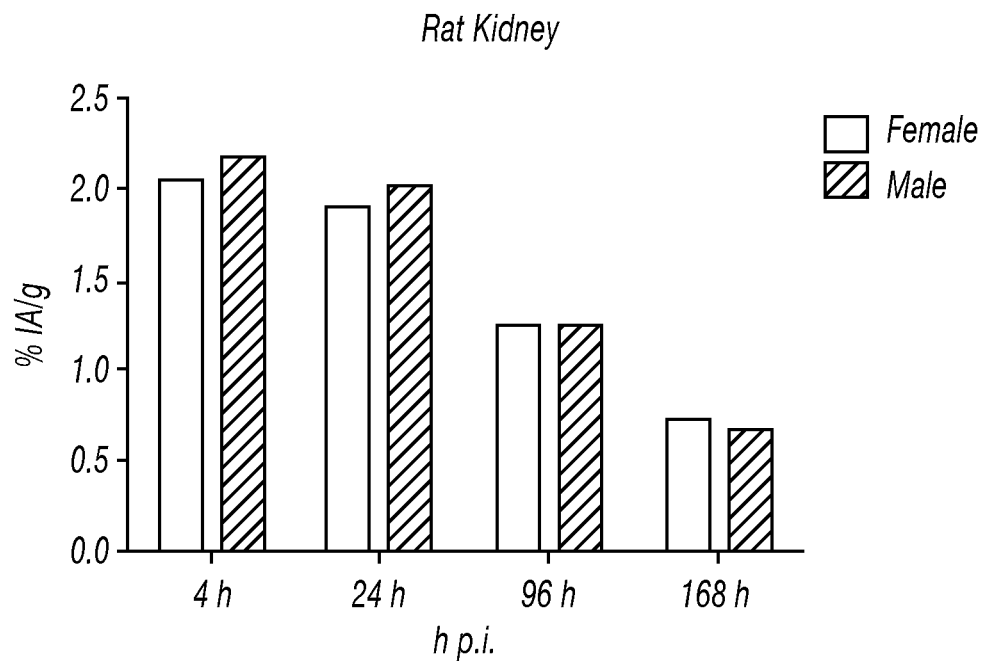
FIGS. 17A and 17B show graphs for a comparison of male and female kidney retention of octreotide over time. Mean uptake (% IA/g) of [111In-DTPA] octreotide in the kidneys of female and male rats (B) and mice (C) at 4, 24, 96 and 168 h pi. Rats (n=2 per group) received 6 MBq/0.5 µg radiolabeled peptide, and mice (n=4 per group) received 10 MBq/0.1 µg radiolabeled peptide. The difference in renal uptake between female and male mice was significant (P<0.001) at all time points (Melis et al., 2007).
Figure 17B:
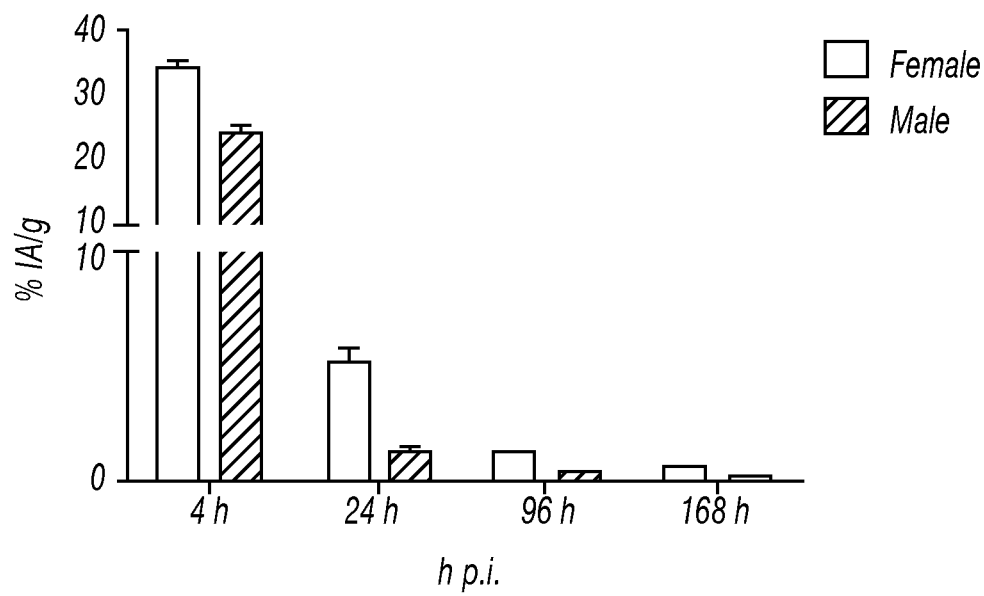

Results and Conclusions:

Referring to FIGS. 17A and B, there is no significant difference in the organ uptake of $^{212}$Pb-DOTAMTATE between male and female mice. There is a slight observable difference and this can be accounted for by the larger mass in males. Male and female mice had similar drug uptake in all organs at both 4 hour and 24 hours post injection. This slightly higher % ID/g and therefore absorbed dose in female mice further supports their use in toxicological studies.

Experiment 4—Efficacy

Figure 18:
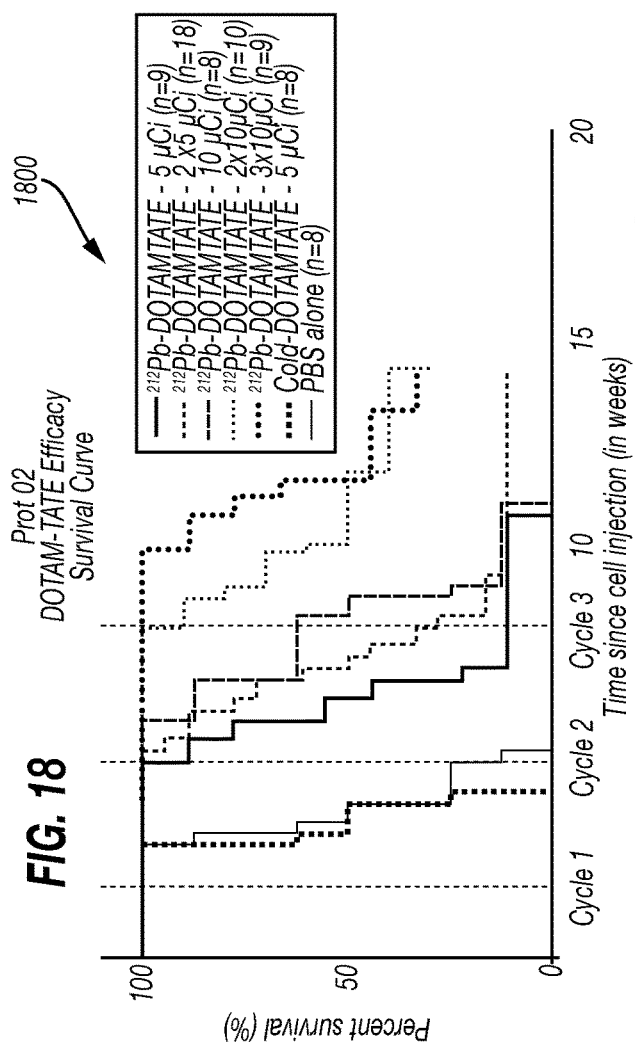
FIG. 18 is a graph depicting results of $^{212}$Pb-DOTAMTATE efficacy studies in a dose ranging experiment done in AR42J xenographs tumor-bearing mice over time.

FIGS. 18, 19A-B, and 20A-20E are experiments demonstrating the therapeutic efficacy of different dosages of $^{212}$Pb-DOTAMTATE administered in AR42J-tumor bearing mice. FIG. 18 shows a graph 1800 survival curve of AR42J-tumor bearing mice over time post-injection after administration of increasing doses of the composition. The graph 1800 plots the survival (% surviving) (y-axis) of tumor-bearing mice over time (weeks) (x-axis) as a function of $^{212}$Pb-DOTAMTATE dosage. FIG. 18 shows the survival curve for AR42J mice injected with either 185 kBq (5 µCi), 2×185 kBq (2×5 µCi), 370 kBq (10 µCi), 2×370 kBq (2×10 µCi), or 3×370 kBq (3×10 µCi) of $^{212}$Pb-DOTAMTATE. In addition, 2 control groups of mice are used who received either PBS (phosphate buffered saline) alone or non-radiolabeled cold-DOTAMTATE. The percentage of surviving mice in each of these groups is determined as a function of time. The graph indicates that increasing dosage of $^{212}$Pb-DOTAMTATE correlates with increased survival rate of the mice. All groups of mice who received the composition have a higher survival rate compared to the survival rate of control groups.

Figure 19B:
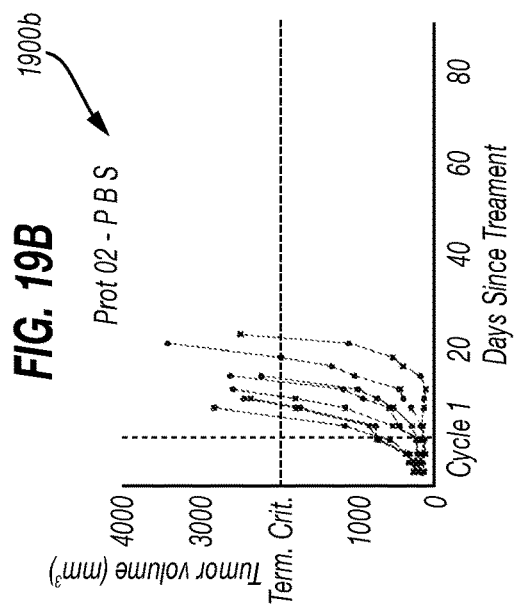
FIGS. 19A-19B are graphs depicting an effect of a control (cold DOTAMTATE or phosphate buffer-PBS) on tumor growth volume for each xenograph mouse.
Figure 19A:
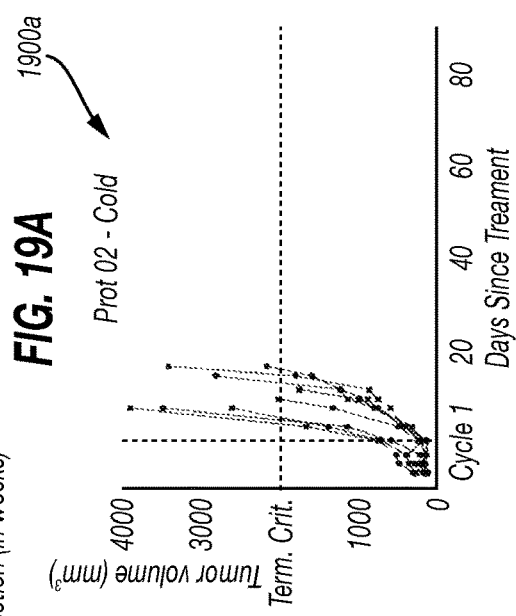
Figure 20A:
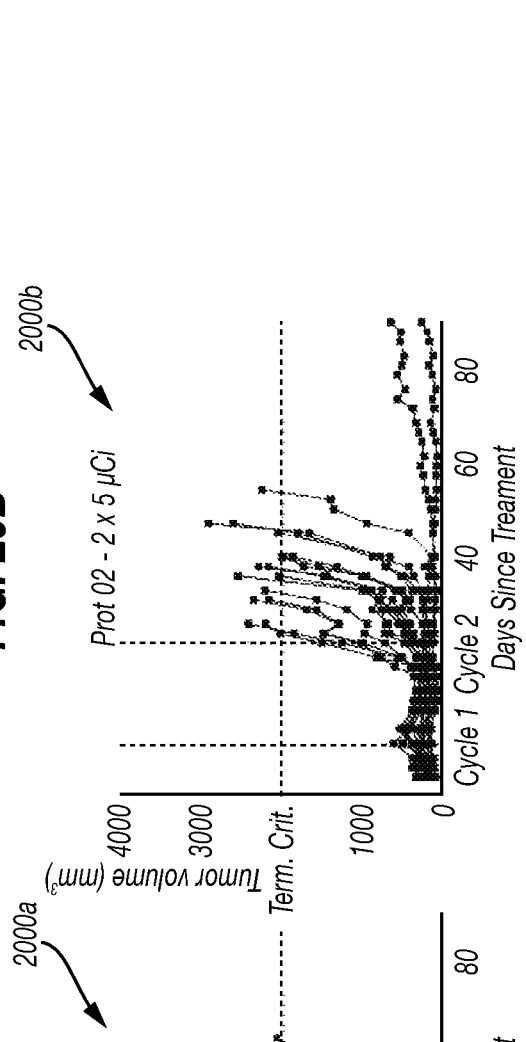
FIGS. 20A-20E are graphs depicting results of the effect of $^{212}$Pb-DOTAMTATE dose on tumor growth volume for each xenograph mouse.
Figure 20B:
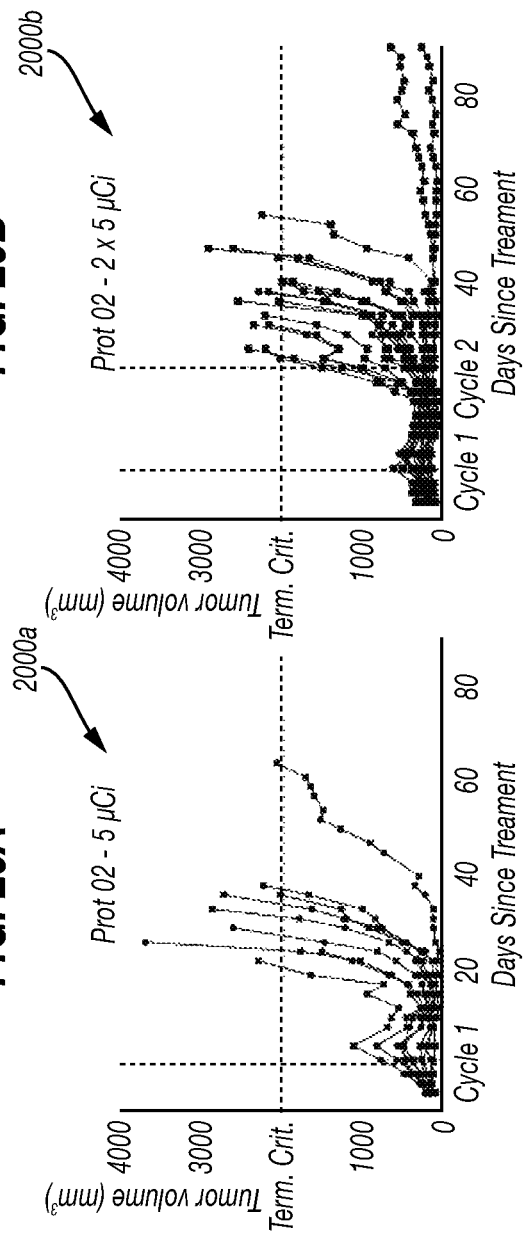
Figure 20C:
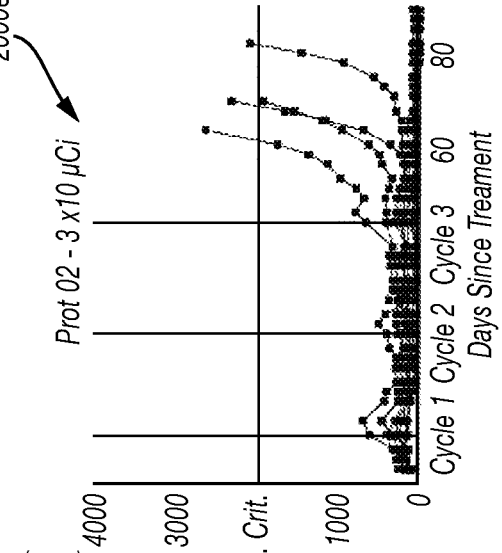
Figure 20D:
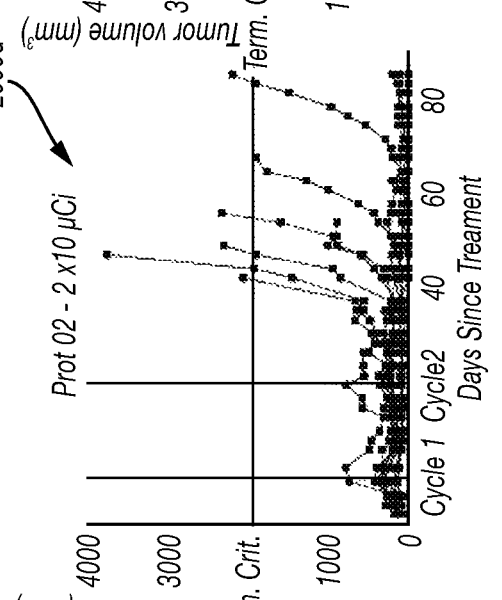
Figure 20E:
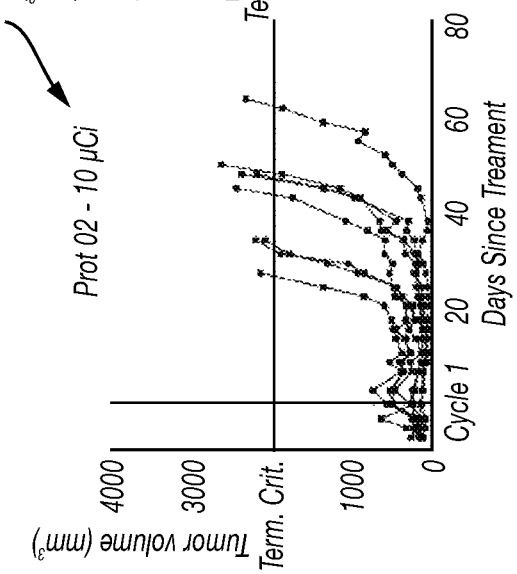

FIGS. 19A-B and 20A-E show the changes in tumor volume of individual mice in tested groups as a function of time and injected dose. FIGS. 19A-20E are graphs 1900a-2000e showing changes in the tumor volume (mm$^3$) (y-axis) over time (x-axis) for individual mice in each tested groups after administration of different dosages of $^{212}$Pb-DOTAMTATE. FIGS. 19A-19B show graphs 1900a-1900b depicting PBS and cold-DOTAMTATE, respectively, used as negative controls, similar to the controls of FIG. 18.

FIGS. 20A-20E show graphs 2000a-e of the effect of $^{212}$Pb-DOTAMTATE dose on tumor volume that are determined in each tumor bearing AR42J mice injected with single dose of 185 kBq (5 µCi) (20A), two doses of 185 kBq (2×5 µCi) (20B), single dose of 370 kBq (10 µCi) (20C), two doses of 370 kBq (2×10 µCi) (20D), and three doses of 370 kBq of $^{212}$Pb-DOTAMTATE (3×10 µCi) (20E), respectively. Similar to the data in FIG. 18, FIGS. 20A-20E indicate that increased dosage of $^{212}$Pb-DOTAMTATE correlates with decreased tumor volume over time.

FIGS. 19A-19B and 20A-20E indicate that the composition may be effective in therapy of SSTR-expressing tumors. These experiments indicate that increased dosage of $^{212}$Pb-DOTAMTATE correlates both with increased survival rate and decreased tumor volume over time.

Based on the results of in vitro uptake in AR42J cells, competition studies with DOTATATE and the similar biodistribution profile of DOTATATE, DOTAMTATE, and TCMCTATE, including similar renal clearance, DOTAMTATE and TCMCTATE may be considered for further investigation in the exploratory clinical studies of cancer targeting compositions.

While the experiments provided herein use certain radioisotopes, the present disclosure is intended to apply to compositions including a variety of other radioisotopes. For example, the LET of α-emitting radioisotopes is such that they irradiate an area approximately of the size of a cancer cell or small cluster of cancer cells. This indicates that little to no excess radiation may be emitted beyond the targeted cancer cells(s). In comparison, other radioactive emissions can travel for long distances within a body, damaging non-targeted cells.

Additionally, because the data herein indicates the ability of the chelator, such as DOTAM, to coordinate the lead radioisotopes, the substitution of radioisotopes may be considered insignificant. As discussed herein, DOTAM and TCMC show limited to no dissociation of lead radioisotopes compared to other chelators, such as DOTA. This further indicates that stability of the radioisotope coordination by these chelators may be extrapolated to binding of the chelator to the radioisotope.

Figure 21:
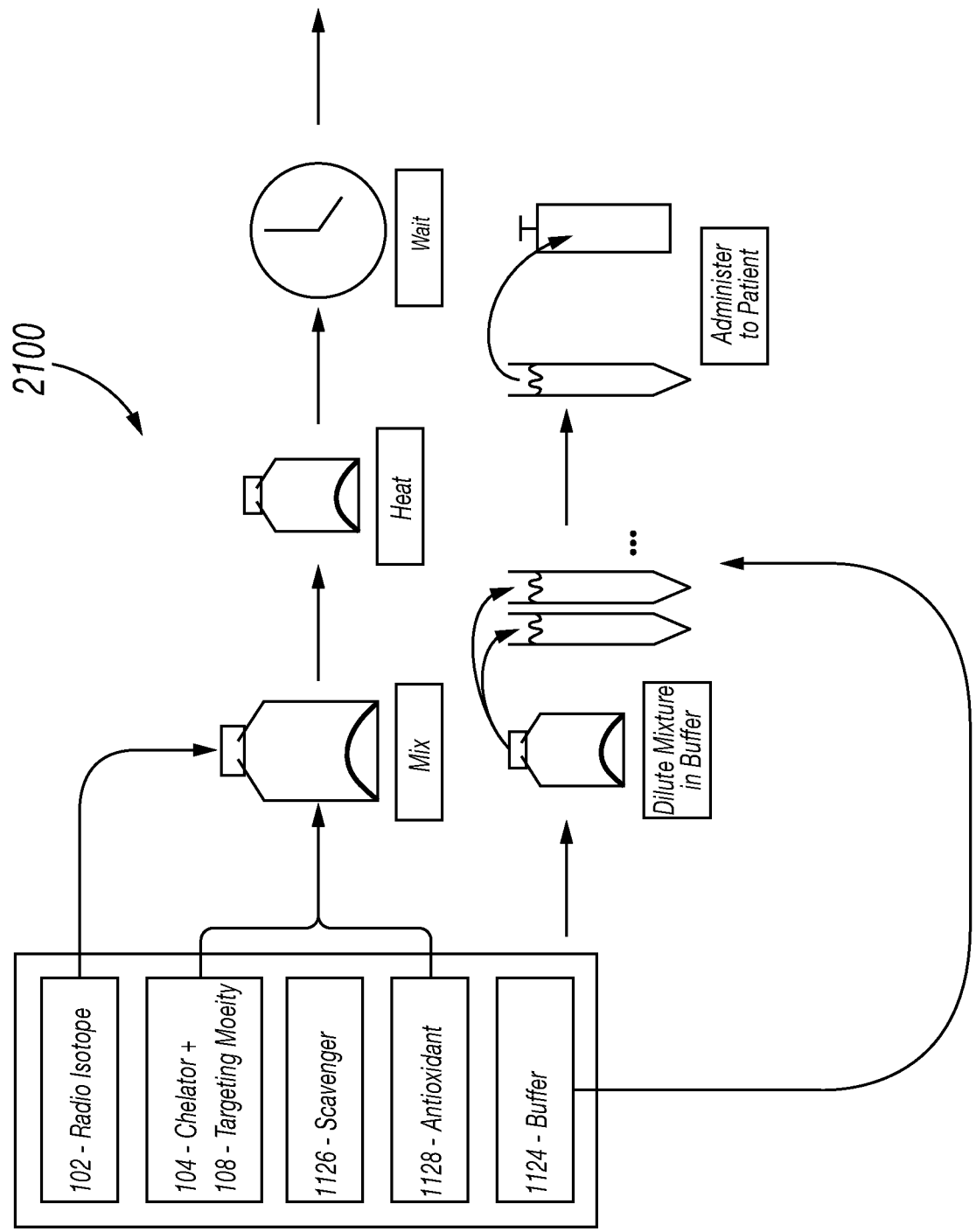
FIG. 21 is a schematic diagram depicting a kit and method of preparation of the cancer targeting composition for administration to a cancer patient.

FIG. 21 is a schematic diagram of a cancer treatment kit 2100 and associated method of making and/or using it. The kit 2100 includes the composition comprising a chelator 104 and targeting moiety 108 (e.g. DOTAMTATE, TCMCTATE, etc.), and a radioisotope 102 (e.g., $^{203}$Pb, $^{212}$Pb, etc.), such as those described herein (see, e.g., FIGS. 5A-6C). The composition may be mixed with a buffer 1124 (e.g. ammonium acetate, etc.). The mixture may include, for example 25-50 µg of the cancer targeting composition and 0.4M of ammonium acetate.

The kit may also contain an optional scavenger (e.g., diethylenetriamino-pentaacetic (DTPA), Ethylene Diamine Tetraacetic Acid (EDTA), DOTA, etc.) 1126 and/or antioxidant 1128 (e.g., ascorbic acid, gentisic acid, ethanol, vitamin C, etc.). Various additives may optionally be provided as needed for various applications. As also indicated by the diagram, the composition may be mixed alone or in combination with the other components and administered to the patient.

The method may also involve optional mixing and/or heating. The temperature and duration of the heating may change based on the components of the kit. For example, when the chelator is DOTAM, the mixture may be heated to room temperature for 15 minutes. In another example, when the chelator is DOTA, the mixture may be heated to 85° C. for 15 minutes.

The kits may be used, for example, for preparing a radiopharmaceutical preparation. The kit may include a sealed vial or bag, or any other kind of appropriate container, containing a predetermined quantity of the composition. The components of the kit may be in any appropriate form, such as in liquid, frozen, dry form, and/or lyophilized form.

Figure 22:
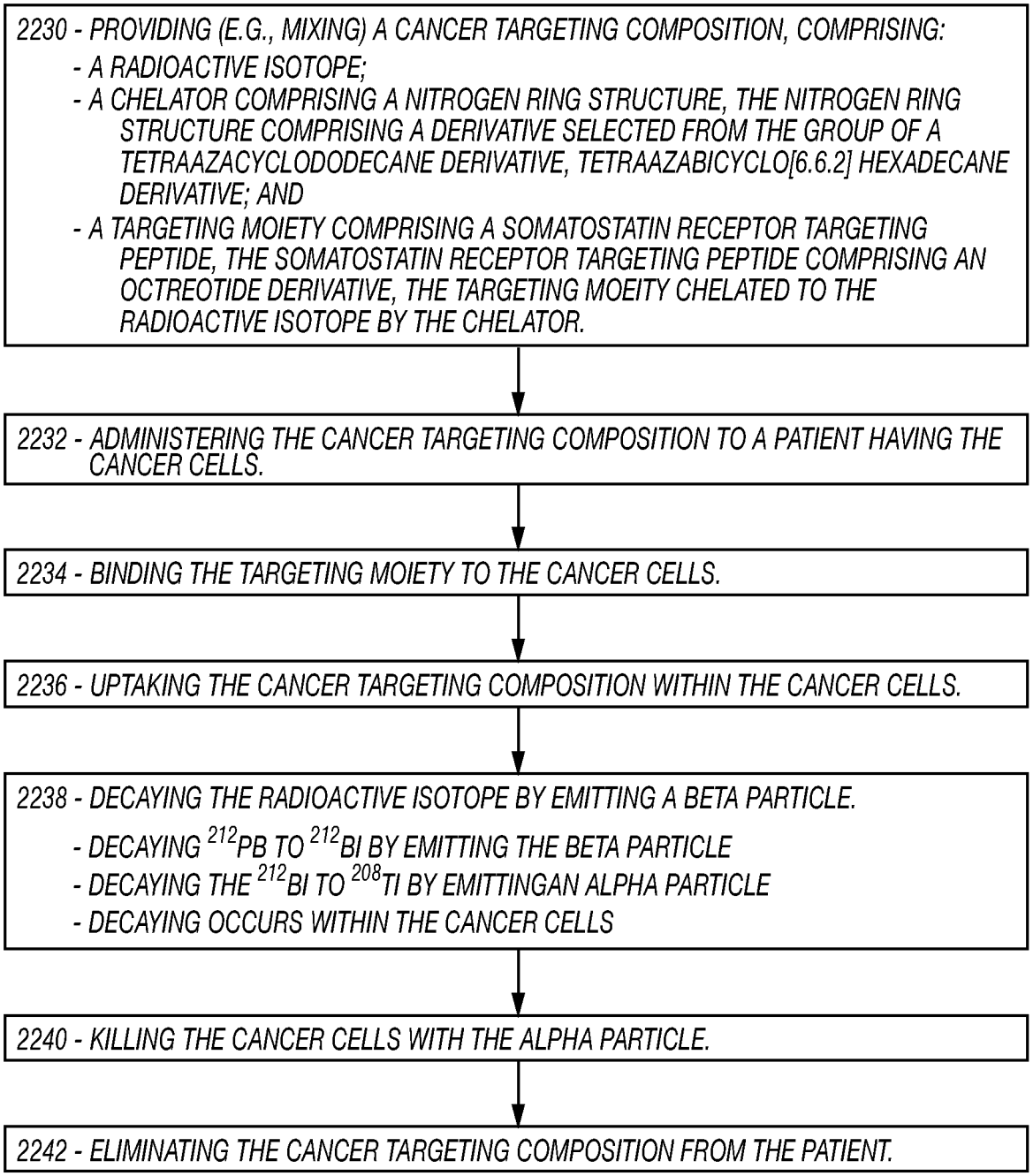
FIG. 22 is a flow chart depicting a method of targeted radiotherapy of cancer cells.

FIG. 22 is a flow chart depicting a method 2200 of targeted radiotherapy of cancer cells. The method involves 2230—providing (e.g., mixing) a cancer targeting composition, comprising: radioisotope, chelator, and a targeting moiety. The chelator comprises a nitrogen ring structure, the nitrogen ring structure comprising a derivative selected from the group of a tetraazacyclododecane derivative, a triazacyclononane derivative, and a tetraazabicyclo[6.6.2] hexadecane derivative. The targeting moiety comprises a somatostatin receptor targeting peptide. The somatostatin receptor targeting peptide comprises an octreotide derivative. The targeting moiety is chelated to the radioisotope by the chelator. The targeting composition may be any of those described herein. See, e.g., FIGS. 6B and 6C.

The method also involves 2232—administering the cancer targeting composition to a patient having the cancer cells, 2234—binding the targeting moiety to the cancer cells, 2236—uptaking the cancer targeting composition within the cancer cells, 2238—decaying the radioisotope by emitting a beta particle, and 2242—eliminating the cancer targeting composition from the patient. The decaying 2238 may involve decaying $^{212}$Pb to $^{212}$Bi by emitting the beta particle and decaying the $^{212}$Bi to $^{208}$Ti by emitting an alpha particle, decaying occurs within the cancer cells, and/or 2240—killing the cancer cells with the alpha particle.

In More Detail

Efficacy Study in Ar42J Xenograft Bearing Athymic Nude Mice Treated with $^{212}$Pb-DOTAMTATE Methods:

Two million (2×10$^6$) AR42J cells are implanted subcutaneously into the right flank of each mouse and tumors grew until an approximate tumor volume of 300 mm$^3$ is reached. Animals are then injected with 100 µl of 5 µCi or 10 µCi of $^{212}$Pb-DOTAMTATE, cold DOTAMTATE or PBS. Animals are monitored daily and calipered three times per week to monitor tumor volume. Mice are sacrificed when tumor volumes reached 2000 mm$^3$ or other predetermined termination criteria are met (weight loss over 15% for two consecutive days, serious bleeding, necrosis or ulceration of the tumor, scruffiness or lack of grooming over 5 days, lethargy over 3 days, weakness/balance issues over 5 days, hunchback appearance, diarrhea or hypothermia).

After three weeks, two-thirds of the remaining animals from the $^{212}$Pb-DOTAMTATE 10 µCi or $^{212}$Pb-DOTAMTATE 5 µCi groups receive a second round of injections with 10 µCi or 5 µCi of $^{212}$Pb-DOTAMTATE respectively. Monitoring and tumor volume data is collected for these mice as described above. Animals are maintained until a tumor volume of 2000 mm$^3$ or termination criteria mentioned above are met.

Three weeks later, one-half of the animals remaining in the 2×10 µCi $^{212}$Pb-DOTAMTATE receive a third injection of 10 µCi of $^{212}$Pb-DOTAMTATE. Monitoring and tumor volume data is collected for these mice as described above. Animals are maintained until a tumor volume of 2000 mm$^3$ or termination criteria mentioned above we met. Study is completed at 29 weeks post first injection.

Results and Conclusions:

Animals that are injected with cold-DOTAMTATE had a median survival of 3.4 weeks post injection. Animals that are treated with PBS only had a similar median survival at 3.5 weeks post injection. Mice that receive 1 injection of 5 µCi $^{212}$Pb-DOTAMTATE have a median survival of 6.3 weeks while mice who receive 1 injection of 10 µCi $^{212}$Pb-DOTAMTATE have a median survival of 8.5 weeks showing that a higher dose has a more efficacious effect. Animals who receive 2 injections of 5 µCi $^{212}$Pb-DOTAMTATE have a median survival of 7.1 weeks. The median survival time is similar between animals that receive 1×10 µCi vs 2×5 µCi of drug. Mice who receive 2 injections of 10 µCi $^{212}$Pb-DOTAMTATE had a median survival of 10.9 weeks with 20% of the mice tumor free at the end of the study. Mice who receive 3×10 µCi injections had a median survival of 11.6 weeks with 33% of the animals in this group being tumor free at the conclusion of the study (6 months). This suggests a dose dependent efficacious effect with repeat injections at levels where a single injection may have been toxic (see study NET0016). Kaplan-Meier survival curves summarizes the survival for each of the injection groups.

$^{212}$Pb-DOTAMTATE Binding Efficiency to SSTR Expressing Cells

Methods:

Peptide binding to somatostatin receptors 2 (SSTR2) and $K_d$ is evaluated in SSTR2 expressing AR42J cells by growing 250,000 cells into the wells of a 24-well plate for 48 hrs. Concentrations from 0.5 nM to 64 nM of $^{212}$Pb-DOTAMTATE are incubated in the AR42J containing wells for 10 minutes at 37° C. Four replicates are performed for each concentration. Cells are then washed with PBS and cells from each well are counted for presence of radioactivity. Binding curves are then created and $K_d$ calculated.

Figure 23:
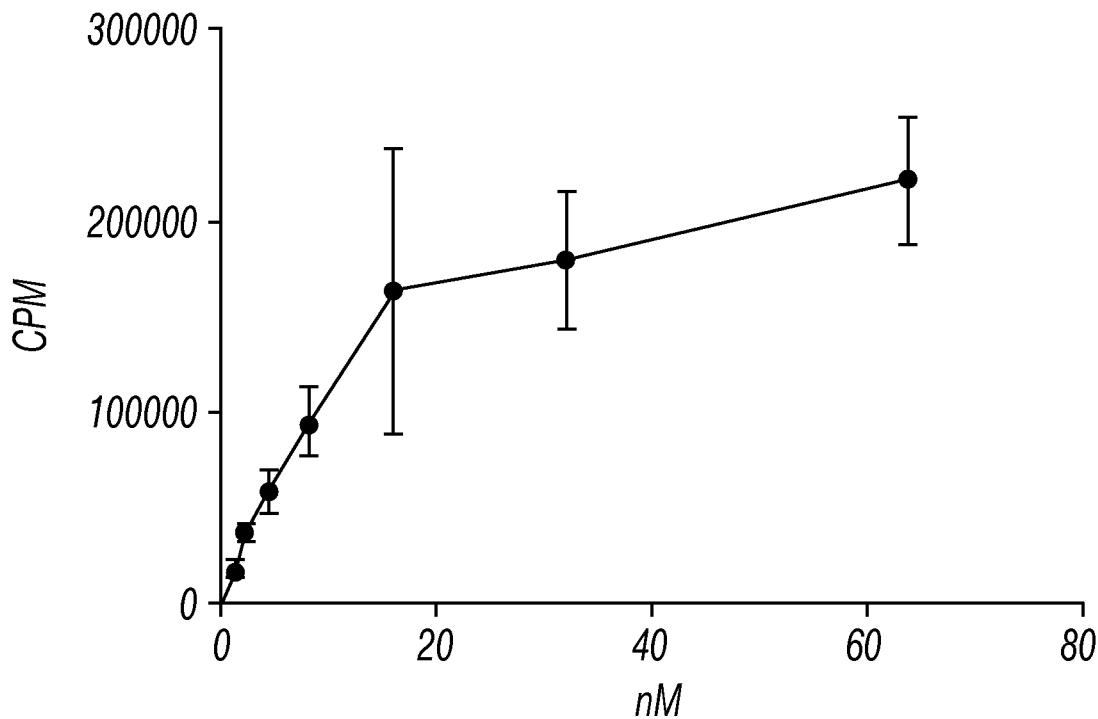
FIG. 23 is a graph of binding of $^{212}$Pb-DOTAMTATE to AR42J cells. Binding of 212Pb-DOTAMTATE to AR42J cells with increasing levels of drug measured as increasing counts per minute (cpm). Average of four wells per group and 250,000 cells per well.

Results and Conclusions:

Referring to FIG. 23, a one site total saturation binding curve is created using GraphPad Prism and a $K_d$ of 12.9 nM is determined. This is in line with what others have observed with DOTATATE (Ullrich et al., 2016). Therefore, we are seeing specific binding of $^{212}$Pb-DOTAMTATE to SSTR2 receptors on AR42J cells.

Cytotoxic Effect of $^{212}$Pb-DOTAMTATE on SSTR Expressing Cells

Methods:

Thirty-thousand (3×10$^4$) AR42J cells are grown in the wells of a 96 well plate for 2 days. Cells are then incubated for 4 hours with increasing doses of $^{212}$Pb-DOTAMTATE ranging from 0 nCi/ml to 800 nCi/ml. Eight wells per group are treated. Cells are washed with PBS to remove drug and then fresh media is introduced. Cells are allowed to incubate for 6 days at 37° C. Cells are then rinsed and incubated with fluorescein diacetate for 30 minutes and read with a fluorimeter at 485/535 nm. Percentage of viable cells is calculated based on untreated cells as a control.

Figure 24:
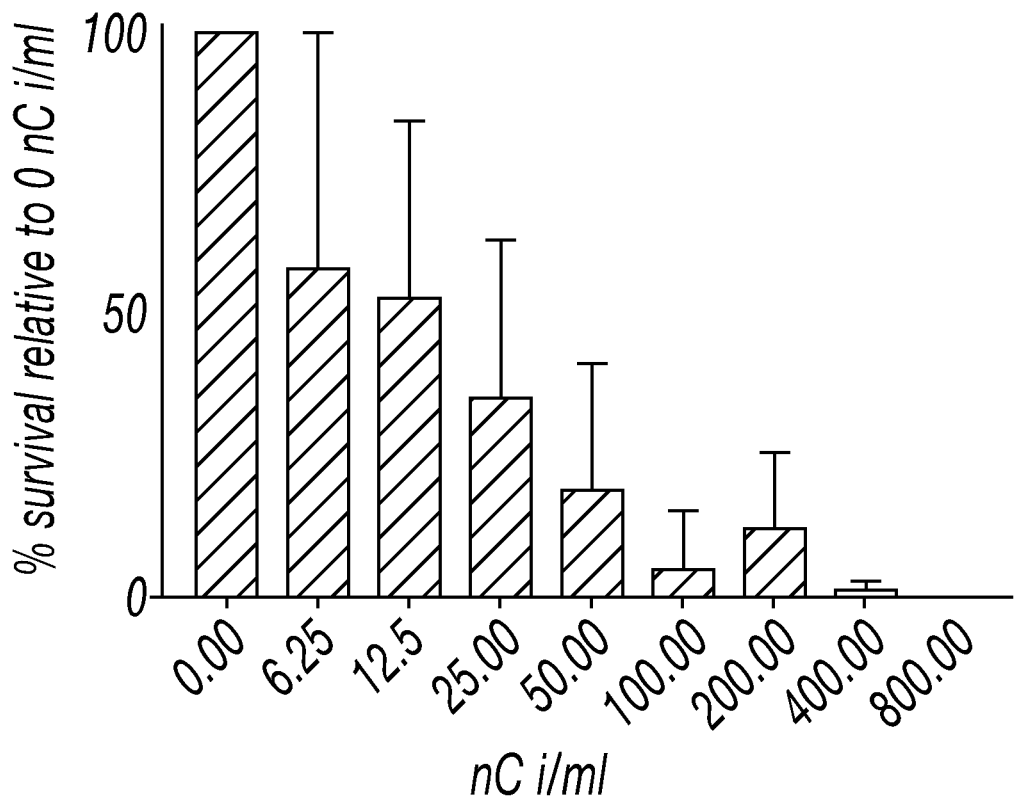
FIG. 24 is a graph of cytotoxicity of AR42J Cells Treated with $^{212}$Pb-DOTAMTATE. AR42J tumor size show a certain level of variability in an athymic nude strain. The three groups were organized such that each group had the same average tumor size. Outliers in each group are shown with an asterisk (*).

Results and Conclusions:

With reference to FIG. 24, a dose dependent cytotoxic effect can be seen with the complete cell death occurring at 800 nCi/ml. 50% viability is observed between 12.5 nCi/ml and 25 nCi/ml. This suggests targeted killing of the cells by the peptide showing specificity for SSTR2 receptors on AR42J cells. Cells treated with the negative control, DOTAM alone, do not show a dose dependent effect with viability ranging from 47% to 156% relative to untreated controls (data not shown). This suggests that chelate alone does not yield a dose dependent reduction in survival and is not specific for the SSTR2 receptors. Therefore, the peptide is required for proper and effective targeting and killing of cancer cells.

Correlation Between AR42J Tumor Volume and Drug Uptake

Figure 25:
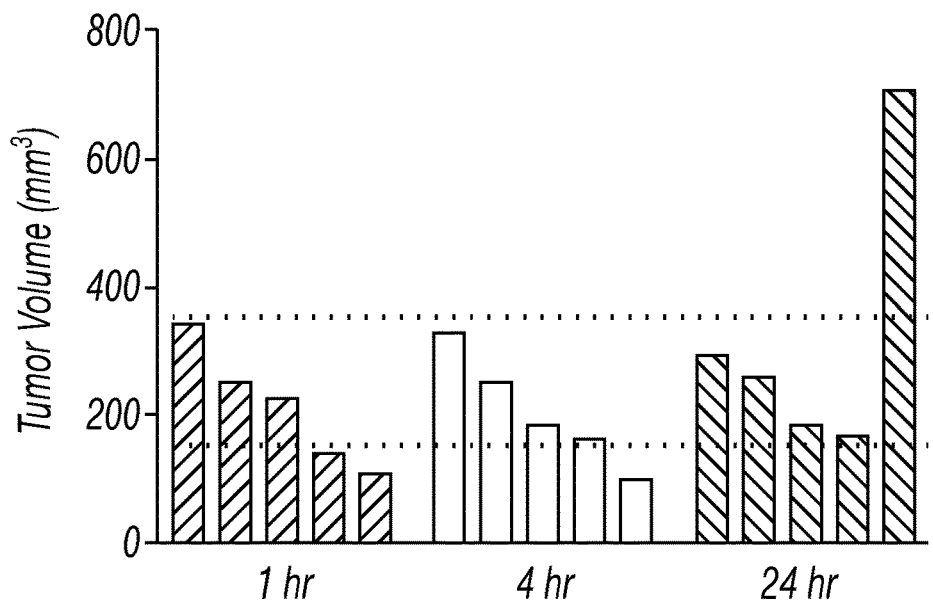
FIG. 25 is a graph of AR42J tumor volume on injection day. AR42J tumor size show a certain level of variability in an athymic nude strain. The three groups were organized such that each group had the same average tumor size. Outliers in each group are shown with an asterisk (*).

Methods:

AR42J tumor volumes in athymic nude mice from the study presented NET001 are calculated by measuring ½× length×width$^2$ with digital calipers on the day of drug administration. As shown in FIG. 25, a tumor volume of approximately 300 mm$^3$ is ideal but some variation did exist.

Figure 26:
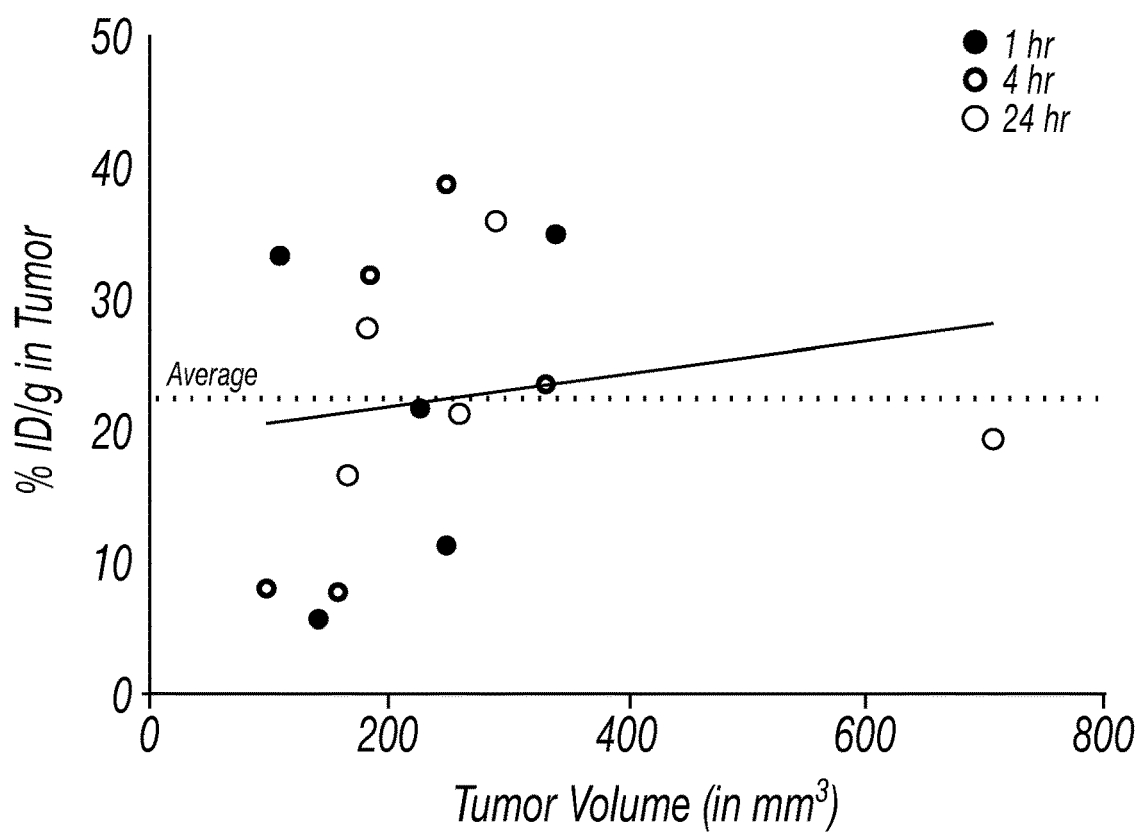
FIG. 26 is a graph of tumor uptake and tumor volume correlation. The % ID/g of each of the five animals in each timepoint group are shown (1 hr, 4 hr, 24 hr).

Results and Conclusions:

Referring to FIG. 26, despite variation in tumor sizes, there is no visible correlation between tumor size and percent injected dose per gram. The smallest tumor in one group had a high % ID/g compared to the larger tumors while the smallest tumor in another group had a low % ID/g relative to the larger tumors in that group. This suggests that tumor size variability does not translate to variability in tumor uptake.

Receptor Saturation does not Occur with Decreased Specific Activity in Athymic Nude Mice Methods:

Female athymic nude mice (~20 g) are injected subcutaneously with 2×10$^6$ AR42J cells in 50% RPMI media and 50% Matrigel. Tumors are grown until an approximate tumor volume of 300 mm$^3$ is reached. Doses of $^{212}$Pb-DOTAMTATE are prepared (10 µCi) at three different specific activities in PBS. 200 µl is administered to the mice via intravenous injection. The animals are sacrificed at 24 hours post drug injection. Tissues are collected from each animal and evaluated for amount of radioactive material in each organ by auto gamma counter. Specifically, organs are harvested, weighed and transferred to polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Figure 27:
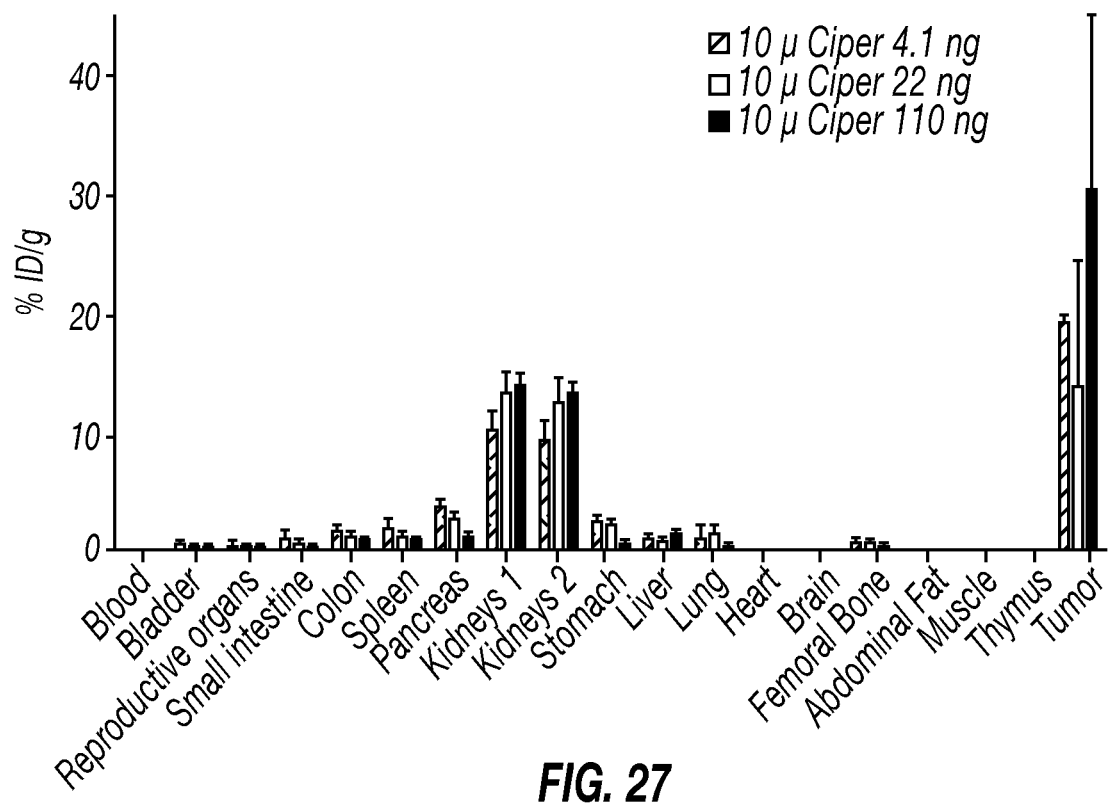
FIG. 27 is a graph of effect of specific activity on tumor uptake in athymic nude mice. % ID/g of each organ is shown at three different specific activities of 212Pb-DOTAMTATE: from left to right for each organ, 10 µCi per 4.1 ng, n=3, 10 µCi per 22 ng, n=4 and 10 µCi per 110 ng, n=3.

Results and Conclusions:

Referring to FIG. 27, three specific activities are examined in the biodistribution study. 10 μCi per 4.1 ng is used in most of the $^{212}$Pb-DOTAMTATE studies to date however a decrease in the specific activity does not appear to have a significant effect on tumor uptake. This suggests that receptor saturation is not occurring even at over 25-fold lower specific activity then what has been primarily used in these studies.

Efficacy Study in Ar42J Xenograft Bearing Athymic Nude Mice Treated with $^{212}$Pb-DOTAMTATE at Treatment Cycles of Two Weeks and Three Weeks Methods:

Two million (2×10$^6$) AR42J cells are implanted subcutaneously into the right flank of each mouse and tumors grew until an approximate tumor volume of 200-300 mm$^3$ is reached. Animals are then injected with 100 μl of 10 μCi $^{212}$Pb-DOTAMTATE or saline. Animals are monitored daily and calipered three times per week to monitor tumor volume. Mice are sacrificed when tumor volumes reached 3000 mm$^3$ or other predetermined termination criteria are met (weight loss over 15% for two consecutive days or 20% weight loss from initial weight, serious bleeding, necrosis or ulceration of the tumor, scruffiness or lack of grooming over 5 days, lethargy over 3 days, weakness/balance issues over 5 days, hunchback appearance, diarrhea or hypothermia).

After two or three weeks, the animals receive a second dose of 10 μCi $^{212}$Pb-DOTAMTATE. Monitoring and tumor volume data is collected for these mice as described above. Animals are maintained until a tumor volume of 3000 mm$^3$ or termination criteria mentioned above are met.

Two or three weeks later, the animals receive 10 μCi of $^{212}$Pb-DOTAMTATE. Monitoring and tumor volume data is collected for these mice as described above. Animals are maintained until a tumor volume of 3000 mm3 or termination criteria mentioned above we met. The study is ongoing.

Figure 28A:
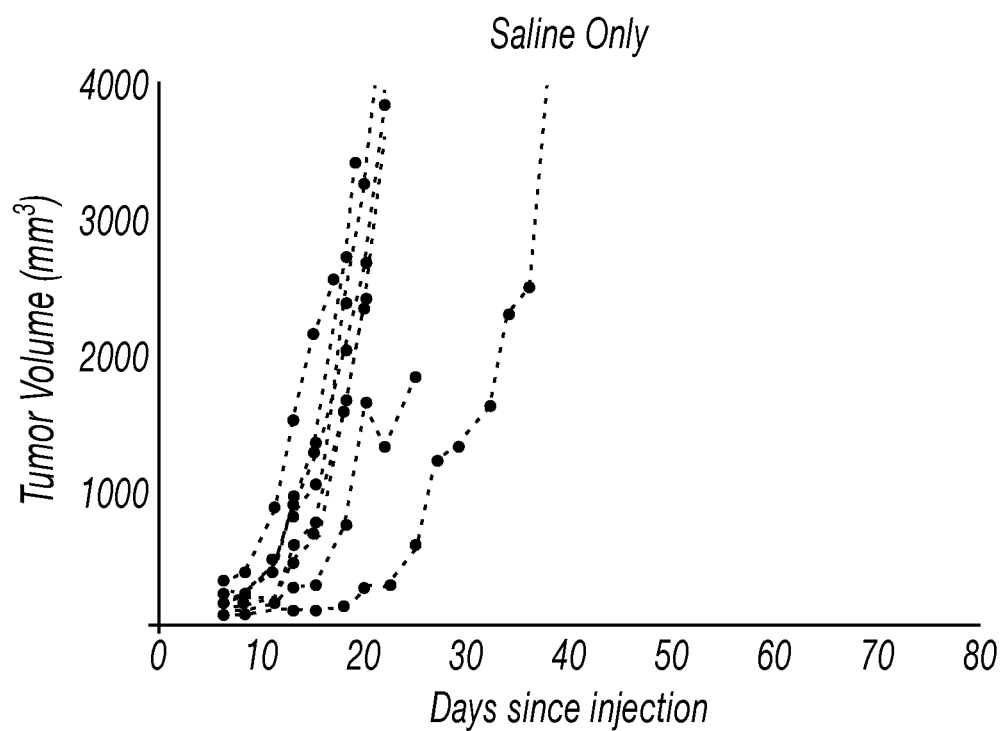
FIGS. 28A-28C are graphs of individual efficacy of mice treated with $^{212}$Pb-DOTAMTATE at two cycle intervals. The Figures show.
Figure 28B:
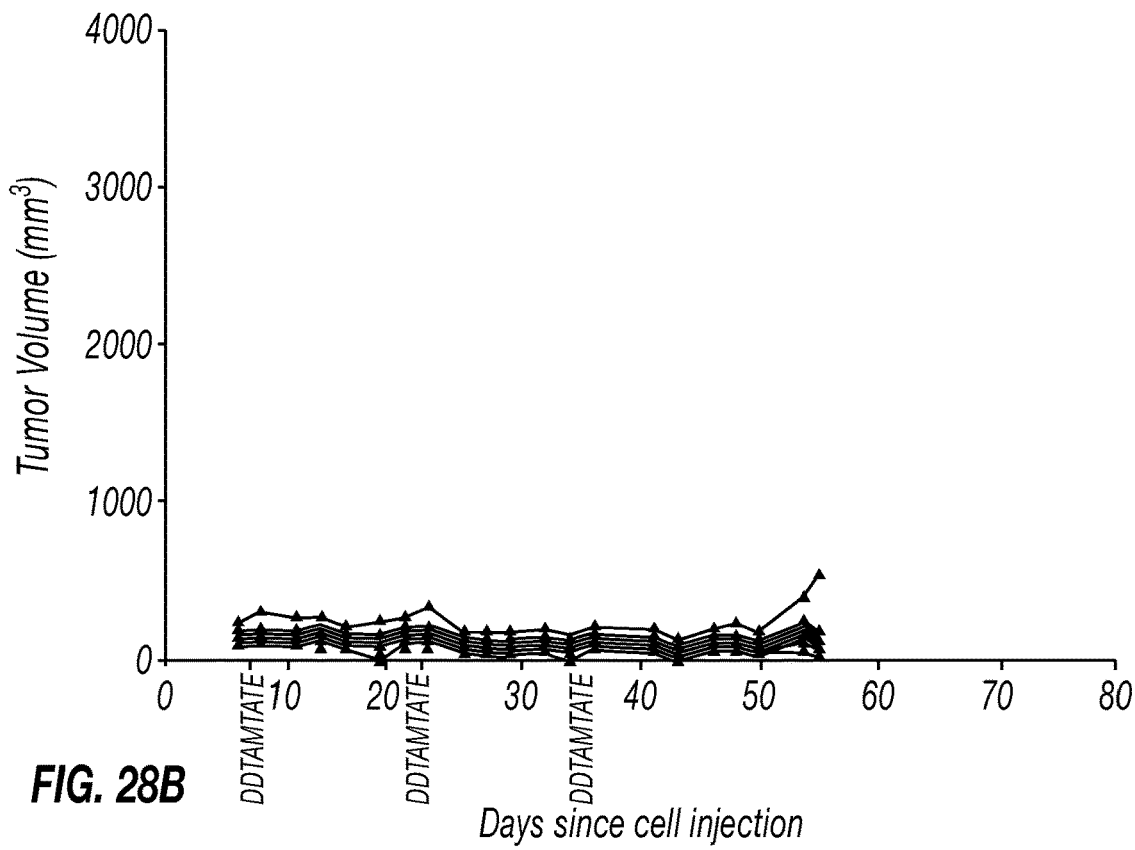
Figure 28C:
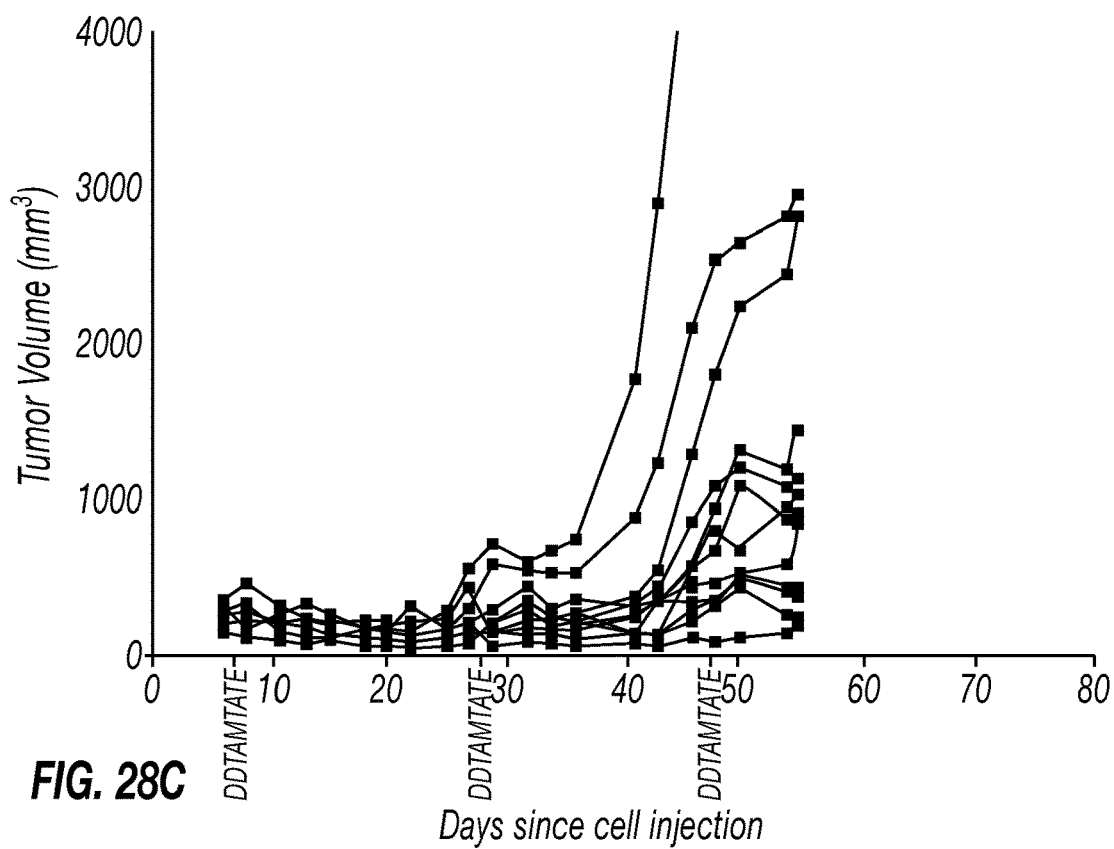
Figure 29:
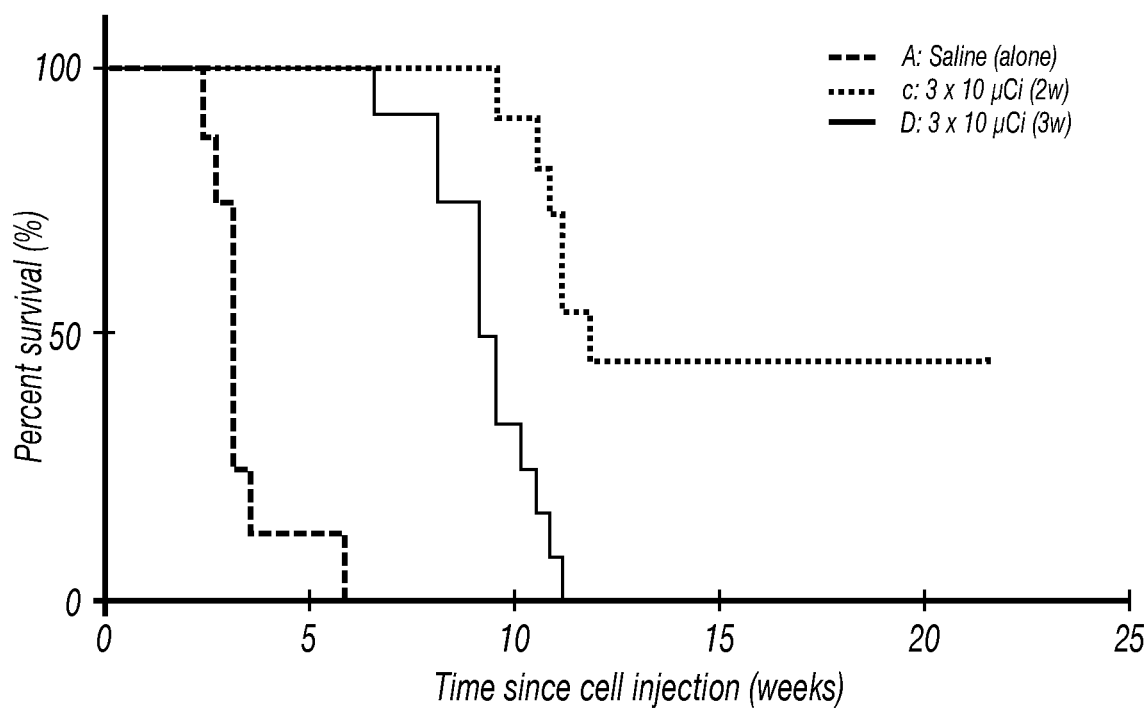
FIG. 29 is a graph of Kaplan Meier survival curves of mice treated with $^{212}$Pb-DOTAMTATE.

Results and Conclusions:

Referring to FIGS. 28 A-C and 29, animals that are injected with saline had a median survival of 2.3 weeks post saline injection. Mice that receive three injections of $^{212}$Pb-DOTAMTATE have a median survival of 9.1 weeks post cell injections with all animals lost by 11.1 weeks. The animals that receive three injections of $^{212}$Pb-DOTAMTATE at 2-week intervals show a median survival of 11.9 weeks with 45% of animals alive at 21 weeks post cell injections. This data shows that the timing of the drug treatment is critical on the effect of tumor volume. Tumor volumes can be controlled but if there is too long of a duration between cycles, the treatment is less effective.

Animal Blood Pharmacokinetics of IV Injected $^{212}$Pb-DOTAMTATE in CD-1 Mice

Methods:

CD-1 mice are injected with 10 μCi of $^{212}$Pb-DOTAMTATE as part of a biodistribution study. Blood is collected at 15 minutes; 1 hour and 4 hours post injection. Body weights determined by taking the average of 10 CD-1 mice at 7 weeks old, the age of the mice in this study and using this weight, blood volume is estimated using the equation by Lee and Blaufox (1985). % ID in blood mice is then calculated for 5 mice per group.

Figure 30:
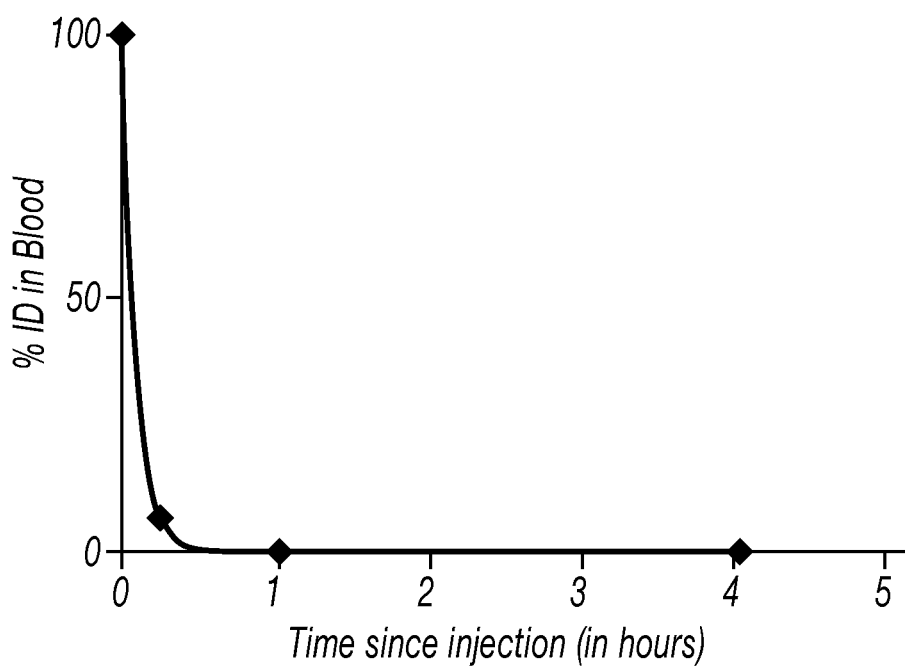
FIG. 30 is a graph of $^{212}$Pb-DOTAMTATE clearance in blood. % ID of $^{212}$Pb-DOTAMTATE in blood of CD-1 mice at 15 minutes, 1 hour and 4 hours post injection.

Results and Conclusions:

Referring to FIG. 30 and Table 1, the average % ID in blood is 6.7% 15 minutes post injection of $^{212}$Pb-DOTAMTATE suggesting a rapid clearance. One-hour post-injection, the % ID of blood decreases further to 1.8%. At 4 hours-post injection the level of drug in the blood is almost non-detectable at 0.1% ID. The data are shown in the table below and graphed over time.

TABLE 1

| Average % ID of $^{212}$Pb-DOTAMTATE in blood of CD-1 mice | | | |
|---|---|---|---|
| Hours | Average | SD | n |
| .25 | 6.7 | 1.3 | 5 |
| 1 | 1.8 | 0.4 | 5 |
| 4 | 0.1 | 0.1 | 5 |

Biodistribution of $^{212}$Pb-DOTAMTATE in Female Non-Tumor Bearing Mice

Distribution of the $^{212}$Pb-DOTAMTATE is assessed in a biodistribution study with CD-1 non-tumor bearing mice at multiple timepoints between 15 minutes and 48 hours.

Methods:

Female CD-1 mice (~20 g) are injected with a single dose of $^{212}$Pb-DOTAMTATE. Specifically, 10 μCi of $^{212}$Pb-DOTAMTATE is diluted in PBS and 100 μl is administered to the mice via intravenous injection. The animals are sacrificed at predetermined time points of 15 minutes, 1 hour, 4 hours and 24 hours and 48 hours post drug injection. Tissues are collected from each animal and evaluated for amount of radioactive material in each organ by auto gamma counter. Specifically, organs are harvested, weighed and transferred to polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Figure 31:
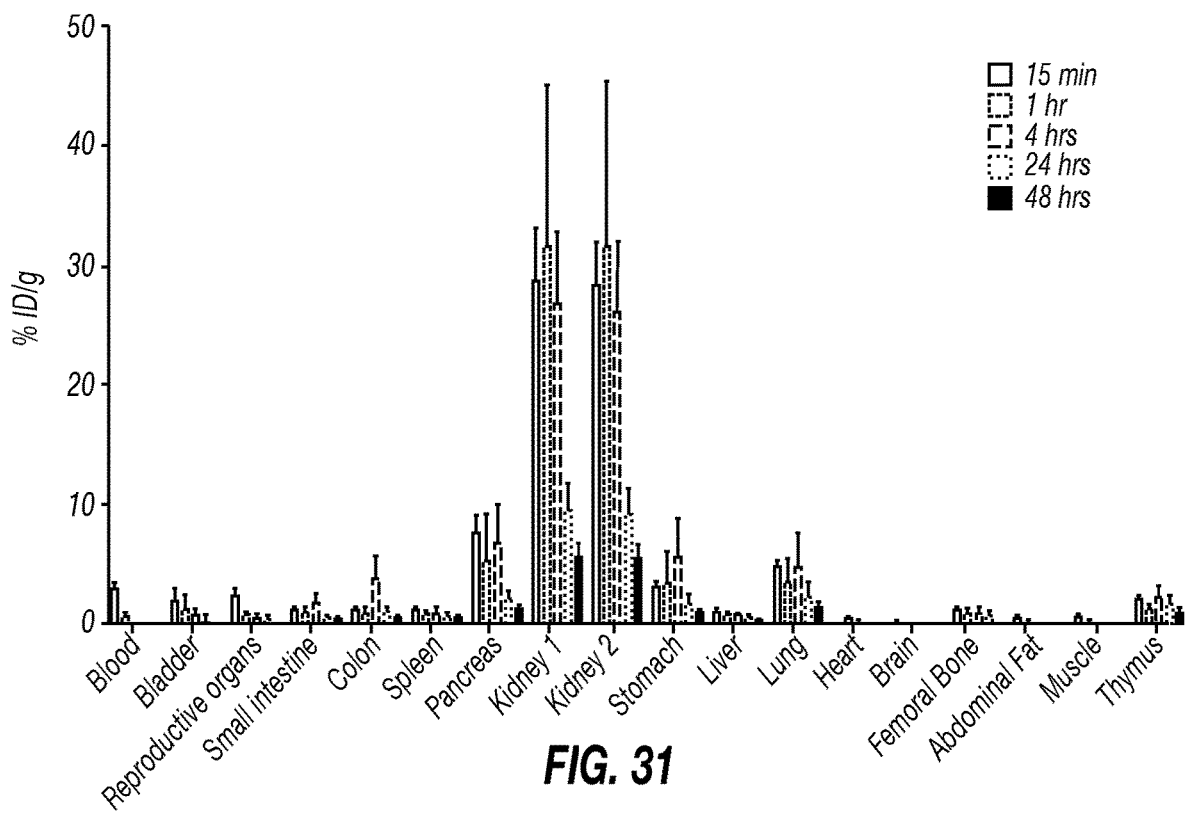
FIG. 31 is a graph of $^{212}$Pb-DOTAMTATE biodistribution in CD-1 Mice. Biodistribution of $^{212}$Pb-DOTAMTATE in CD-1 mice. % ID/g for the average of three studies is shown in numerous organs at 15 minutes, n=5; 1 hour, n=8; 4 hours, n=7; 24 hours, n=8; and 48 hours, n=5 post injection.

Results and Conclusions:

Referring to FIG. 31, all organs have a percent-injected dose per gram of less than 10% for each of the stated time points, with the exception of the kidneys. The greatest accumulation of $^{212}$Pb-DOTAMTATE occur in the kidneys with the highest level observed at 1-hour post injection (~30% injected dose per gram). This decreases significantly to near 10% injected dose per gram by 24 hrs and continues to decrease at 48 hours post injection. As the kidneys are the primary method of clearance for the drug, this is not an unexpected observation and is not a cause for concern based on other data, primarily toxicological and efficacy data that we have obtained.

Biodistribution of $^{203}$Pb-DOTAMTATE and $^{212}$Pb-DOTAMTATE in CD-1 Non-Tumor Bearing Mice Methods:

Female CD-1 mice (~20 g) are injected with a single dose of $^{203}$Pb-DOTAMTATE or $^{212}$Pb-DOTAMTATE. Specifically, 10 μCi of $^{203}$Pb-DOTAMTATE or $^{212}$Pb-DOTAMTATE is diluted in saline and 100 μl is administered to the mice via intravenous injection. The animals are sacrificed at predetermined time points of 4 hr and 24 hours post drug injection. Tissues are collected from each animal and evaluated for amount of radioactive material in each organ by auto gamma counter. Specifically, organs are harvested, weighed and transferred to 12×55 mm polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected, wherein "% ID" means percent injection dosage.

Figure 32:
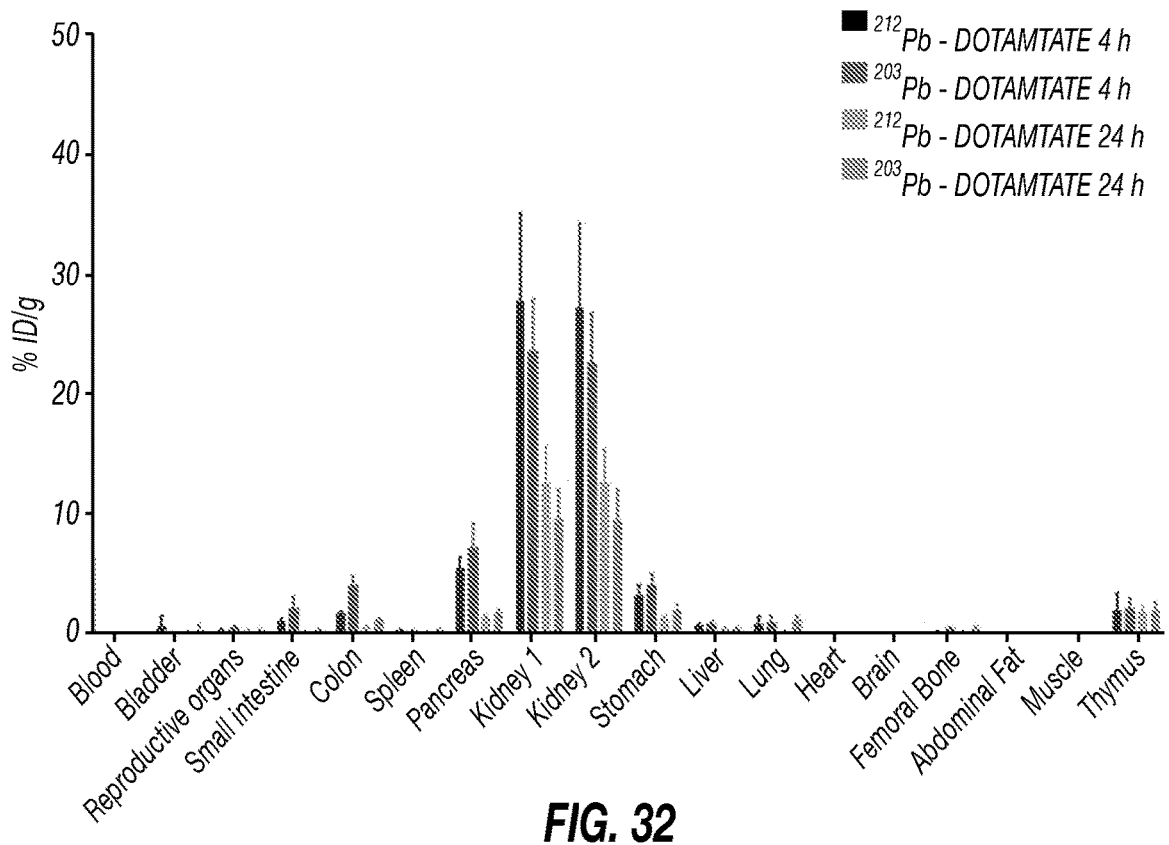
FIG. 32 is a graph of biodistribution of $^{212}$Pb-DOTAMTATE and $^{203}$Pb-DOTAMTATE in CD-1 Mice. $^{212}$Pb-DOTAMTATE and $^{203}$Pb-DOTAMTATE biodistribution in CD-1 mice at 4 hours and 24 hours after drug injection. Values are shown as % ID/g.

Results and Conclusion:

Referring to FIG. 32, organ uptake in CD-1 mice treated with $^{203}$Pb-DOTAMTATE is not significantly different from organ uptake in mice treated with $^{212}$Pb-DOTAMTATE in all critical organs. This further confirms, in a direct side by side comparison, that the two isotopes have a similar pharmacokinetic profile.

Based on these data and others, an exploratory eIND (Exploratory Investigational New Drug) is conducted to assess the dosimetry and biodistribution of $^{203}$Pb-DOTAMTATE in patients with somatostatin expressing neuroendocrine cancers as a surrogate for $^{212}$Pb-DOTAMTATE. The distribution and excretion characteristics of $^{203}$Pb-DOTAMTATE is very similar to PK (pharmacokinetics) properties of commercially available octreotate drugs with the kidneys being the dose limiting organ.

$^{212}$Pb-DOTAMTATE Cumulative Excretion

Methods:

Female, CD-1 mice are injected intravenously with 10 μCi of $^{212}$Pb-DOTAMTATE. Animals are then placed into individual metabolic cages to facilitate excretion collection. At predetermined intervals of 1 hour, 2 hours, 3 hours, 4 hours, 5 hours, 6 hours and 24 hours' post injection animals are removed from metabolic cage and placed in to a new metabolic cage. Cage funnels are then rinsed with PBS and 1 ml from each mouse is counted in an auto gamma counter. Feces are collected and analyzed in a separate auto gamma counter tube.

Figure 33:
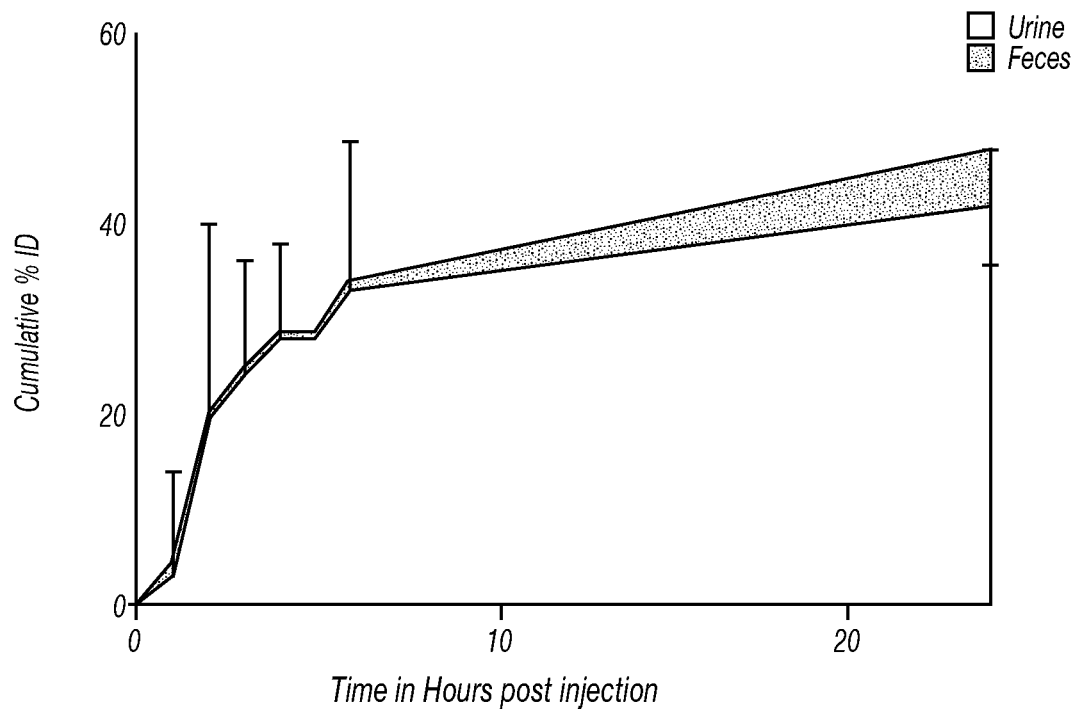
FIG. 33 is a graph of $^{212}$Pb-DOTAMTATE cumulative excretion in mice. Cumulative excretion of $^{212}$Pb-DOTAMTATE in urine and feces over time. % ID of drug is shown at 1 hr, 2 hr, 3 hr, 4 hr 5 hr, 6 hr and 24 hours post drug injection in the urine and feces.

Results and Conclusions:

Referring to FIG. 33, the results of the $^{212}$Pb-DOTAMTATE study show that the drug is metabolized by the kidneys and passed into the urine and feces. The level of drug found in the excretion at 24 hrs is in line with what would be expected given the biodistribution data at 24 hrs also conducted in CD-1 mice.

Biodistribution of $^{212}$Pb-DOTAMTATE with Kidney Protection Agents

It is not anticipated that $^{212}$Pb-DOTAMTATE will interact with major molecular pharmacokinetic determinants such as enzymes, drug transporters, or orphan nuclear receptors. However, renal toxicity has been a reported concern with high dose radionuclide therapy. Co-infusion of the drug with positively charged amino acids is shown to reduce kidney dose of radiolabeled octreotide by 25% (Hammond et al., 1993). As a result, a kidney protection study is conducted with $^{212}$Pb-DOTAMTATE and various agents to determine if the exposure to the kidneys could be minimized during treatment.

Methods:

Female CD-1 mice (~20 g) are injected with a single dose of $^{212}$Pb-DOTAMTATE. Specifically, 5 μCi of $^{212}$Pb-DOTAMTATE is diluted in PBS (control), 2.5% Lysine-Arginine mixture, Aminomedix (600 mg/kg Lys-Arg, 15 mg/kg amifostine is diluted in half in PBS) or 4.2% Clinisol and is administered to the mice via intravenous injection. The animals are sacrificed at predetermined timepoints of 1 hour and 4 hours post injection. Tissues are collected from each animal and evaluated for amount of radioactive material in each organ by auto gamma counter. Specifically, organs are harvested, weighed and transferred to polypropylene tubes. The tubes are placed in a calibrated Wizard2 γ-counter (PerkinElmer, Shelton, Conn.) and counted for three minutes (204-274 keV). A standard consisting of one-twentieth of the injection volume is counted with each time point. The background is automatically subtracted from the counts. The standard is also used for decay correction. % ID/g is calculated for each organ collected.

Figure 34A:
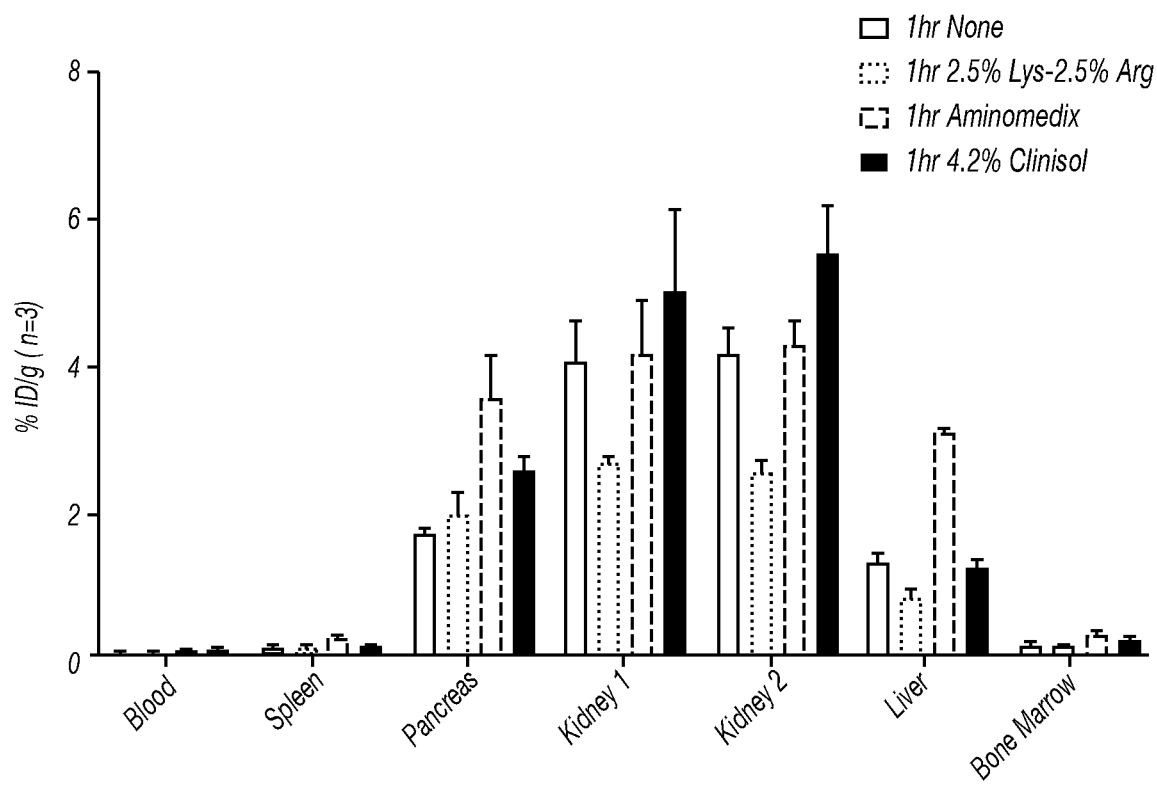
FIGS. 34A and 34B are graphs of $^{212}$Pb-DOTAMTATE biodistribution with kidney protection agents. Kidney protection agents are coinjected with $^{212}$Pb-DOTAMTATE in CD-1 mice. % ID/g of $^{212}$Pb-DOTAMTATE with No kidney protection agent, 2.5% lys-arg mixture, aminomedix or clinisol are shown at 1 hr (34A) and 4 hr (34B) post injection in various organs.
Figure 34B:
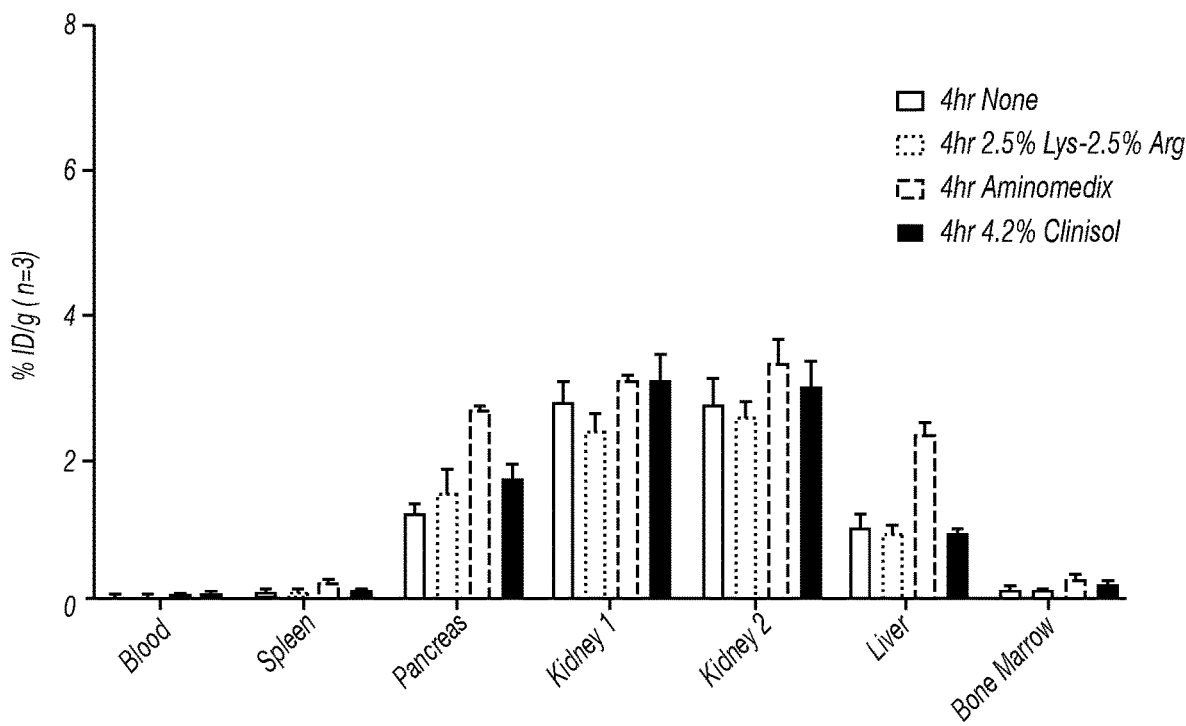

Results and Conclusions:

Referring to FIGS. 34A and 34B, the kidney protection agent consisting of 2.5% lysine-arginine is the most effective at reducing kidney uptake of $^{212}$Pb-DOTAMTATE especially after 1-hour post injection. Reduced drug uptake in the liver is also observed in the animals who received 2.5% Lys-Arg. The other agents show no significant difference compared to the non-kidney protection agent control. This suggests that a combination of positively charged amino acids, 2.5% Lys-Arg, is the most effective method for reducing kidney uptake with $^{212}$Pb-DOTAMTATE.

Non-GLP Dose Range Finding Study in Athymic Nude Mice

Methods:

Female athymic nude mice (~20 g) are injected with a single dose of 10 μCi, 20 μCi, 40 μCi or 60 μCi of $^{212}$Pb-DOTAMTATE or control PBS intravenously. Five animals are assigned per treatment group. Animals are weighed three times per week and monitored daily for signs of termination criteria (15% weight loss over 2 days, lack of grooming over 5 days, lethargy/weakness over 3 days, reduced motility, hunched back, diarrhea, hypothermia). The study is concluded after 4 weeks.

Figure 35:
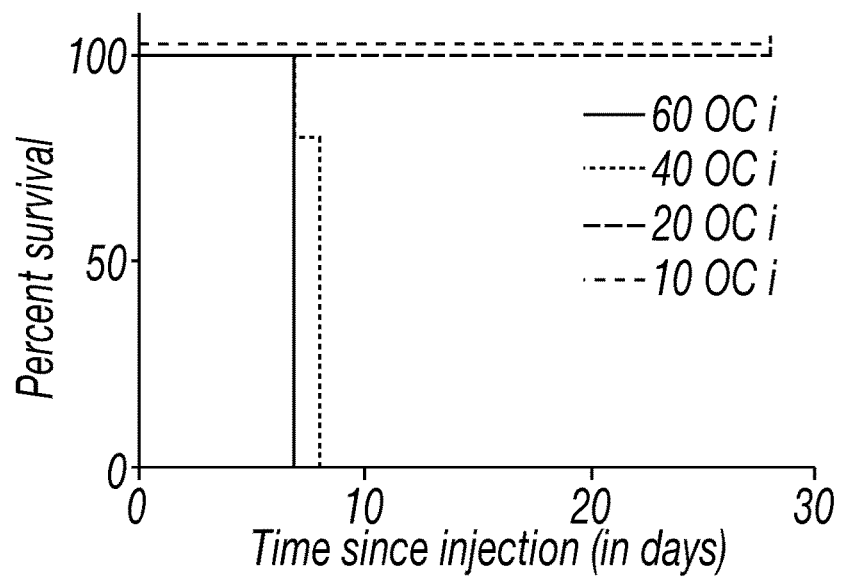
FIG. 35 is a graph of Kaplan-Meier survival curve—acute toxicity of $^{212}$Pb-DOTAMTATE treated mice. Kaplan-Meier survival curve of $^{212}$Pb-DOTAMTATE treated mice. Animals received a single dose of 10 µCi, 20 µCi, 40 µCi, or 60 µCi of 212Pb-DOTAMTATE. Survival of the animals are shown in days post injection during the 4-week study.
Figure 36:
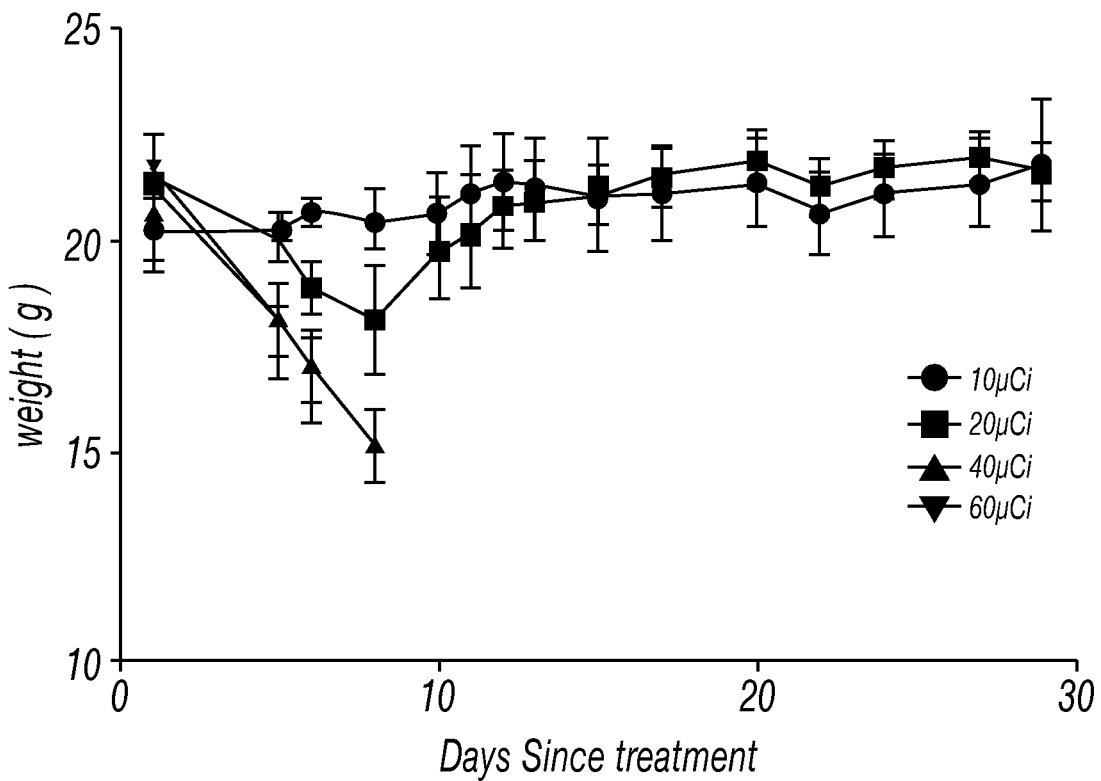
FIG. 36 is a graph of body weights of single dose acute toxicity study mice treated with $^{212}$Pb-DOTAMTATE. Body weight of mice treated with a single dose of 10 µCi, 20 µCi, 40 µCi or 60 µCi of 212Pb-DOTAMTATE shown in grams. Mice were weighed three times per week over the month-long study.

Results and Conclusions:

Referring to FIGS. 35 and 36, acute toxicity is observed at the higher activity doses of $^{212}$Pb-DOTAMTATE. All animals in the 60 μCi $^{212}$Pb-DOTAMTATE die 7 days post injection and lose significant weight. All of the animals in the 40 μCi treatment group die by 8 days post injection and also lost weight each day until death. 100% of the animals in the control, 10 μCi and 20 μCi $^{212}$Pb-DOTAMTATE treatment groups survive and gain weight until the end of the four-week study suggesting that the maximum tolerated dose is between 20 μCi and 40 μCi. Based on these data, a GLP toxicity study is initiated at doses up to 40 μCi.

Intravenous Injection (IV) and Intraperitoneal Injection (IP) Toxicity Study of Free $^{212}$Pb in Mice The purpose of this study is to evaluate and assess the in vivo acute and chronic toxicity of free $^{212}$Pb when administered via intravenous injection or intraperitoneal injection to Balb/c mice. Animals are sacrificed on Day 7 (acute) and Day 90 (chronic) to assess the acute and delayed occurrence of test article-induced effects, including the impact of the radionuclide given under a "worst-case" scenario of total radiolabeling chelation sequestration failure. Both intravenous injection and intraperitoneal injection administration routes are studied despite the fact that the former is not a planned use of the radionuclide, to exaggerate any potential toxicity and to identify target organs.

Results:

Administration of the test article by single IV or IP injection at dose levels of above or equal to 2.5 μCi is associated with acute (by Day 7) marked decreases in hematology parameters indicative of bone marrow toxicity. Furthermore, there is renal damage indicative of radiation-induced nephrotoxicity and possibly some hepatic injury at the highest doses. The findings in this study indicate that 2.5 µCi is the NOAEL for free $^{212}$Pb in mice for both the IV and IP routes of administration, with mortality occurring at IV doses of 20 µCi and at IP doses of 15 µCi.

There is no mortality at 2.5, 5, 7.5, and 10 µCi by either IV or IP route. However, mortality occurs at 15 µCi IP on Days 11, 40, and 90 (three often animals), and at 20 µCi IV on Day 16 (two of five animals). Mortality also occurs at 10 µCi on Day 69 (one of five animals), at µCi on Days 8, 11, and an unrecorded date (three of four animals), and at 50 µCi on Day 9 (three of five animals) for the IP route. Body weight loss is observed at Day 7 following IV administration at doses of 20 and 30 µCi; the change is significant when comparing IV dosing at 2.5 vs. 30 µCi (P<0.01) or at 7.5 vs. 30 µCi (P<0.05). While no further loss had occurred by Day 90, the significance of weight loss at 30 µCi persisted at the later time point (P<0.01 vs. untreated control). At both time points, body weights correlates inversely with IV dose level. While some weight loss is also observed at Day 7 following IP administration at 10 µCi and higher, the effects are not significant. Recovery in body weight is seen by Day 90, although attenuation of weight gain becomes significant at 15 µCi, IP (P<0.05 vs. untreated control).

Dose-related decreases in hematology parameters occurred in both IV and IP groups. At Day 7, there is a dose-related decrease in the mean values for White Blood Cells and platelet numbers following both IV and IP administration starting at the lowest dose level (2.5 µCi). There is partial recovery at 90 days in all groups. In general, clinical chemistry levels remained within normal ranges, with the exception of the liver parameters ALT (Alanine Amino Transferase) and AST (Aspartate Amino Transferase), which appears to be somewhat increased at 90 days in the high-dose group. Renal parameters are within normal limits.

Target organs for this study are bone marrow, kidneys, and liver. The histopathologic findings in this study indicate that both IV and IP administration of the test article at 5 µCi or above is associated with expected decreases in the erythroid, myeloid, and megakaryocytic series in the bone marrow and is associated with corresponding changes in the hematology parameters. There is also nephritic change at both 7 and 90 days, consistent with radiation-induced nephropathy (Cohen & Robbins, 2003), which, over time, may lead to irreversible renal failure and anemia due to erythropoietin insufficiency. The kidney, while having a substantial capacity for repair, is a radiosensitive organ, and irreversible nephrotoxicity may occur with radiation treatment. Hepatic changes, considered to be possibly treatment-related, are evident at both 7 and 90 days and are associated with increases in ALT and AST at 90 days, 50 µCi IP.

Conclusion:

Administration of $^{212}$Pb by single IV or IP injection at dose levels of above or equal to 2.5 µCi is associated with marked decreases in hematology parameters indicative of bone marrow toxicity. Furthermore, there is renal damage indicative of radiation-induced nephrotoxicity and possibly some hepatic injury at the highest doses. The findings in this study indicate that 2.5 µCi is the NOAEL for both the IV and IP routes of administration, with mortality occurring starting at IV doses of 20 µCi and at IP doses of 15, 30, 40, and 50 µCi.

There is no mortality at 2.5, 5, 7.5, and 10 µCi by either IV or IP route. However, mortality occurs at 15 µCi IP on Days 11, 40, and 90 (three often animals), and at 20 µCi IV on Day 16 (two of five animals). Mortality also occurs at 30 µCi on Day 69 (one of five animals), at µCi on Days 8, 11, and an unrecorded date (three of four animals), and at 50 µCi on Day 9 (three of five animals) for the IP route. Among the mice utilized for the hematology blood draws, all mice in the IV-injected groups survive the 90-day study period. In the IP-injected groups, mortality occurs at 30 µCi on Day 69 (one of five animals), at 40 µCi on Days 10 and 16 (two of five animals) and at 50 µCi on days 7, 10, and 16 (three, one, and one of five animals, respectively). Body weight loss is observed at Day 7 following IV administration at doses of 20 and 30 µCi; the change is significant when comparing IV dosing at 2.5 vs. 30 µCi (P<0.01) or at 7.5 vs. 30 µCi (P<0.05). While no further loss had occurred by Day 90, the significance of weight loss at 30 µCi persists at the later time point (P<0.01 vs. untreated control). At both time points, body weights correlates inversely with IV dose level. While some weight loss is also observed at Day 7 following IP administration at 10 µCi and higher, these effects are not significant. Recovery in body weight is seen by Day 90, although attenuation of weight gain became significant at 15 µCi, IP (P<0.05 vs. untreated control).

Marked dose-related decreases in hematology parameters occurred in both IV and IP groups. At Day 7, a dose-related decrease in the mean values for WBCs and platelet numbers is observed following either IV or IP administration, even at the lowest dose level (2.5 µCi). There is partial recovery at 90 days in all groups, although high variability in values is seen within groups (among animals). In general, clinical chemistry levels remain within normal ranges, with the exception of the liver parameters, ALT and AST, which appear to be increased at 90 days in the high-dose group. Renal parameters are within normal limits. Target organs for this study are bone marrow, kidneys, and possibly liver. Histopathologic findings in this study indicate that both IV and IP administration of the $^{212}$Pb at 5 µCi or above is associated with expected decreases in the erythroid, myeloid, and megakaryocytic series in the bone marrow and is associated with corresponding changes in the hematology parameters. There is also nephritic change at both 7 and 90 days consistent with radiation-induced nephropathy (Cohen & Robbins, 2003), which, over time, may lead to irreversible renal failure and anemia due to erythropoietin insufficiency. The kidney, while having a substantial capacity for repair, is a radiosensitive organ, and irreversible nephrotoxicity may occur with radiation treatment. Hepatic changes, considered to be possibly treatment-related, are evident at both 7 and 90 days and are associated with increases in ALT and AST at 90 days 50 µCi IP. Particularly careful examination is conducted on the bladder, lungs, intestines, and lymphoid system, and no treatment-related findings are detected in these other organs. There are no changes considered to be due to (elemental) lead toxicity.

Repeat-Dose Toxicity

Methods:

Female, tumor free CD-1 mice are injected with one dose of 40 µCi $^{212}$Pb-DOTAMTATE, 2 doses of 20 µCi $^{212}$Pb-DOTAMTATE or three doses of 15 µCi $^{212}$Pb-DOTAMTATE. Animals are given three weeks between doses for these who received multiple treatments. Animals are weighed three times per week and monitored daily for signs of termination criteria (15% weight loss over 2 days or 20% loss from initial weight, lack of grooming over 5 days, lethargy/weakness over 3 days, reduced motility, hunched back, diarrhea, hypothermia). Blood for hematological analysis is collected weekly.

Results and Conclusion:

Signs of acute toxicity are examined in a non-GLP repeat dose study to compare single administration vs fractionation (described below). This study is designed based on observations made in athymic nude mice. While a 40 µCi dose in an athymic nude mouse is severely toxic resulting in 100% of the animal reaching termination criteria in 8 days, and 40 µCi administered as two separate 20 µCi injections three weeks apart result in the same toxicity profile, however three 15 µCi injections three weeks apart do not show significant or irreversible signs of toxicity. This observation is correlated with the GLP findings that hematological toxicity in the surviving animals from the higher dose groups is recoverable within a month. As renal and hepatic toxicity is cumulative a single dose treatment vs multiple doses leading to the same cumulative dose should be similar (Barendsen, 1964). Fractionated administration of radioactivity three weeks apart compared to a single injection had very similar toxicity profile. Based on these results, a new study is done to compare these 3 dosing regimens in tumor free CD-1 mice.

Figure 37:
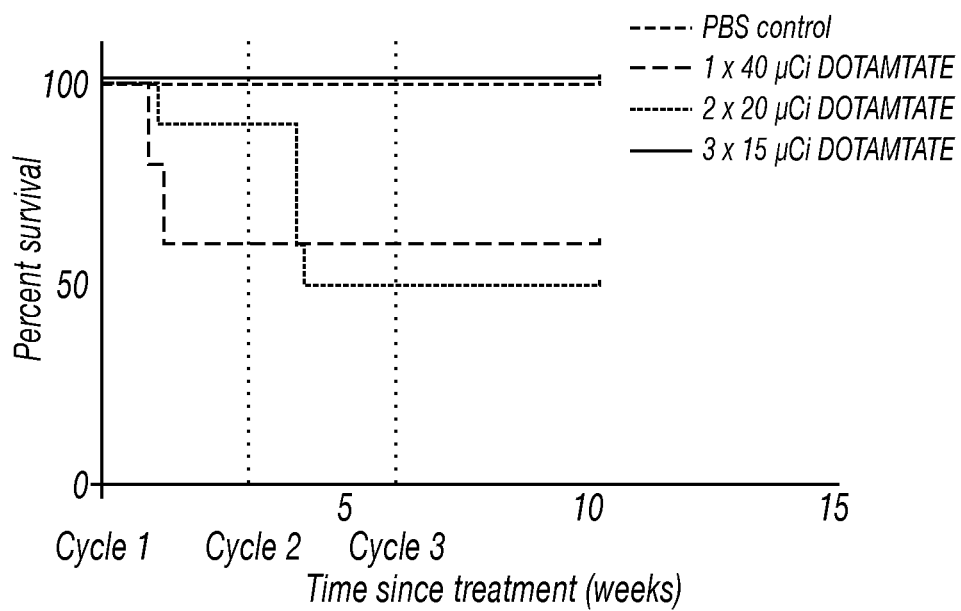
FIG. 37 is a graph of fractionated dose vs. single dose $^{212}$Pb-DOTAMTATE Toxicity Study in Tumor-Free CD-1 Mice. Kaplan-Meier curve of PBS alone, n=10; 1×40 µCi, n=10; 2×20 µCi, n=10; and 3×15 µCi, n=10 treatment groups. Drug cycles 1, 2 and 3 are shown with grey dots.
Figure 38:
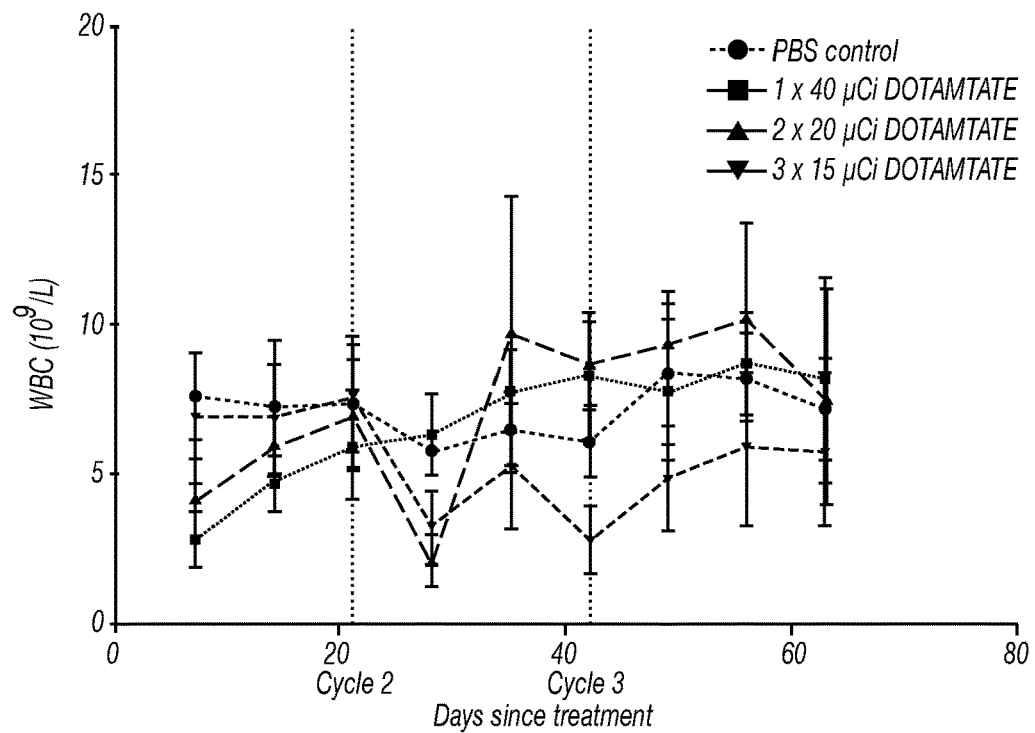
FIG. 38 is a graph of white blood cell counts—single vs fractionated $^{212}$Pb-DOTAMTATE. White blood cell counts are shown for animals treated with PBS alone, 1×40 µCi, 2×20 µCi, and 3×15 µCi $^{212}$Pb-DOTAMTATE. Drug cycles 1, 2 and 3 are shown with grey dots.
Figure 39:
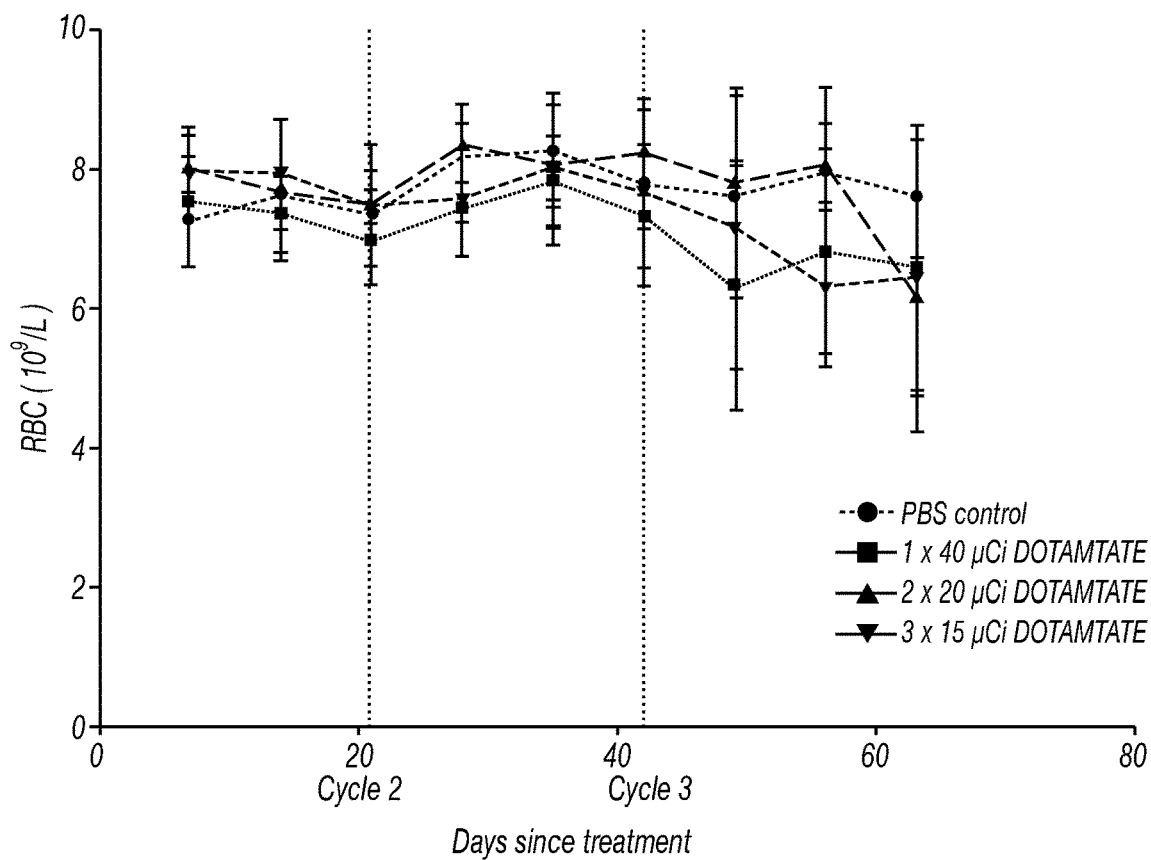
FIG. 39 is a graph of red blood cell counts—single vs. fractionated doses of $^{212}$Pb-DOTAMTATE. Red blood cell counts are shown for animals treated with PBS alone, 1×40 µCi, 2×20 µCi, and 3×15 µCi $^{212}$Pb-DOTAMTATE. Drug cycles 1, 2 and 3 are shown with grey dots.

The fractionated dose vs single dose of $^{212}$Pb-DOTAMTATE toxicity study is performed in tumor-free CD-1 mice (FIG. 37). Animals are given a single dose of drug or two or three cycles of the drug every three weeks. Almost 40% of animals in the 1×40 µCi group died nine days after injection but those that survived are able to survive through the remainder of the study. 50% of the animals in the 2×20 µCi group died within four weeks of the study and one week after receiving the second dose. The animals that survive the first two injections are able to survive through the end of the study. The animal group that receive 3×15 µCi of $^{212}$Pb-DOTAMTATE have no mortality. All of the treated animals do not gain weight at the same rate as the untreated controls and appear to maintain a similar weight throughout the stud except after each treatment where body weight decreases and then recovers. Hematological toxicity appears to be the reason for death in the first two groups. Those animals that can recover from the initial toxicity are able to survive. This is evident by the low white blood cell counts in the 1×40 µCi and 2×20 µCi groups after drug injections (FIG. 38). Animals who receive 3×15 µCi doses of $^{212}$Pb-DOTAMTATE also had a decrease in their WBC counts but are able to recover after each dose. This study suggests that a fractioned dose of drug is optimal as it allows the same cumulative dose but with recoverable hematological effects.

Biodistribution Study of $^{212}$Pb-DOTATOC in CD-1 Mice
Method:

$^{212}$Pb-DOTATOC is prepared based on activity needed at time of injection. 4.1 ng of peptide per 10 µCi of $^{212}$Pb into a tube is added. The mixture is incubated for 10 minutes at 50° C. with shaking. ITLC (Instant thin layer chromatography) is used to verify that chelation is >95%. 100 µl of $^{212}$Pb-DOTATOC is intravenously injected into the tail of each mouse. An auto gamma counter is used to determine the counts of each organ and control tube.

Figure 40:
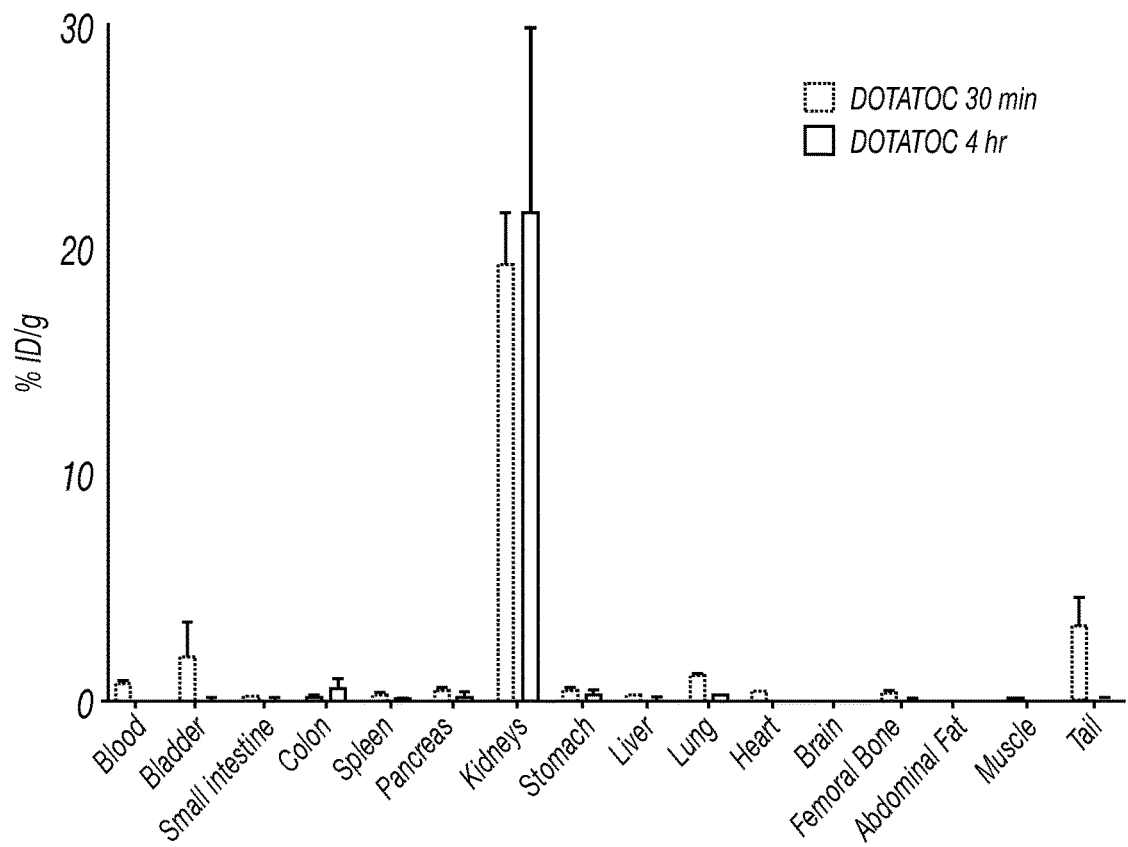
FIG. 40 is a graph of $^{212}$Pb-DOTATOC biodistribution in female CD-1 mice. Biodistribution of $^{212}$Pb-DOTATOC in CD-1 mice. 10 µCi of drug was administered and organs were collected from 3 mice per timepoint: 30-minute and 4 hours post injection.
Figure 41:
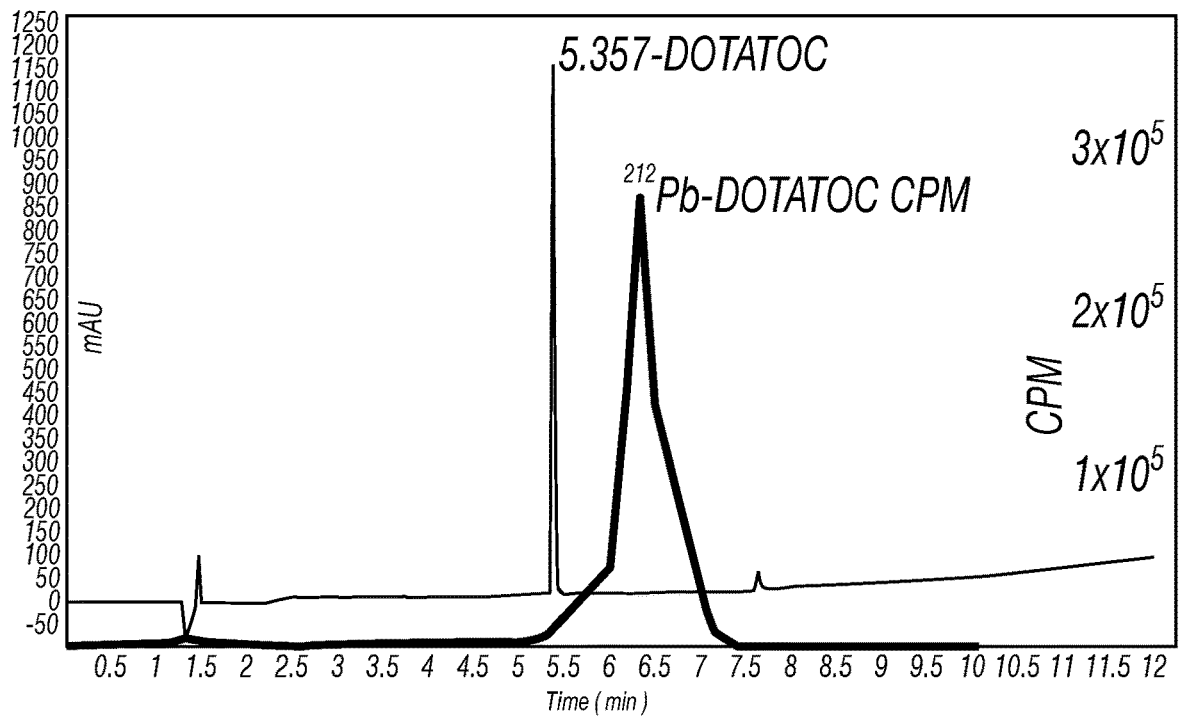
FIG. 41 is a graph of radiometric plot of $^{212}$Pb-DOTATOC overlaid with DOTATOC system suitability chromatogram. HPLC chromatogram showing retention time of DOTATOC alone at 5.357 min and an overlay of $^{212}$Pb DOTATOC fractions plotted showing peak activity (in CPM) at 6.5 minutes.
Figure 42A:
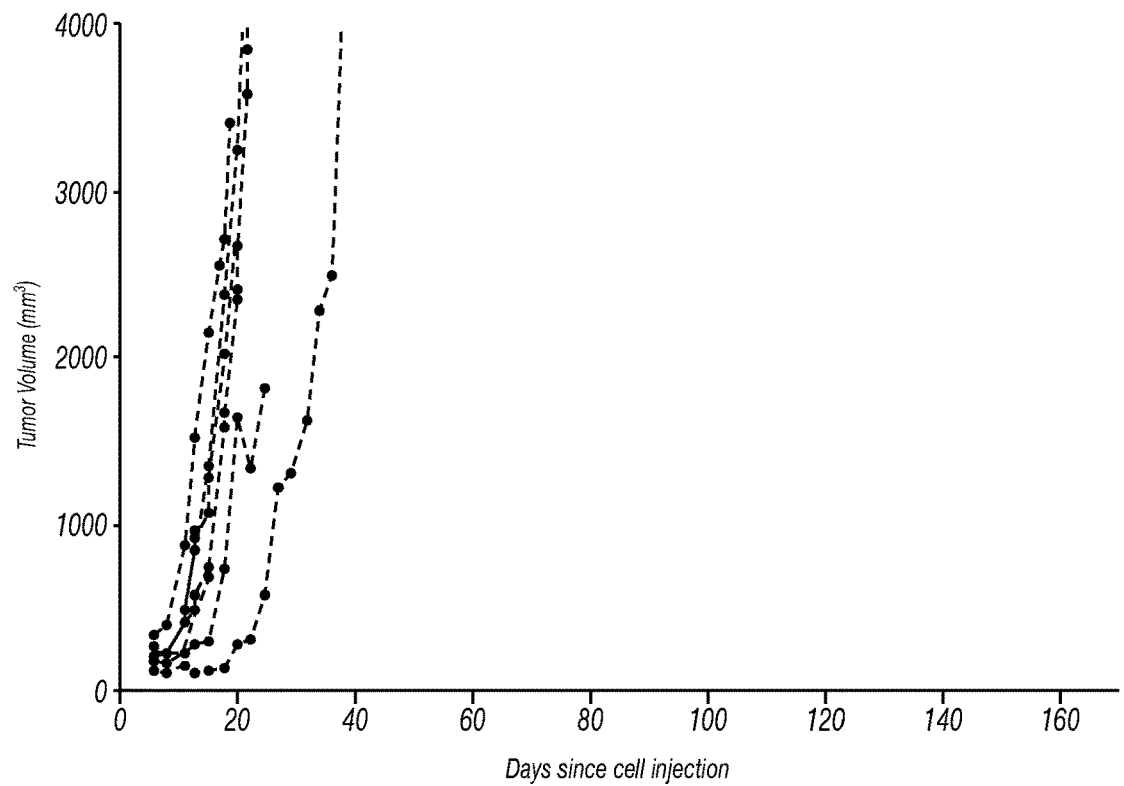
FIGS. 42A-42F contains graphs of individual efficacy of mice treated with $^{212}$Pb-DOTAMTATE and ADRUCIL® at two week and three week intervals.
Figure 42B:
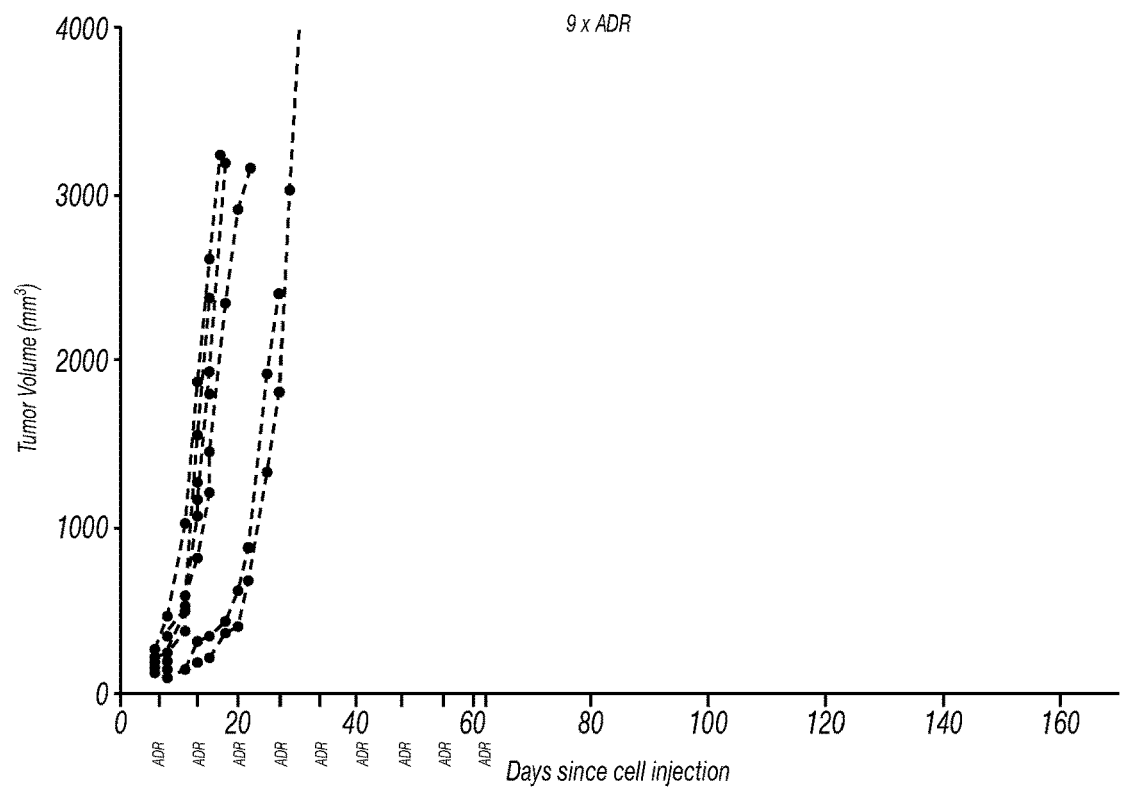
Figure 42C:
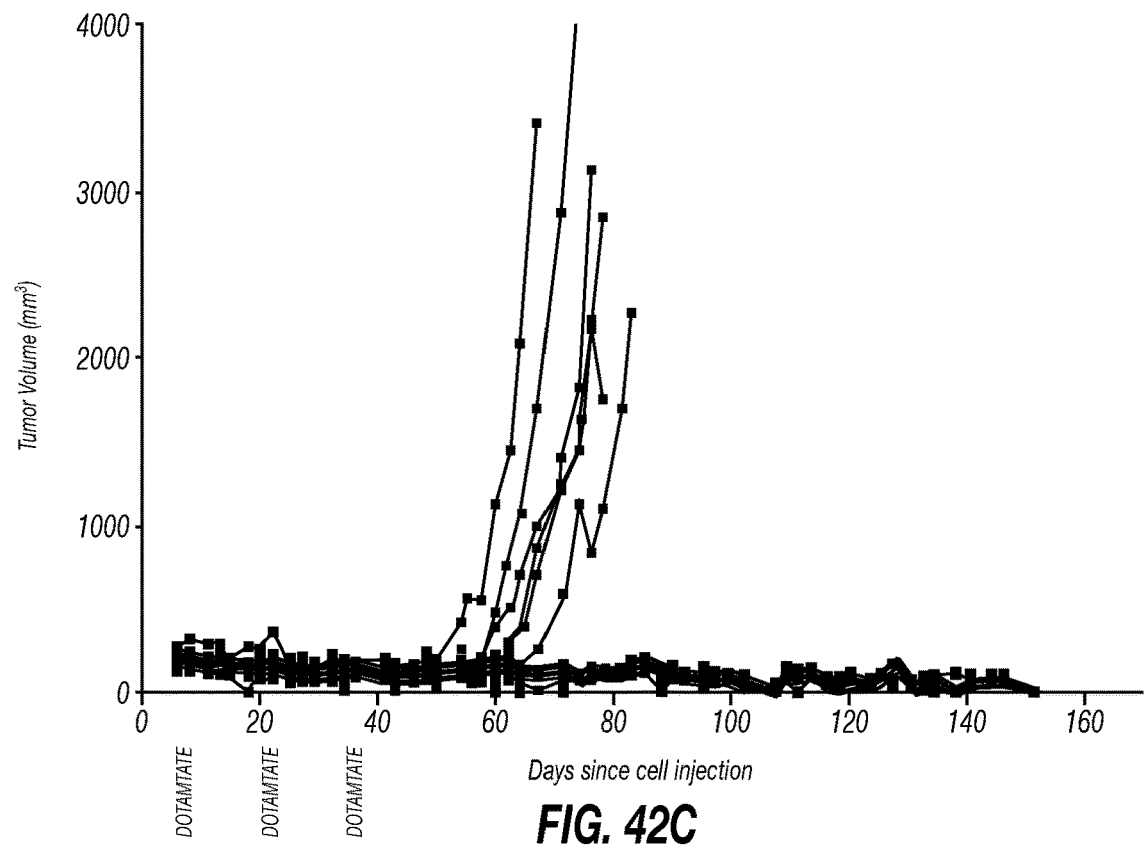
Figure 42D:
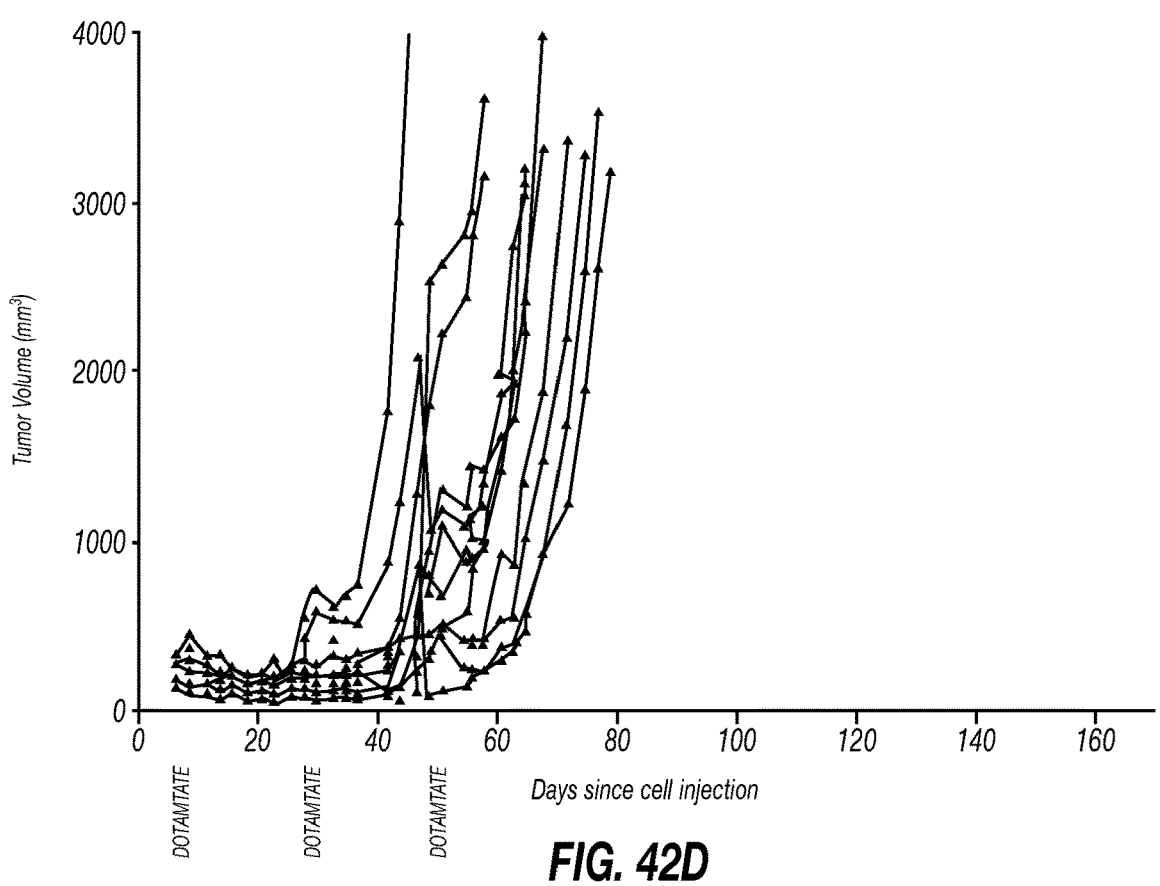
Figure 42E:
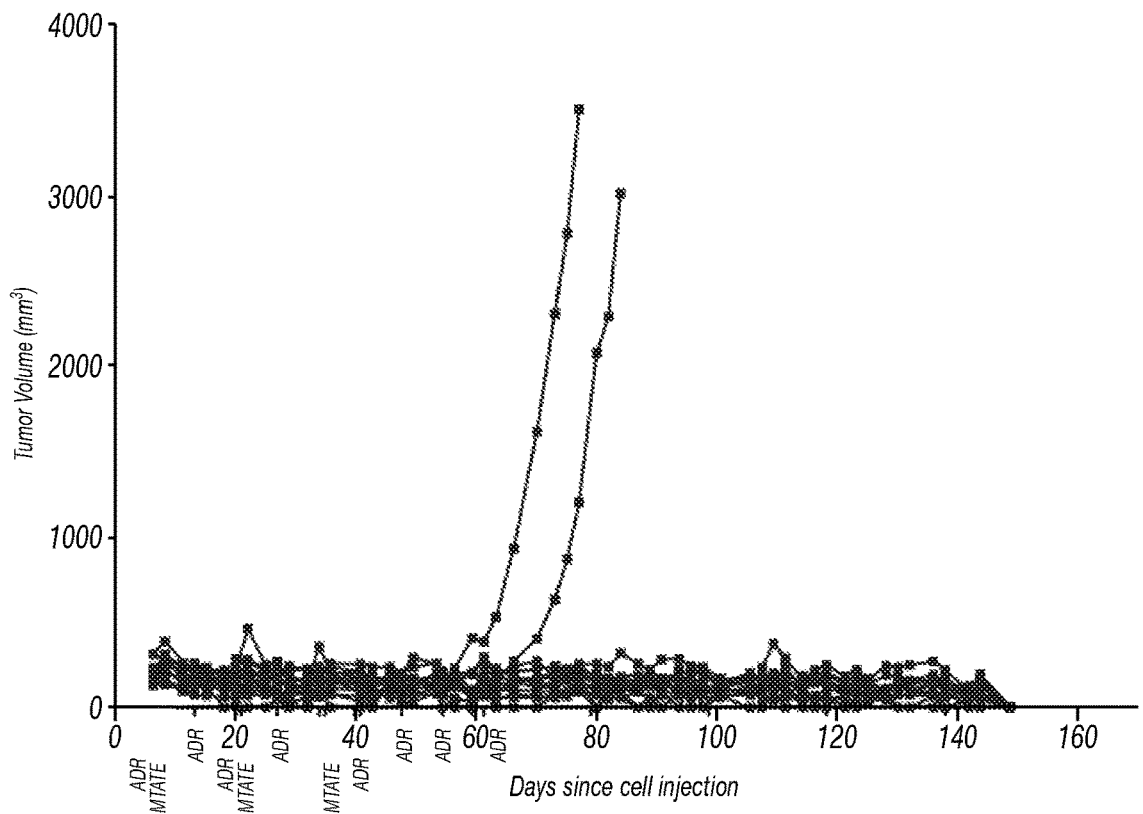
Figure 42F:
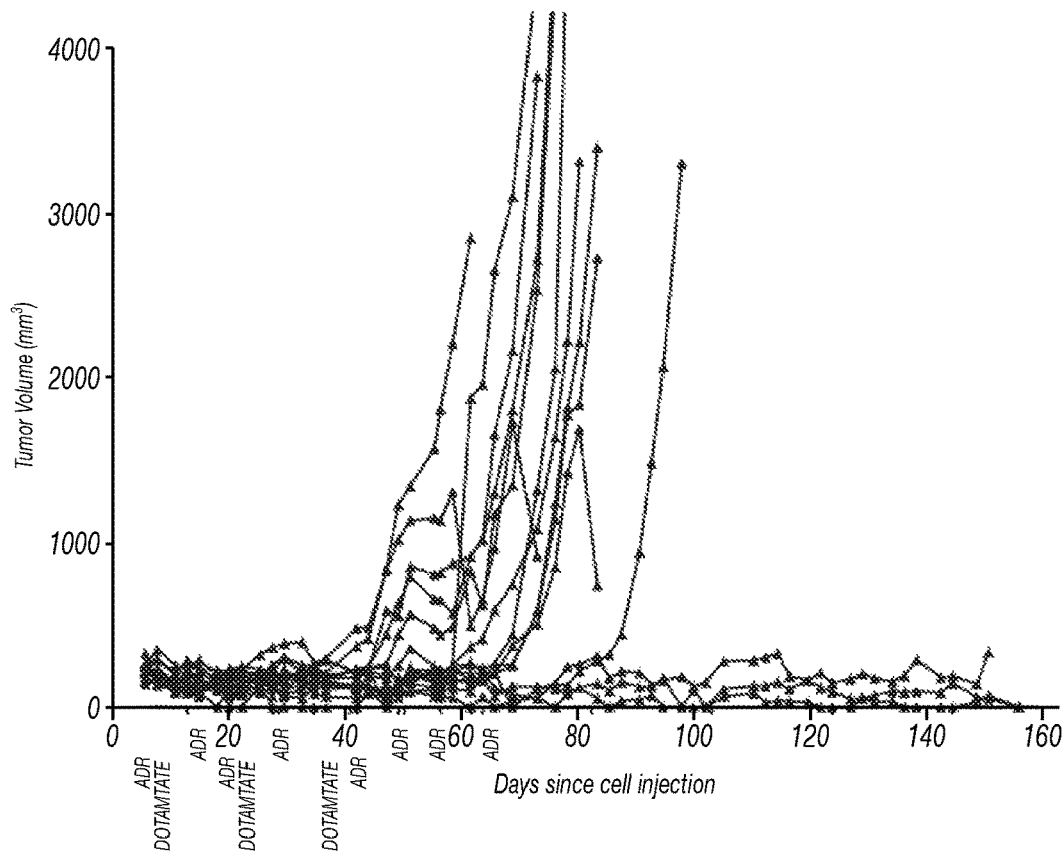

Results:

A biodistribution is conducted with 10 µCi of $^{212}$Pb-DOTATOC at 30 minutes and 4 hours in female, CD-1 non-tumor bearing mice. The data (FIG. 40) shows rapid drug clearance with the highest accumulation observed in the kidneys with 19% ID/g overserved at 30 minutes post injection and 22% ID/g observed at 4 hours post drug injection. This data is in line with what is observed with octreotide derivatives and other isotopes (1,2). The drug is nearly undetectable in all other organs by 4 hours post $^{212}$Pb-DOTATOC injection. HPLC is performed on DOTATOC and $^{212}$Pb-DOTATOC. A system suitability test shows the retention time of DOTATOC to be 5.357 min (FIG. 41) and natPb-DOTATOC to be 5.54 min (not shown). $^{212}$Pb-DOTATOC is run with HPLC and fractions collected at 15 second intervals for a total of 10 minutes. The fractions are quantified by auto gamma counter and the radiometric plot is overlaid onto the HPLC chromatogram. The radiometric maximum is observed at 6.5 minutes. This suggests that the $^{212}$Pb-DOTATOC is within 15% of the retention time observed with cold Pb-DOTATOC.

Combination Therapy Efficacy Study in Ar42J Xenograft Bearing Athymic Nude Mice Treated with Adrucil® and $^{212}$Pb-DOTAMTATE at Treatment Cycles of Two Weeks and Three Weeks Methods:

Athymic nude mice are given AR42J tumors and allowed to grow until tumors reach about 300 mm$^3$. Mice in treatment groups are injected with 100 µl of 15 mg/kg ADRUCIL® once weekly for a total of nine injections. 10 µCi of $^{212}$Pb-DOTAMTATE is given at either 2 week or 3 week intervals for a total of 3 treatments. The $^{212}$Pb-DOTAMTATE is given within 24 hours after an ADRUCIL® treatment. 10 µCi per 4.1 ng peptide is used, and the cumulative injection dose is 30 µCi. The animals are monitored daily, and calipered and weighed 3 times per week. The animals are sacrificed when termination criteria are met.

Results:

1$^{st}$ injections

| | $^{212}$Pb-DOTAMTATE |
|---|---|
| ITLC - Free Lead | 2.5% |
| Actual injected dose | 10.4 µCi |

2$^{nd}$ injections—2 week group

| | $^{212}$Pb-DOTAMTATE |
|---|---|
| ITLC - Free Lead | 1% |
| Actual injected dose | 10.6 µCi |

2$^{nd}$ injections—3 week group

| | $^{212}$Pb-DOTAMTATE |
|---|---|
| ITLC - Free Lead | 2% |
| Actual injected dose | 10.9 µCi |

3$^{rd}$ injections—2 week group

| | $^{212}$Pb-DOTAMTATE |
|---|---|
| ITLC - Free Lead | 2.4% |
| Actual injected dose | 9.2 µCi |

3$^{rd}$ injections—3 week group

| | $^{212}$Pb-DOTAMTATE |
|---|---|
| ITLC- Free Lead | 1.5% |
| Actual injected dose | 10.4 µCi |

Figure 43:
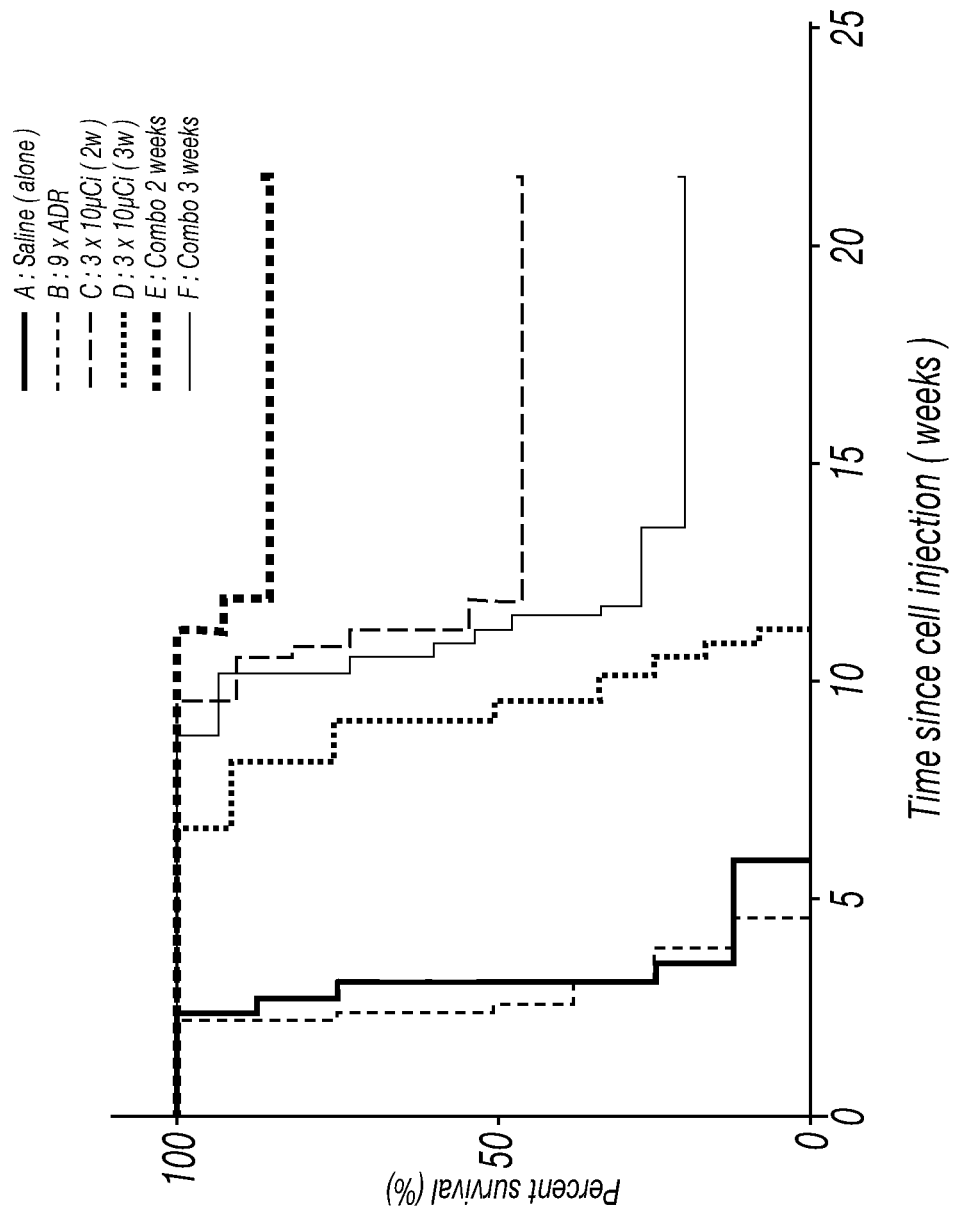
FIG. 43 is a graph of Kaplan Meier survival curves of mice treated with $^{212}$Pb-DOTAMTATE.

Referring to FIGS. 42 and 43, animals that are injected with ADRUCIL® alone had a median survival of 2.4 weeks while the saline alone group had a median survival of 3.1 weeks post cell injection. Mice that receive three injections of $^{212}$Pb-DOTAMTATE only at 3-week intervals have a median survival rate of 9.14 weeks while combination therapy with ADRUCIL® lead to a longer median survival of 11.1 weeks with 20% of the mice still alive 21 weeks post cell injection. This suggests that the addition of ADRUCIL® radiosensitizer improves median survival by 18% with a three-week $^{212}$Pb-DOTAMTATE treatment cycle.

Interestingly, the better efficacy is observed by decreasing the time between injections of $^{212}$Pb-DOTAMTATE. The treatment group that received 3×10 µCi of $^{212}$Pb-DOTAMTATE at 2-week intervals had a median survival rate of 11.9 weeks with 46% of the animals still remaining at 21 weeks post cell injection. The highest efficacy is observed when mice are treated with radiosensitizer ADRUCIL® and $^{212}$Pb-DOTAMTATE at 2-week intervals. 85% of the animals are alive at 21 weeks post cell injection with all tumors under the limit of quantification of 200 mm$^3$.

Dosimetry and Bio-Distribution of $^{203}$Pb-DOTAMTATE in Patients with Somatostatin Expressing Neuroendocrine Tumors Method:

Total of 6 patients are enrolled in the first-in-human open-label, single-dose, dosimetry and bio-distribution of $^{203}$Pb-DOTAMTATE.

All patients (1 female and 5 male) receive an average dose of 4.94 (4.66-5.26) mCi of $^{203}$Pb-DOTAM-TATE and undergo 1 hour, 4 hour, 24 hour and 48 hour post injection SPECT-CT scans. Ethnicity of all 6 patients is Caucasian.

Pharmacokinetic data from $^{203}$Pb-DOTAMTATE imaging are used to calculate the absorbed dose from $^{203}$Pb-DOTAMTATE imaging. The data is then extrapolated to calculate the expected tissue absorbed doses following the administration of $^{212}$Pb-DOTAMTATE for future Targeted Alpha particle Therapy (TAT).

According to the measured data obtained from the dosimetry of $^{203}$Pb-DOTAM-TATE the kidneys and liver receives the highest absorbed doses, averaging 19 and 17 mGy/MBq, respectively, for $^{212}$Pb when a Relative Biological Effectiveness (RBE) of 3 is used for the α-particle emissions of $^{212}$Bi and $^{212}$Po. Experience from external beam radiotherapy suggests that 18-23 Gy to the whole kidney volume gives a 5% risk of kidney injury in 5 years. The liver can tolerate 27-30 Gy (twice daily fractions, 1.5 Gy per fraction). Although the spleen receives the highest absorbed dose it is not a dose-limiting organ since it is not a vital organ. The dose to bone marrow, lungs, heart wall, osteogenic cells and spleen at this administered activity would be 1.6, 2.5, 3.7, 0.5 and 31 Gy, respectively. Except for spleen, for which toxicity limit is not well established, these doses are all below toxicity limits for these organs.

Comparison of $^{68}$Ga-DOTATATE PET/CT and $^{203}$Pb-DOTAMTATE SPECT/CT Scans

Reports of these two imaging modalities are independently read by two nuclear medicine physicians blinded to the results of the other study for 6 enrolled patients. Total number of 177 lesions in 6 patients are detected by $^{68}$Ga-DOTATATE scan while 109 lesions are detectable by $^{203}$Pb-DOTAMTATE. There is a very close correlation (with correlation coefficient of 0.89) between lesions detected by these two modalities. Total discovered lesions per organ is comparable in visceral (42 versus 38) and nodal (12 versus 13) but not for skeletal lesions (123 versus 58). It seems that $^{68}$Ga PET/CT scan is more sensitive to detect bone lesions in axial skeleton (vertebrae, bony thorax, bony pelvis) area (total of 95) as compared to $^{203}$Pb-DOTAMTATE (total of 34).

Results:

There is no statistically significant difference observed between the $^{68}$Ga DOTATATE PET/CT and $^{203}$Pb-DOTAMTATE SPECT/CT, thereby indicating that $^{68}$Ga DOTATATE can be used in lieu of $^{203}$Pb-SPECT/CT to evaluate the eligibility of patients undergoing Targeted Alpha Therapy (TAT) with $^{212}$Pb-DOTAMTATE.

Based on the dosimetry analysis the maximum theoretical absorbed dose estimate to kidneys is 23 Gy which corresponds to cumulative dose of 32.7 mCi of $^{212}$Pb-DOTAMTATE (10.9 mCi per therapy cycle for a total of 3 cycles).

The methods herein may be performed in any order and repeated as desired.

While the embodiments are described with reference to various implementations and exploitations, it will be understood that these embodiments are illustrative and that the scope of the inventive subject matter is not limited to them. Many variations, modifications, additions and improvements are possible. For example, various combinations of part or all of the techniques described herein may be performed.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Insofar as the description above and the accompanying drawings disclose any additional subject matter that is not within the scope of the claim(s) herein, the inventions are not dedicated to the public and the right to file one or more applications to claim such additional invention is reserved. Although a very narrow claim may be presented herein, it should be recognized the scope of this invention is much broader than presented by the claim(s). Broader claims may be submitted in an application that claims the benefit of priority from this application.

What is claimed is:

1. A cancer targeting composition comprising a molecule of Formula (I) or a pharmaceutically acceptable salt thereof:

$$M\text{-Ch-L}^1\text{-Tm,} \qquad \text{Formula (I)}$$

wherein:

M is $^{212}$Pb or $^{203}$Pb;

Ch is a chelator having a structure of Formula (V):

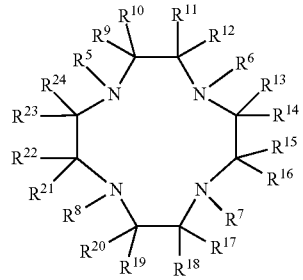

Formula (V)

wherein:

R$^5$, R$^6$, and R$^8$ are each (C$_1$-C$_6$)alkyl-C(=O)—N(—R$^{25}$)—R$^{26}$;

R$^9$, R$^{10}$, R$^{11}$, R$^{12}$, R$^{15}$, R$^{16}$, R$^{17}$, R$^{18}$, R$^{19}$, R$^{20}$, R$^{21}$, R$^{22}$, R$^{23}$, and R$^{24}$ are each independently H, D, F, Cl, or (C$_1$-C$_6$)alkyl;

$R^7$ is $(C_1-C_6)$alkyl-C(=O)—N(—$R^{25}$)—$R^{26}$ or $L^1$;

$R^{13}$ and $R^{14}$ are each independently H, D, F, Cl, $(C_1-C_6)$alkyl, or $L^1$;

$R^{25}$ and $R^{26}$ are each independently H, D, $(C_1-C_6)$alkyl, or $(C_1-C_6)$alkyl-C(=O)—OH;

$L^1$ is R$(C_1-C_6)$alkyl-C(=O)—NH—$(C_1-C_6)$alkyl-C(=O)—NH, $(C_1-C_6)$alkyl-$(C_6H_4)$—NH—C(=S)—NH, C(—CO$_2$H)—$(C_1-C_6)$alkyl-$(C_6H_4)$—NH—C(=S)—NH, $(C_1-C_6)$alkyl-C(=O)—NH, or $(C_1-C_6)$alkyl-C(=O)—(O—CH$_2$—CH$_2$)$_{1-20}$—C(=O)—NH; and Tm has a structure of Formula (VI):

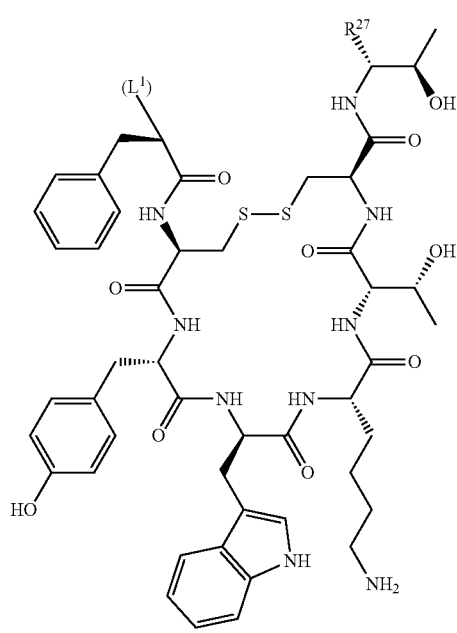

Formula (VI)

wherein:

$R^{27}$ is CH$_2$—OH or C(=O)—OH; and ($L^1$) is $L^1$ and connects to Ch to Tm, provided that only one of $R^7$, $R^{13}$, or $R^{14}$ is $L^1$.

2. The cancer targeting composition of claim 1, having a structure of Formula (VII) or a pharmaceutically acceptable salt thereof:

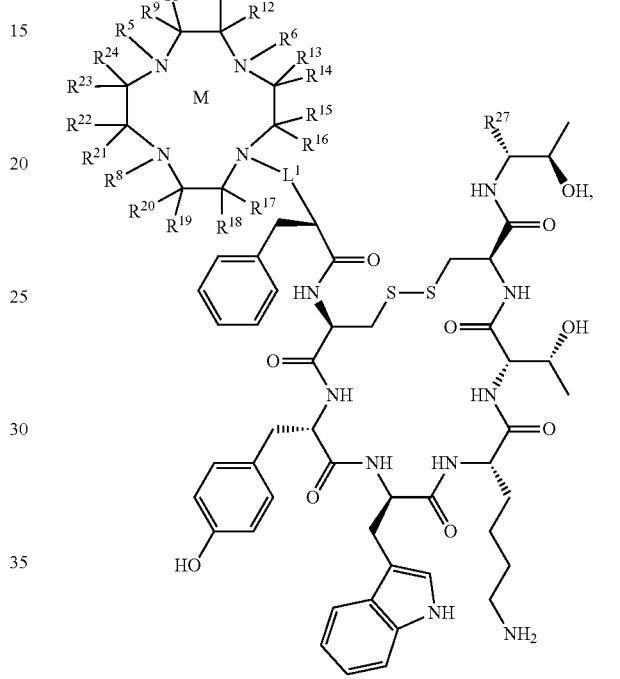

Formula (VII)

wherein:

M is $^{212}$Pb or $^{203}$Pb;

$R^5$, $R^6$, and $R^8$ are each independently $(C_1-C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently H, D, F, Cl, or $(C_1-C_6)$alkyl;

$R^{13}$ and $R^{14}$ are each independently H, D, F, Cl, or $(C_1-C_6)$alkyl;

$R^{25}$ and $R^{26}$ are each independently H, D, $(C_1-C_6)$alkyl, or $(C_1-C_6)$alkyl-C(=O)—OH;

$L^1$ is $(C_1-C_6)$alkyl-C(=O)—NH—$(C_1-C_6)$alkyl-C(=O)—NH, $(C_1-C_6)$alkyl-$(C_6H_4)$—NH—C(=S)—NH, C(—CO$_2$H)—$(C_1-C_6)$alkyl-$(C_6H_4)$—NH—C(=S)—NH, $(C_1-C_6)$alkyl-C(=O)—NH, or $(C_1-C_6)$alkyl-C(=O)—(O—CH$_2$—CH$_2$)$_{1-20}$—C(=O)—NH; and $R^{27}$ is CH$_2$—OH or C(=O)—OH.

3. The cancer targeting composition of claim 1, having a structure of Formula (VIII) or a pharmaceutically acceptable salt thereof:

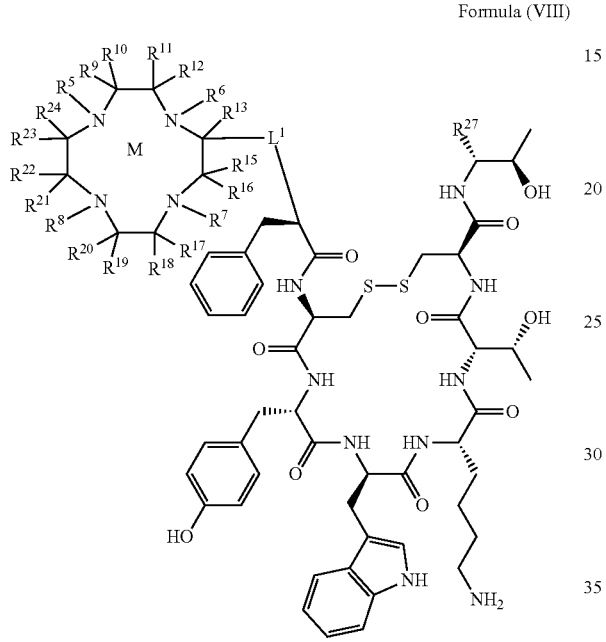

Formula (VIII)

wherein:

M is $^{212}$Pb or $^{203}$Pb;

$R^5$, $R^6$, and $R^8$ are each independently $(C_1\text{-}C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently H, D, F, Cl, or $(C_1\text{-}C_6)$alkyl;

$R^7$ is $(C_1\text{-}C_6)$alkyl-C(=O)—N(—$R^{25}$)—$R^{26}$;

$R^{13}$ is H, D, F, Cl, or $(C_1\text{-}C_6)$alkyl;

$R^{25}$ and $R^{26}$ are each independently H, D, $(C_1\text{-}C_6)$alkyl, or $(C_1\text{-}C_6)$alkyl-C(=O)—OH;

$L^1$ is $(C_1\text{-}C_6)$alkyl-$(C_6H_4)$—NH—C(=S)—NH; and $R^{27}$ is $CH_2$—OH or C(=O)—OH.

4. The cancer targeting composition of claim 1, having a structure of Formula (IX) or a pharmaceutically acceptable salt thereof:

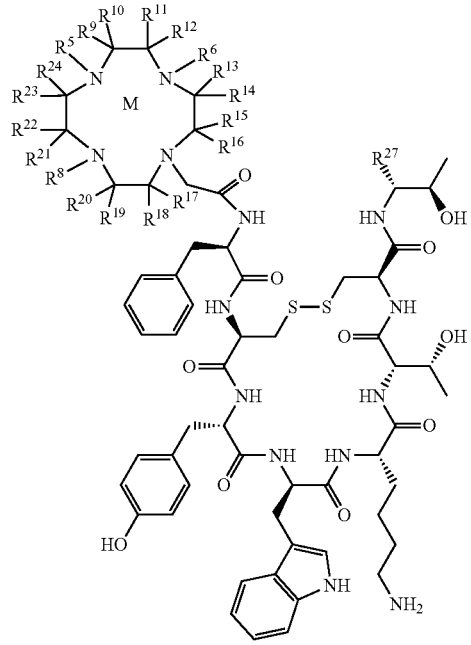

Formula (IX)

wherein:

M is $^{212}$Pb or $^{203}$Pb;

$R^5$, $R^6$, and $R^8$ are each independently $(C_1\text{-}C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently H, D, F, Cl, or $(C_1\text{-}C_6)$alkyl;

$R^{13}$ and $R^{14}$ are each independently H, D, F, Cl, or $(C_1\text{-}C_6)$alkyl;

$R^{25}$ and $R^{26}$ are each independently H, D, $(C_1\text{-}C_6)$alkyl, or $(C_1\text{-}C_6)$alkyl-C(=O)—OH; and $R^{27}$ is $CH_2$—OH or C(=O)—OH.

5. A cancer targeting kit for treatment of cancer cells overexpressing somatostatin receptors, the cancer targeting kit comprising:

the cancer targeting composition of claim 1; and at least one of a pharmaceutically acceptable buffer, an antioxidant, and a scavenger.

6. The cancer targeting kit of claim 5, which comprises 25 µg to 50 µg of the cancer targeting composition and 0.4M ammonium acetate buffer.

7. The cancer targeting kit of claim 5, wherein the pharmaceutically acceptable buffer is an ammonium acetate buffer.

8. The cancer targeting kit of claim 5, wherein the antioxidant is ascorbic acid, gentisic acid, ethanol, or a combination thereof.

9. The cancer targeting kit of claim 5, wherein the scavenger is diethylenetriaminopentaacetic; ethylene diamine tetraacetic acid; 1,4,7,10-tetraazacyclododecane-1,4,7,10-tetraacetic; or a combination thereof.

10. A pharmaceutical formulation comprising the cancer targeting composition of claim 1 and a pharmaceutically acceptable buffer.

11. A method of treating cancer cells overexpressing somatostatin receptors to a subject in need thereof, the method comprising:

administering a therapeutically effective dosage of a cancer targeting composition, the cancer targeting composition comprising a molecule of Formula (I) or a pharmaceutically acceptable salt thereof:

M-Ch-L¹-Tm,   Formula (I)

wherein:

M is $^{212}$Pb or $^{203}$Pb;

Ch is a chelator having a structure of Formula (V):

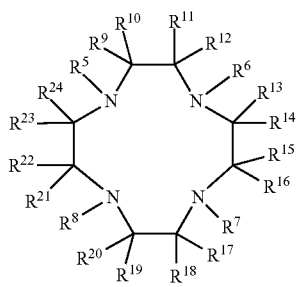

Formula (V)

wherein:

$R^5$, $R^6$, and $R^8$ are each $(C_1-C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently H, D, F, Cl, or $(C_1-C_6)$alkyl;

$R^7$ is $(C_1-C_6)$alkyl-C(=O)—N(—$R^{25}$)—$R^{26}$ or $L^1$;

$R^{13}$ and $R^{14}$ are each independently H, D, F, Cl, $(C_1-C_6)$alkyl, or $L^1$;

$R^{25}$ and $R^{26}$ are each independently H, D, or $(C_1-C_6)$alkyl, or $(C_1-C_6)$alkyl-C(=O)—OH;

$L^1$ is $(C_1-C_6)$alkyl-C(=O)—NH—$(C_1-C_6)$alkyl-C(=O)—NH, $(C_1-C_6)$alkyl-$(C_6H_4)$—NH—C(=S)—NH, C(—$CO_2$H)—$(C_1-C_6)$alkyl-$(C_6H_4)$—NH—C(=S)—NH, $(C_1-C_6)$alkyl-C(=O)—NH, or $(C_1-C_6)$alkyl-C(=O)—(O—$CH_2$—$CH_2$)$_{1-20}$—C(=O)—NH;

Tm has a structure of Formula (VI):

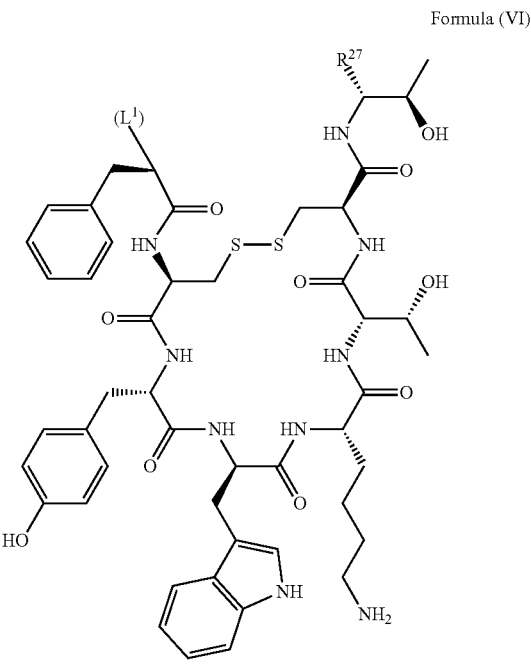

Formula (VI)

wherein:

$R^{27}$ is $CH_2$—OH or C(=O)—OH; and ($L^1$) is $L^1$ and connects to Ch to Tm, provided that only one of $R^7$, $R^{13}$, or $R^{14}$ is $L^1$.

12. The method of claim 11, wherein the cancer comprises cells overexpressing somatostatin receptors.

13. The method of claim 11, wherein the cancer is a cardiac cancer, a lung cancer, a gastrointestinal cancer, genitourinary tract cancer, a liver cancer, a bone cancer, a nervous system cancer, gynecological cancer, a hematologic cancer, or a combination thereof.

14. The method of claim 11, wherein the subject is a mammal.

15. The method of claim 11, wherein the cancer targeting composition is administered in combination with at least one anti-cancer compound, wherein the at least one anti-cancer compound is aldesleukin; alemtuzumab; alitretinoin; allopurinol; altretamine; amifostine; anastrozole; arsenic trioxide; asparaginase; BCG Live; bexarotene; bleomycin; busulfan; calusterone; capecitabine; carboplatin; carmustine; carmustine with polifeprosan 20 implant; celecoxib; chlorambucil; cisplatin; cladribine; cyclophosphamide; cytarabine; cytarabine liposomal; dacarbazine; dactinomycin, actinomycin D; darbepoetin alfa; daunorubicin liposomal; daunorubicin, daunomycin; denileukin diftitox, dexrazoxane; docetaxel; doxorubicin; doxorubicin liposomal; dromostanolone propionate; Elliott's B Solution; epirubicin; epoetin alfa estramustine; etoposide; exemestane; filgrastim; floxuridine; fludarabine; 5-fluorouracil; fulvestrant; gemcitabine; gemtuzumab ozogamicin; imatinib; goserelin; hydroxyurea; ibritumomab tiuxetan; idarubicin; ifosfamide; imatinib mesylate; interferon alfa-2a; interferon alfa-2b; irinotecan; letrozole; leucovorin; levamisole; lomustine; mechlorethamine; megestrol; melphalan; 6-mercaptopurine; mesna; methotrexate; methoxsalen; mitomycin C; mitotane; mitoxantrone; nandrolone phenpropionate; nofetumomab; LOddC; oprelvekin; oxaliplatin; paclitaxel; pamidronate;

pegademase; pegaspargase; pegfilgrastim; pentostatin; pipobroman; plicamycin; mithramycin; porfimer sodium; procarbazine; quinacrine; rasburicase; rituximab; sargramostim; streptozocin; surafenib; talbuvidine; talc; tamoxifen; erlotinib; temozolomide; teniposide; testolactone; 6-thioguanine; thiotepa; topotecan; toremifene; tositumomab; trastuzumab; tretinoin; uracil mustard; valrubicin; valtorcitabine; vinblastine; vinorelbine; zoledronate; or a mixture thereof.

16. The method of claim 15, wherein the anti-cancer compound is administered in a therapeutically effective dosage.

17. A method of treating cancer cells overexpressing somatostatin receptors to a subject in need thereof, the method comprising:

administering a therapeutically effective dosage of a molecule of Formula (I), or a pharmaceutically acceptable salt thereof, and at least one anti-cancer compound in a pharmaceutically acceptable carrier, M-Ch-L$^1$-Tm,                Formula (I)

wherein:

M is $^{212}$Pb or $^{203}$Pb;

Ch is a chelator having a structure of Formula (V):

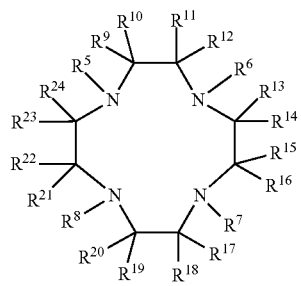

Formula (V)

wherein $R^5$, $R^6$, and $R^8$ are each $(C_1-C_6)$alkyl-C(=O)—N(—$R^{25}$)—$R^{26}$;

$R^9$, $R^{10}$, $R^{11}$, $R^{12}$, $R^{15}$, $R^{16}$, $R^{17}$, $R^{18}$, $R^{19}$, $R^{20}$, $R^{21}$, $R^{22}$, $R^{23}$, and $R^{24}$ are each independently H, D, F, Cl, or $(C_1-C_6)$alkyl;

$R^7$ is $(C_1-C_6)$alkyl-C(=O)—N(—$R^{25}$)—$R^{26}$ or $L^1$;

$R^{13}$ and $R^{14}$ are each independently H, D, F, Cl, $(C_1-C_6)$alkyl, or $L^1$;

$R^{25}$ and $R^{26}$ are each independently H, D, $(C_1-C_6)$alkyl, or $(C_1-C_6)$alkyl-C(=O)—OH;

$L^1$ is $(C_1-C_6)$alkyl-C(=O)—NH—$(C_1-C_6)$alkyl-C(=O)—NH, $(C_1-C_6)$alkyl-$(C_6H_4)$—NH—C(=S)—NH, C(—CO$_2$H)—$(C_1-C_6)$alkyl-$(C_6H_4)$—NH—C(=S)—NH, $(C_1-C_6)$alkyl-C(=O)—NH, or $(C_1-C_6)$alkyl-C(=O)—(O—CH$_2$—CH$_2$)$_{1-20}$—C(=O)—NH; and Tm has a structure of Formula (VI):

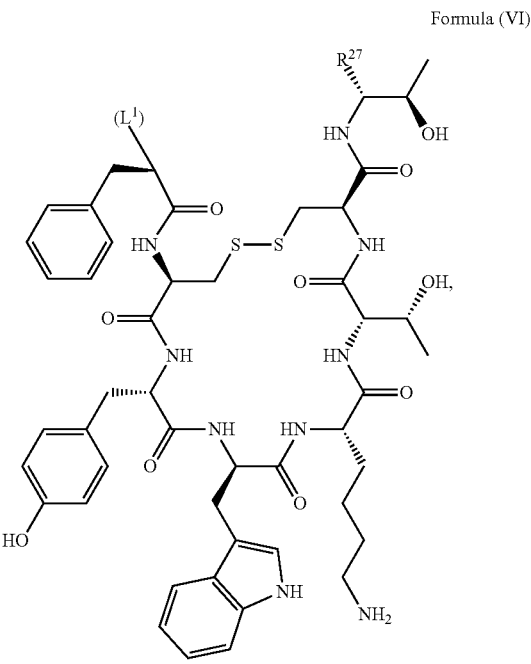

Formula (VI)

wherein:

$R^{27}$ is CH$_2$—OH or C(=O)—OH; and (L$^1$) is L$^1$ and connects to Ch to Tm, provided that only one of $R^7$, $R^{13}$, or $R^{14}$ is L$^1$.

18. The method of claim 17, wherein the at least one anti-cancer compound is aldesleukin; alemtuzumab; alitretinoin; allopurinol; altretamine; amifostine; anastrozole; arsenic trioxide; asparaginase; BCG Live; bexarotene; bleomycin; busulfan; calusterone; capecitabine; carboplatin; carmustine; carmustine with polifeprosan 20 implant; celecoxib; chlorambucil; cisplatin; cladribine; cyclophosphamide; cytarabine; cytarabine liposomal; dacarbazine; dactinomycin, actinomycin D; darbepoetin alfa; daunorubicin liposomal; daunorubicin, daunomycin; denileukin diftitox, dexrazoxane; docetaxel; doxorubicin; doxorubicin liposomal; dromostanolone propionate; Elliott's B Solution; epirubicin; epoetin alfa estramustine; etoposide; exemestane; filgrastim; floxuridine; fludarabine; 5-fluorouracil; fulvestrant; gemcitabine; gemtuzumab ozogamicin; imatinib; goserelin; hydroxyurea; ibritumomab tiuxetan; idarubicin; ifosfamide; imatinib mesylate; interferon alfa-2a; interferon alfa-2b; irinotecan; letrozole; leucovorin; levamisole; lomustine; mechlorethamine; megestrol; melphalan; 6-mercaptopurine; mesna; methotrexate; methoxsalen; mitomycin C; mitotane; mitoxantrone; nandrolone phenpropionate; nofetumomab; LOddC; oprelvekin; oxaliplatin; paclitaxel; pamidronate; pegademase; pegaspargase; pegfilgrastim; pentostatin; pipobroman; plicamycin; mithramycin; porfimer sodium; procarbazine; quinacrine; rasburicase; rituximab; sargramostim; streptozocin; surafenib; talbuvidine; talc; tamoxifen; erlotinib; temozolomide; teniposide; testolactone; 6-thioguanine; thiotepa; topotecan; toremifene; tositumomab; trastuzumab; tretinoin; uracil mustard; valrubicin; valtorcitabine; vinblastine; vinorelbine; zoledronate; or a combination or a mixture thereof.

19. The method of claim 18, wherein the at least one anti-cancer compound is administered in a therapeutically effective dosage.

20. The cancer targeting composition of claim 2, having the structure represented by the following Formula:
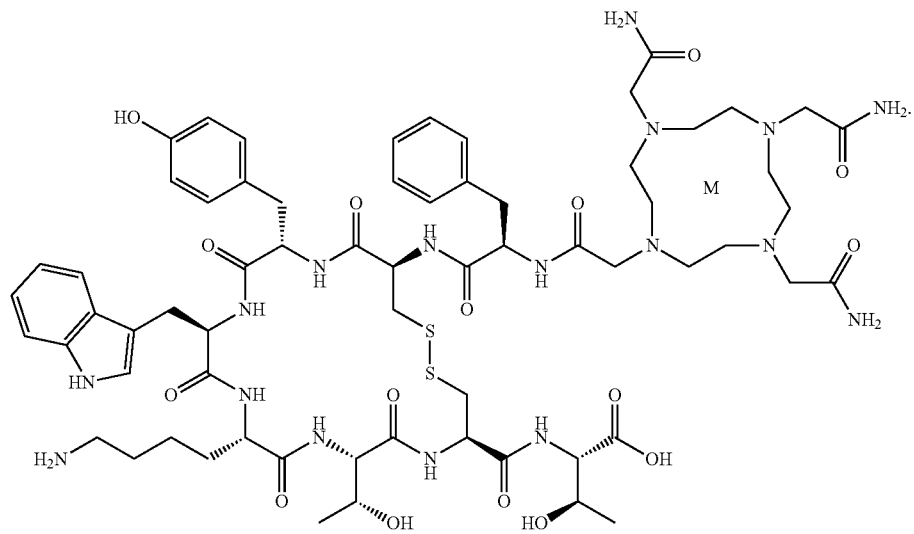
21. The cancer targeting composition of claim 3, having the structure represented by the following Formula:
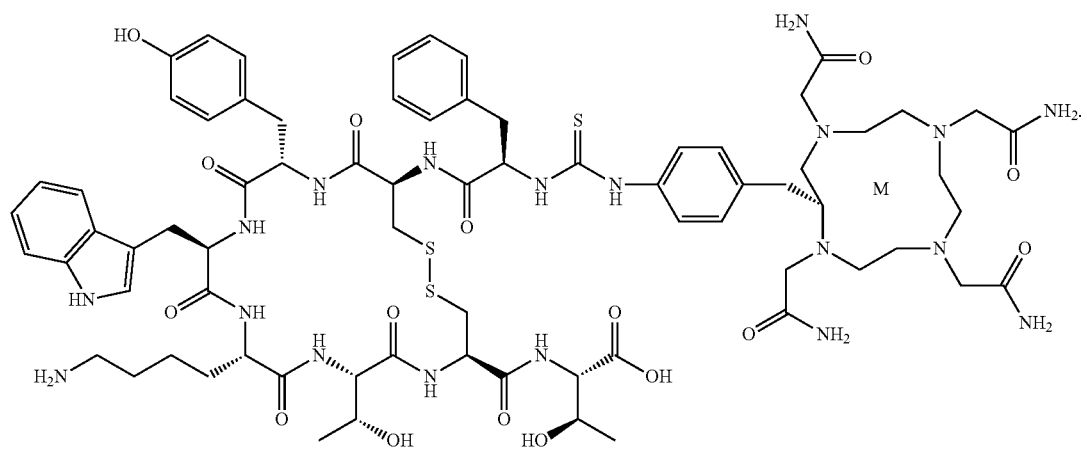
22. The method of claim 14, wherein the mammal is a dog, a cat, or a horse.
* * * * *